United States Patent
Namba et al.

(10) Patent No.: US 8,174,686 B2
(45) Date of Patent: May 8, 2012

(54) FOCAL POSITION DETERMINING METHOD, FOCAL POSITION DETERMINING APPARATUS, FEEBLE LIGHT DETECTING APPARATUS AND FEEBLE LIGHT DETECTING METHOD

(75) Inventors: Akihiro Namba, Tokyo (JP); Hirobumi Suzuki, Hino (JP); Hiroshi Ishiwata, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/058,150

(22) Filed: Mar. 28, 2008

(65) Prior Publication Data
US 2008/0225278 A1    Sep. 18, 2008

Related U.S. Application Data

(63) Continuation of application No. PCT/JP2006/319589, filed on Sep. 29, 2006.

(30) Foreign Application Priority Data

Sep. 29, 2005 (JP) .................................. 2005-285537
Sep. 30, 2005 (JP) .................................. 2005-288619

(51) Int. Cl.
*G01J 1/00* (2006.01)
*G01B 9/00* (2006.01)
*G01B 11/14* (2006.01)
*G02B 7/04* (2006.01)
*G02B 27/40* (2006.01)
*G02B 27/64* (2006.01)
*G03B 3/00* (2006.01)

(52) U.S. Cl. ..... 356/123; 356/124; 356/624; 250/201.2; 250/201.7

(58) Field of Classification Search ..................... None
See application file for complete search history.

(56) References Cited

U.S. PATENT DOCUMENTS

| | | | | |
|---|---|---|---|---|
| 3,783,270 A | * | 1/1974 | Kamachi | 250/201.4 |
| 4,083,057 A | * | 4/1978 | Quinn | 396/78 |
| 4,568,165 A | * | 2/1986 | Ishibashi | 396/136 |
| 5,548,661 A | * | 8/1996 | Price et al. | 382/133 |
| 5,604,351 A | * | 2/1997 | Bisconte | 250/458.1 |

(Continued)

FOREIGN PATENT DOCUMENTS

JP           05-313068         11/1993

(Continued)

OTHER PUBLICATIONS

Kennedy, Helen J. et al., "Glucose Generates Sub-plasma Membrane ATP Microdomains in Single Islet β-Cells", The Journal of Biological Chemistry (1999), vol. 274, No. 19, pp. 13281-13291.

*Primary Examiner* — Tarifur Chowdhury
*Assistant Examiner* — Gordon Stock, Jr.
(74) *Attorney, Agent, or Firm* — Scully, Scott, Murphy & Presser, P.C.

(57) ABSTRACT

A focal position determining method determines a focal position of an objective lens focused on an observed target region in a specimen. The focal position determining method includes measuring any one of the focal position of the objective lens at a near point and the focal position of the objective lens at a far point or both so as to determine the focal position of the objective lens focused on the observed target region based on the measured focal position.

11 Claims, 34 Drawing Sheets

U.S. PATENT DOCUMENTS

| | | | |
|---|---|---|---|
| 5,790,710 A * | 8/1998 | Price et al. .................... 382/255 |
| 5,932,872 A * | 8/1999 | Price .......................... 250/201.3 |
| 5,956,141 A | 9/1999 | Hayashi |
| 5,995,143 A * | 11/1999 | Price et al. .................... 348/345 |
| 6,130,745 A | 10/2000 | Manian et al. |
| 6,259,080 B1 * | 7/2001 | Li et al. ...................... 250/201.3 |
| 6,384,967 B1 * | 5/2002 | Watanabe et al. ............. 359/385 |
| 6,434,274 B1 * | 8/2002 | Horie et al. ................... 382/274 |
| 6,441,894 B1 | 8/2002 | Manian et al. |
| 6,608,314 B1 * | 8/2003 | Hayashi ...................... 250/458.1 |
| 6,728,171 B2 * | 4/2004 | Yanagi et al. ............... 369/44.14 |
| 6,823,079 B1 | 11/2004 | Winterot et al. |
| 7,071,451 B2 * | 7/2006 | Ishikawa et al. ........... 250/201.4 |
| 7,141,773 B2 * | 11/2006 | Kaplan et al. .............. 250/208.1 |
| 7,515,201 B2 * | 4/2009 | Nakahara ...................... 348/354 |
| 2001/0009473 A1 | 7/2001 | Ogino |
| 2002/0061127 A1 * | 5/2002 | Bacus et al. .................. 382/128 |
| 2003/0227673 A1 | 12/2003 | Nakagawa |
| 2004/0105000 A1 | 6/2004 | Yuri |
| 2006/0000962 A1 * | 1/2006 | Imabayashi et al. ........ 250/201.2 |
| 2007/0058159 A1 * | 3/2007 | Greve et al. ................... 356/123 |
| 2009/0086314 A1 * | 4/2009 | Namba et al. .................. 359/383 |
| 2010/0219353 A1 * | 9/2010 | Akiyoshi et al. ............ 250/459.1 |
| 2010/0227316 A1 * | 9/2010 | Suzuki et al. ...................... 435/6 |

FOREIGN PATENT DOCUMENTS

| | | |
|---|---|---|
| JP | H07-104178 | 4/1995 |
| JP | 08075985 A * | 3/1996 |
| JP | H 10-48512 A | 2/1998 |
| JP | 10-89912 | 4/1998 |
| JP | 10-260023 | 9/1998 |
| JP | 2000-321501 A | 11/2000 |
| JP | 2001-208974 | 8/2001 |
| JP | 2002-258163 | 9/2002 |
| JP | 2002-541430 | 12/2002 |
| JP | 2002-542480 | 12/2002 |
| JP | 2003-005021 | 1/2003 |
| JP | 2004-191959 | 7/2004 |
| JP | 2004-354650 | 12/2004 |
| JP | 2005-140956 | 6/2005 |
| JP | 2005-172680 | 6/2005 |
| JP | 2005-173288 | 6/2005 |

* cited by examiner

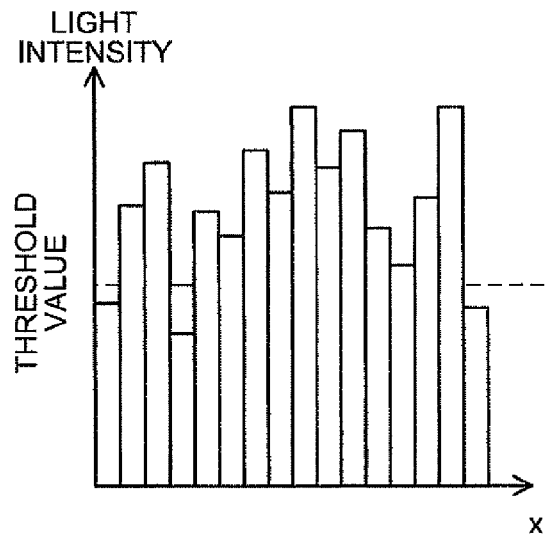
FIG.3A
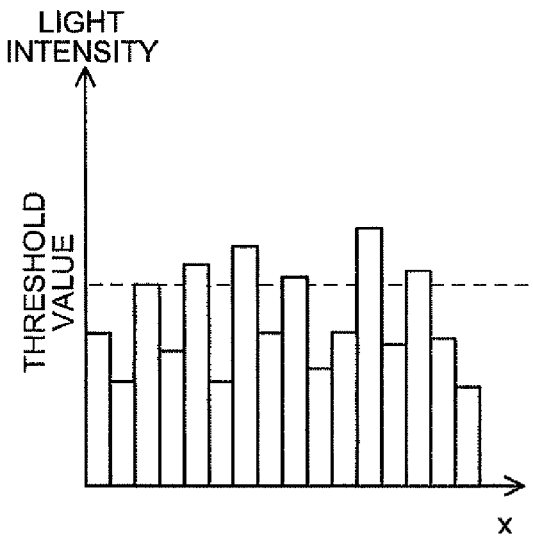
FIG.3B
FIG.4
|  | x20 (NA1.36) | x40 (NA1.36) |
|---|---|---|
| FAR POINT SIDE | 10.512 mm | 10.590 mm |
| CENTRAL POINT | 10.507 | 10.506 |
| NEAR POINT SIDE | 10.500 | 10.503 |

ILLUMINATION
IMAGE

LUMINESCENT
IMAGE

ILLUMINATION IMAGE

LUMINESCENT IMAGE

ILLUMINATION
IMAGE

LUMINESCENT
IMAGE

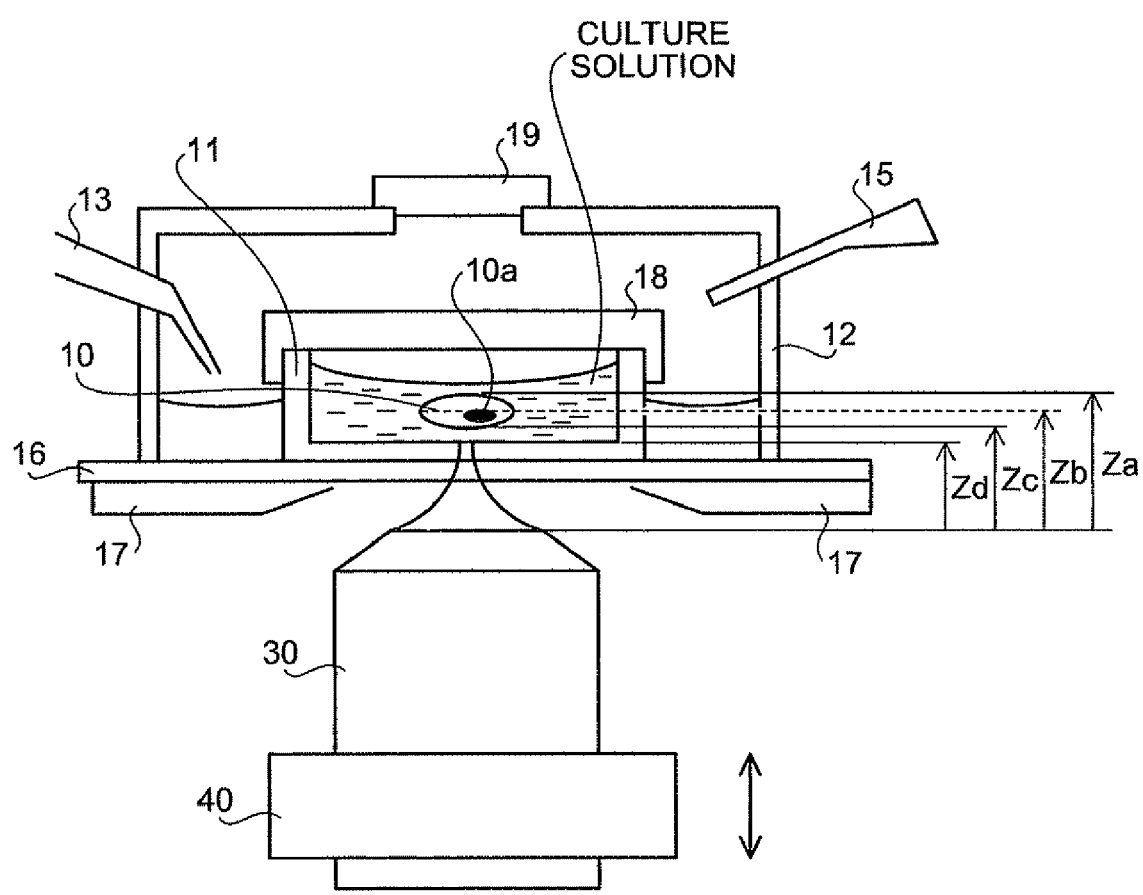

FOCAL POSITION DETERMINING METHOD, FOCAL POSITION DETERMINING APPARATUS, FEEBLE LIGHT DETECTING APPARATUS AND FEEBLE LIGHT DETECTING METHOD

CROSS-REFERENCE TO RELATED APPLICATIONS

This application is a continuation of PCT international application Ser. No. PCT/JP2006/319589 filed Sep. 29, 2006 which designates the United States, incorporated herein by reference, and which claims the benefit of priority from Japanese Patent Application No. 2005-285537, filed Sep. 29, 2005, Japanese Patent Application No. 2005-288619, filed Sep. 30, 2005, and all incorporated herein by reference.

BACKGROUND OF THE INVENTION

1. Field of the Invention

The present invention relates to a focal position determining method and a focal position determining apparatus that determine a focal position of an objective lens focused on an observed target region in a specimen.

The present invention relates to a method and an apparatus for observing or measuring a test specimen of a biological origin that emits a feeble light with magnification imaging optical unit including a lens.

2. Description of the Related Art

[1] In recent years, an imaging technique of a biological sample utilizing fluorescence has taken a great role for a research of a bioscience. A specific protein is marked, and light emission is utilized, whereby various life phenomena happening inside or outside a cell can be observed. Further, dynamic actions of various life phenomena can be known in real time. In recent days, in particular, the use of a fluorescent protein such as GFP (Green Fluorescent Protein) makes it possible to stably and easily realize an imaging of a structure in a cell, so that various life phenomena has been steadily unraveled.

Further, a luminescence-related gene that expresses a bioluminescent protein (specifically, luciferase, aequolin, or the like) has frequently been utilized for various function analyses in a cell (specifically, a luminescence-related gene has frequently been utilized as a reporter molecule of a protein expression). In performing the function analyses described above, it is extremely significant to describe a clear image by bringing a lens into focus on a specific region in a cell, or to efficiently receive light emitted from a specific bioluminescent protein transduced to a cell. However, since an intensity of light of self-luminescence from a biological specimen is generally extremely feeble, the luminescence from the biological specimen cannot directly be confirmed with naked eyes in most cases. Even when an optical element (e.g., detection lens, etc.) is adjusted to a specimen emitting a feeble light, it is naturally difficult to bring a lens into focus on the specific region in the specimen with naked eyes.

In view of this, various methods for focusing light on a specimen in a specimen container have been disclosed. However, all of the methods are applicable to the case in which the light from a specimen can be confirmed (visually) with naked eyes. For example, JP-T-2002-541430 and JP-T-2002-542480 disclose a method in which a position of a bottom surface of a specimen container is detected, and light is focused on a specimen in the specimen container based on the detected positional information. In JP-T 2002-541430, light is irradiated to the bottom surface of the specimen container through an objective lens, the intensity of the mirror-reflected light from the bottom surface of the specimen container is sequentially detected while moving the light irradiation position vertically, the position of the bottom surface of the specimen container is detected based on the detected intensity of light, the position of the specimen in the specimen container is estimated based upon the detected positional information, and light is focused on the estimated position. In JP-T-2002-542480, light is diagonally irradiated to the bottom surface of the specimen container from below through an objective lens, a deviation amount of the mirror-reflected light from the bottom surface of the specimen container on an XY plane is detected by a photodetector, the position of the bottom surface of the specimen container on an optical axis is detected based upon the detected deviation amount, the position of the specimen in the specimen container is estimated based upon the detected positional information, and light is focused on the estimated position. Thus, the focal position of the objective lens can be focused on the specimen in the specimen container.

JP-A-2004-354650 and JP-A-2005-173288 disclose a method in which, with the use of a microscope for observing a phase object such as a cell with a bright field, the position of an objective lens is shifted in the forward or rearward direction from the general focusing position to be fixed to thereby obtain an observation image with a high contrast by defocus, in order to observe a cell. With this method, the observation image of the cell, which is the phase object, can be obtained with a high contrast.

[II] In recent years, a technique for analyzing a specimen of a biological origin by utilizing fluorescence or luminescence (chemiluminescence and bioluminescence) has taken a great role for a research of a bioscience. A specific protein is marked, and fluorescence or luminescence is utilized, whereby various life phenomena happening inside or outside a cell can actually be measured. Further, dynamic actions of various life phenomena can be found in real time. In recent days, in particular, the use of a fluorescent protein such as GFP (Green Fluorescent Protein) makes it possible to stably and easily realize an imaging of a structure in a cell, so that the analyzing technique by means of a fluorescent image has steadily been contributed to the unraveling of various life phenomena.

In the analysis of a specimen of a biological origin by means of a fluorescent image, an observation image is optically or electrically (digitally) magnified, and then, an image is analyzed, when a specimen is too small. As one example of this technique, there has been disclosed an apparatus that counts a number of microorganisms by using a magnified image obtained by magnifying a fluorescent image, which is obtained by dyeing the proliferated microorganisms with a fluorescent pigment (see JP-A-2005-172680).

SUMMARY OF THE INVENTION

[I] One aspect of the present invention is a focal position determining method for determining a focal position of an objective lens focused on an observed target region in a specimen. The focal position determining method according to one aspect of the present invention includes measuring any one of the focal position of the objective lens at a near point and the focal position of the objective lens at a far point or both so as to determine the focal position of the objective lens focused on the observed target region based on the measured focal position.

Another aspect of the present invention is a focal position determining method for determining a focal position of an objective lens focused on an observed target region in a specimen. The focal position determining method according to one aspect of the present invention includes a light irradiating step of irradiating light to the specimen, a focal position changing step of changing the focal position of the objective lens, a focal position measuring step of measuring the focal position that is changed at the focal position changing step, a specimen imaging step of imaging the specimen to which light is irradiated at the light irradiating step, at the focal position changed at the focal position changing step, a feature data calculating step of calculating feature data characterizing the imaged image based on the image taken at the specimen imaging step, an executing step of repeatedly executing the focal position changing step, focal position measuring step, specimen imaging step, and feature data calculating step, a focal position selecting step of selecting at least one focal position from the plural focal positions accumulated by the execution of the executing step based on the plural feature data accumulated by the execution, and a focal position determining step of determining the focal position of the objective lens focused on the observed target region based on the focal position selected at the focal position selecting step.

One aspect of the present invention is the focal position determining apparatus that determines a focal position of an objective lens focused on an observed target region in a specimen. The focal position determining apparatus according to one aspect of the present invention includes a light irradiator that irradiates light to the specimen, a focal position changer that changes the focal position of the objective lens, a focal position measurer that measures the focal position of the objective lens, a specimen imager that images the specimen, a feature data calculator that calculates feature data characterizing the imaged image based on the image taken by the specimen imager, a controller that controls the focal position changer, focal position measurer, specimen imager, and feature data calculator so as to repeatedly execute the focal position changer, focal position measurer, specimen imager, and feature data calculator, a focal position selector that selects at least one focal position from the plural focal positions accumulated by the repeated execution by the controller based on the plural feature data accumulated by the repeated execution, and a focal position determining unit that determines the focal position of the objective lens focused on the observed target region based on the focal position selected by the focal position selector.

One aspect of the present invention is the focal position determining method for determining a focal position of an objective lens focused on an observed target region in a specimen, wherein the specimen is imaged while moving the objective lens, as well as the focal position of the objective lens is measured, a contrast that is the difference between the maximum value and the minimum value of a pixel value of each pixel composing the image is calculated based on the imaged image, and the focal position of the objective lens focused on the observed target region is determined based on the calculated contrast and the measured focal position of the objective lens.

[II] One aspect of the present invention is a feeble light detecting apparatus that describes an image of a test specimen of a biological origin by using optical imager. The feeble light detecting apparatus according to one aspect of the present invention includes an image forming step of describing the image of the test specimen with the use of the optical imager, an image extracting step of extracting a desired area from the image obtained at the image forming step, and an image magnifying step of magnifying the area obtained at the image extracting step.

One aspect of the present invention is a feeble light detecting method in which an image of a test specimen of a biological origin is described, a desired area is extracted from the image, and the area is displayed or recorded as magnified.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3A is a graph showing a distribution of light intensity of each pixel contained in a specific pixel array of the CCD camera when the cell is imaged at the position $\alpha$ in FIG. 2;

FIG. 3B is a graph showing a distribution of light intensity of each pixel contained in a specific pixel array of the CCD camera when the cell is imaged at the position $\beta$ in FIG. 2;

FIG. 4 is a table showing the result of the measurement relating to a focal position on an optical axis of an objective lens when two illumination images are imaged and relating to a focal position on the optical axis of the objective lens when a luminescent image is imaged;

FIG. 14 is a view showing one example of configurations of components arranged in the vicinity of a specimen stage 17;

DETAILED DESCRIPTION OF THE PREFERRED EMBODIMENTS

Figure 1:
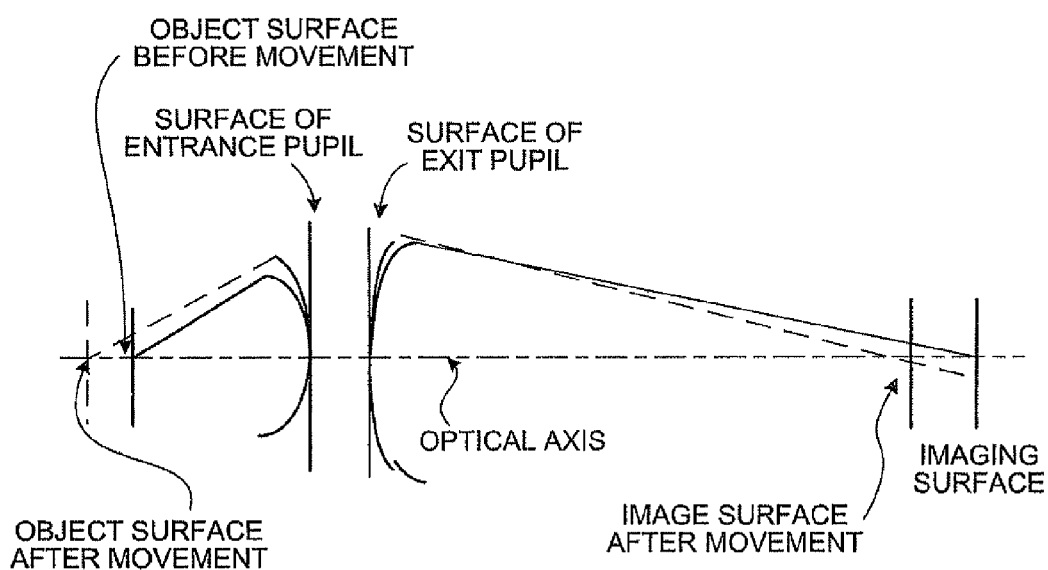
FIG. 1 is a view schematically showing an object point, and an entrance pupil, an exit pupil, and an imaging surface of an optical system.

[I] Embodiments (first embodiment, second embodiment, and third embodiment) of a focal position determining method and a focal position determining apparatus according to the present invention will be explained below in detail with reference to the drawings. The present invention is not limited to the embodiments.

First Embodiment

1. Basic Principle of Present Invention

Firstly, a basic principle of the present invention will be explained in detail with reference to the drawings. The present invention determines a focal position of an objective lens, which is a reference, measures any one of the focal position (substantial focal position) at the near point of the objective lens and the focal position (substantial focal position) at the far point of the objective lens or both with the determined focal position defined as a reference, determines the focal position of the objective lens focused on an observed target region in a specimen based on the measured focal position, and adjusts (moves) the focal position of the objective lens to the determined focal position.

Specifically, the present invention executes: (1) irradiating light to the specimen; (2) any one of moving, for example, any one of the position of the specimen and the position of the objective lens or both in the optical axis direction, and changing the focal distance of the objective lens (in this case, a variable focus lens is employed) or both, so as to change the focal position of the objective lens by a fixed amount, for example; (3) measuring the changed focal position; (4) imaging the specimen, to which the light is irradiated, by using a CCD (Charge Coupled Device) camera at the changed focal position; (5) calculating feature data (e.g., contrast of the imaged image, integral value of the brightness of the imaged image, statistic amount obtained from the brightness distribution of the imaged image, ratio of the pixel number having the brightness exceeding a predetermined threshold value and a total pixel number of the imaged image, etc.) that characterize the imaged image based on the imaged image; (6) repeating the processes at (2) to (5); (7) selecting at least one focal position (specifically, any one of the focal position at the near point of the objective lens and the focal position at the far point of the objective lens or both) from the plural focal positions (coordinate values on the optical axis representing the focal positions of the objective lens) accumulated by the execution based on plural feature data accumulated by the execution; (8) determining the focal position of the objective lens focused on the observed target region in the specimen based on the selected focal position; and (9) any one of moving any one of the position of the specimen and the position of the objective lens or both, for example, in the optical axis direction, and changing the focal distance of the objective lens (in this case, the variable focus lens is employed) or both, so as to adjust (move) the focal position of the objective lens to the determined focal position.

In the above-described (7), the present invention may select two focal positions (specifically, the focal position (substantial focal position) at the near point of the objective lens and the focal position (substantial focal position) at the far point of the objective lens) from the plural focal positions accumulated by the execution based on the plural feature data accumulated by the execution, and in the above-described (8), the present invention may determine the central position (substantial central position) between the two focal positions as the focal position of the objective lens that is focused on the observed target region in the specimen, based on the selected two focal positions.

In the above-described (7), the present invention may select one focal position (specifically, the focal position (substantial focal position) at the near point of the objective lens or the focal position (substantial focal position) at the far point of the objective lens) from the plural focal positions accumulated by the execution based on the plural feature data accumulated by the execution, and in the above-described (8), the present invention may determine the position apart from the selected focal position by a predetermined distance as the focal position of the objective lens that is focused on the observed target region in the specimen, based on the selected one focal position and the predetermined distance.

The present invention may further execute: (10) imaging the luminescent image of the specimen by using the CCD camera at the focal position determined at (8); (11) calculating the feature data based on the imaged image; (12) changing the focal position determined at (8); (13) imaging the luminescent image of the specimen by using the CCD camera at the changed focal position; (14) calculating the feature data based on the imaged image; (15) comparing the feature data calculated at (11) and the feature data calculated at (14); (16) when the feature data calculated at (14) is greater as a result of the comparison, determining again the focal position changed at (12) as the focal position of the objective lens focused on the observed target region in the specimen.

In the present invention, an aperture may be arranged as decentered for example relative to the optical axis at the pupil position of an illumination optical system including the light source used at (1). Further, a narrow band-pass filter may be arranged at the illumination optical system including the light source used at (1). The present invention may use a light source emitting monochromatic visible light as the light source used in (1). The present invention may use a living cell or tissue as the specimen.

Taking the case in which a living cell is used as the specimen as one example, the principle of generating a contrast, proportional to the phase distribution of the living cell, to the imaged image (image obtained by illumination light) will be explained with reference to FIG. 1. FIG. 1 is a view schematically showing an object point, and an entrance pupil, an exit pupil, and an imaging surface of an optical system.

When a living cell (object) is arranged at a focusing position, and then, light is irradiated to the object, the light emitted from the object spreads spherically as indicated by a solid line to be incident on the entrance pupil. The light incident on the entrance pupil is emitted from the exit pupil, and the light emitted from the exit pupil becomes spherical converged light to be converged on the imaging surface as indicated by the solid line, whereby the image of the object is finally formed. During the process for forming the image, the difference in the optical paths (phase difference) of rays passing through the optical system is not produced, so that blur does not appear on the image. When the object point is then moved to the position indicated by a dotted line and light is irradiated to the object as shown in FIG. 1, the light emitted from the object spherically spreads to be incident on the entrance pupil as indicated by the dotted line. The light incident on the entrance pupil is emitted from the exit pupil, and the light emitted from the exit pupil becomes spherical converged light to be converted on the imaging surface after the movement as indicated by the dotted line, whereby the image of the object is finally formed. From the above, if the object is observed with the position of the imaging surface after the movement defined as an observation point, a difference in optical paths (phase difference) of the rays passing through the optical system is not produced, while if the object is observed with the position of the imaging surface at the beginning defined as the observation point, the difference in optical paths (phase difference) of the rays is produced.

A living cell can generally optically be treated as a phase object. A living cell has generally the similar shape. Therefore, when illumination light is incident on a cultured living cell distributed on a petri dish, the irradiation light is diffracted in the specific direction dependent on the shape of the living cell since the living cell functions as a diffraction grating, so that the diffraction light can be observed. Specifically, when illumination light is incident on the cell in the petri dish from the specific direction, the diffraction is caused on the incident light depending upon the cell. Therefore, zero-order diffraction light (transmitted light) is generated in the direction of the incident light, and further, first-order diffraction light is generated to the transmitted light in the direction of specific angle.

From the above, the living cell is arranged at the position deviated from the focusing position of the optical system, so as to be capable of producing the phase difference in the rays passing through the optical system. The living cell is observed at the position deviated in the front or to the rear from the focusing position of the observation optical system, whereby the phase difference according to the deviation amount (defocus amount) from the focusing position can be produced between the light transmitted through the living cell and the light diffracted in the living cell. Specifically, the objective lens is moved along the optical axis so as to be focused on the position where the focal position of the objective lens is defined as the focusing position in the ordinary observation, and the objective lens is moved from the moved position by a slight amount, whereby the phase difference proportional to the moving amount can be produced between the rays passing through the observation optical system. This phase difference becomes the greatest in the ray passing through the maximum NA of the objective lens. In this case, some diffraction lights are diffracted to the outside of the NA of the objective lens due to the oblique illumination, and hence, do not transmit through the observation optical system, resulting in that an image having a contrast and a relief-like texture can be formed, like the case of the refraction light.

Specifically, by utilizing the phenomena described above, a clear image of a living cell obtained by illumination light (illumination image) can be obtained, so that the observation same as that by a phase contrast microscope or a differential interference microscope can be carried out. As a result, the produced amount of the phase difference achieves the function equal to the function of a phase film used in the phase contrast observation method, whereby contrast proportional to the phase distribution of the living cell can be provided to the observation image. Consequently, a living cell that is colorless and transparent can be observed with a high contrast.

When a magnification of the observation optical system is reduced in a case where a living cell is observed with a higher contrast, an angle of diffraction light passing through the observation optical system is limited. Therefore, the contrast of the observation image can be increased.

When a phase object such as a living cell is observed, the contrast proportional to the phase distribution of the phase object is proportional to the phase amount of the phase object and the phase difference amount given between the transmitted light and the diffraction light. Further, the angle between the transmitted light and the diffraction light changes depending upon the shape of the phase object. When the angle between the transmitted light and the diffraction light changes, the phase difference amount produced between two beams differs, even if the defocus amounts are the same. In view of this, the aperture is arranged as decentered relative to the optical axis of the illumination optical system at the pupil position of the illumination optical system of the microscope, whereby illumination light that irradiates the object at a specific angle can be generated. Since the diffraction light that is more angled than the transmitted light, transmitting in the direction of the incident light to the object, by the degree of the decentering of the aperture can be incident on the entrance pupil of the optical system, the phase difference between the transmitted light and the diffraction light can be more increased. In other words, the aperture is arranged as decentered from the optical axis of the illumination optical system, whereby the diffraction light can be more angled than the transmitted light. Therefore, the phase difference between the transmitted light and the diffraction light can be more increased (see JP-A-2004-354650). Specifically, the contrast of the observation image can be more increased by increasing the phase difference between the transmitted light and the diffraction light according to these methods.

The sign of the phase difference between the beams generated by the defocus is different between the case in which the object is shifted toward the near point from the focusing position of the observation optical system and the case in which the object is shifted toward the far point. Therefore, the image of the object having a high contrast can be obtained at two positions on the optical axis by the defocus. The contrast of the image that is obtained by shifting the phase object such as a cultured cell toward the near point from the focusing position of the observation optical system to be observed and the contrast of the image that is obtained by shifting the phase object toward the far point to be observed are reversed to each other corresponding to the phase distribution of the phase object. Since the object absorbing light from dusts or the like adhered on the bottom surface of the petri dish is no more a phase object, the contrast of the image is not changed even if the phase difference is generated to the object by the defocus. Accordingly, a phase object can clearly be distinguished from an object that is not a phase object by the defocus. An inter-image operation is performed to the image obtained by shifting the object toward the near point and the image obtained by shifting the object toward the far point, whereby the image components that are not affected by the phase difference provided by the defocus can be separated. In particular by performing the subtraction between the pixels of two images, the contrast of the image component corresponding to the phase distribution of the object can be doubled. Therefore, the image components having no phase information such as dusts, foreign matters, illumination unevenness, etc. can be eliminated. Specifically, this method can more enhance the contrast of the observation image.

Figure 2:
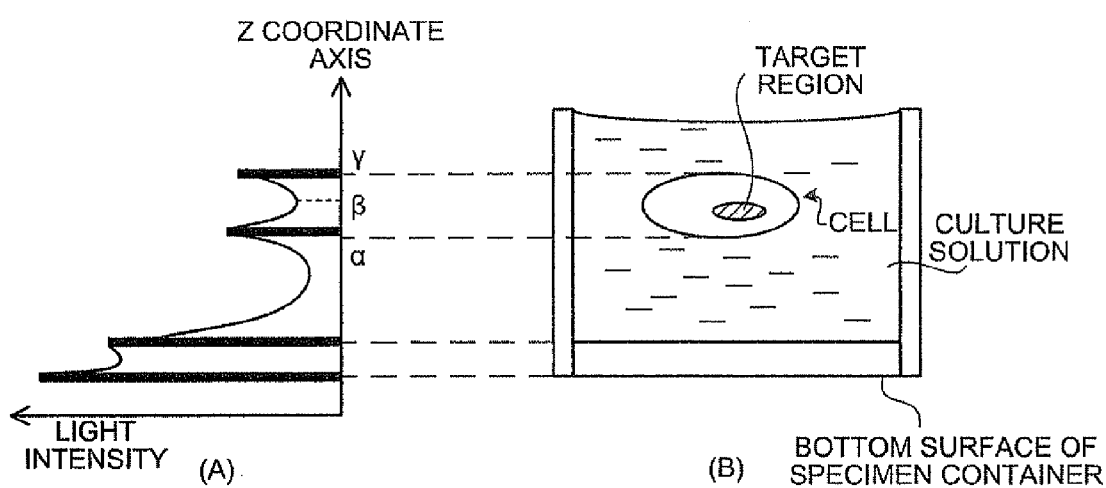
FIG. 2 is a view showing one example of a manner of change of an output signal from each pixel of a CCD camera when a cell is imaged by the CCD camera while moving an objective lens, and schematically showing a position of a petri dish and a position of the cell corresponding to the manner of the change.

Next explained with reference to FIGS. 2, 3A, and 3B are one example of a manner of the change in an output signal (a digital signal corresponding to the light intensity of light caught by each pixel) from each pixel of a CCD camera when a living cell is imaged by the CCD camera while moving the objective lens, and one example of a manner of determining the focal position of the objective lens focused on a specific region (an observed target region) in the living cell based upon the manner of the change in the output signal. When illumination light is irradiated to a living cell, which is immersed in culture solution put in the specimen container (petri dish), and the living cell is imaged by the CCD camera while moving the objective lens from the lower part to the upper part of the petri dish along the optical axis (z axis), the relationship between the integrated values of the output signals (light intensity, light detecting signal) from all pixels of the CCD camera and the focal position (coordinate on the z axis) of the objective lens shown in FIG. 2(A) is established. FIG. 2(B) is a view showing the schematic illustration of the position of the petri dish and the position of the living cell corresponding to FIG. 2(A).

Specifically, when the objective lens is moved upward along the optical axis, the integrated value of the light intensity from all pixels of the CCD camera becomes the maximum and the greatest at the position of the outer bottom surface of the specimen container where the illumination light is strongly reflected. When the objective lens is further moved upward along the optical axis, the integrated value of the light intensity from all pixels of the CCD camera gradually reduces, and then, again becomes the maximum at the position of the inner bottom surface of the specimen container. Since the difference in a refractive index of the inner bottom surface of the specimen container and the refractive index of the culture solution that comes in contact with the inner bottom surface is smaller than the difference in the refractive index of the outer bottom surface of the specimen container and the refractive index of the contact surface of air, the integrated value at the position of the inner bottom surface of the specimen container is smaller than the integrated value at the position of the outer bottom surface of the specimen container. When the objective lens is further moved upward along the optical axis, the integrated value of the light intensity from all pixels of the CCD camera sharply reduces, and then, becomes the maximum again at the position $\alpha$ shown in FIG. 2(A). This position $\alpha$ is the position on the z axis where the imaged image having a high contrast due to the defocus can be obtained. At the position $\alpha$, the objective lens is focused on the portion (lower peripheral edge portion) at the substantial lower edge of the living cell. When the objective lens is further moved upward along the optical axis, the integrated value of the light intensity from all pixels of the CCD camera reduces, and becomes the minimum at the position $\beta$ shown in FIG. 2(A). At this position $\beta$, the objective lens is focused on the approximate central position of the living cell. When the objective lens is further upward along the optical axis, the integrated value of the light intensity from all pixels of the CCD camera increases, and again becomes the maximum at the position $\gamma$ shown in FIG. 2(A). This position $\gamma$ is also the position on the z axis where the imaged image having a high contrast due to the defocus can be obtained. At the position γ, the objective lens is focused on the portion (upper peripheral edge portion) at the substantial upper edge of the living cell.

Specifically, within the region (including the position β) from the position α to the position γ in FIG. 2(A), the objective lens is focused on the inside of the living cell, whereby the focal position of the objective lens focused on the specific region in the living cell can be determined based on the position α and the position γ. The position β may be determined as the focal position of the objective lens focused on the predetermined region in the living cell.

The output signals exceeding a predetermined threshold value are selected as effective output signals from the output signal (digital signal corresponding to the intensity of the light caught by each pixel) from each pixel of the CCD camera when the living cell is imaged at the position α in FIG. 2(A) and the output signal from each pixel of the CCD camera when the living cell is imaged at the position β in FIG. 2(A), and the intensity distribution of the selected each output signal is obtained (see FIGS. 3A and 3B). FIG. 3A is a view showing the distribution of the light intensity of each pixel contained in the specific pixel array of the CCD camera when the living cell is imaged at the position α in FIG. 2(A), and FIG. 3B is a view showing the distribution of the light intensity (the light intensity of the output signal at about the center of the inside of the cell) of each pixel contained in the specific pixel array of the CCD camera when the living cell is imaged at the position β in FIG. 2(A). In FIGS. 3A and 3B, a dotted line indicates a threshold value. The intensity distribution shown in FIGS. 3A and 3B is statistically processed, whereby the focal position of the objective lens by which an image having a high contrast can be obtained can be determined. The number of the pixels of the light intensity exceeding a threshold value, which is greater than the threshold value shown in FIGS. 3A and 3B, may be calculated, and the ratio (calculated pixel number÷total pixel number) of the calculated number of pixels to the total pixel number may be calculated, with the focal position of the objective lens being moved along the optical axis, wherein the focal position of the objective lens where this ratio is the highest may be determined as the focal position of the objective lens by which an image having a highest contrast can be obtained.

Subsequently, to what degree the focal position of the objective lens, which is determined based on the focal positions of the objective lens when two images (illumination images) having a high contrast are imaged, is focused on the central region (e.g., the luminescent region) in the living cell, is confirmed by actually imaging the luminescent image of the cell. The living cell used here is a HeLa cell to which a luciferase gene (pGS3-control vector: (by Promega) is transduced with a luciferin in an amount of 1 mM added thereto. The luminescent image is obtained by imaging the HeLa cell after it is exposed for one minute at room temperature.

Figure 5:
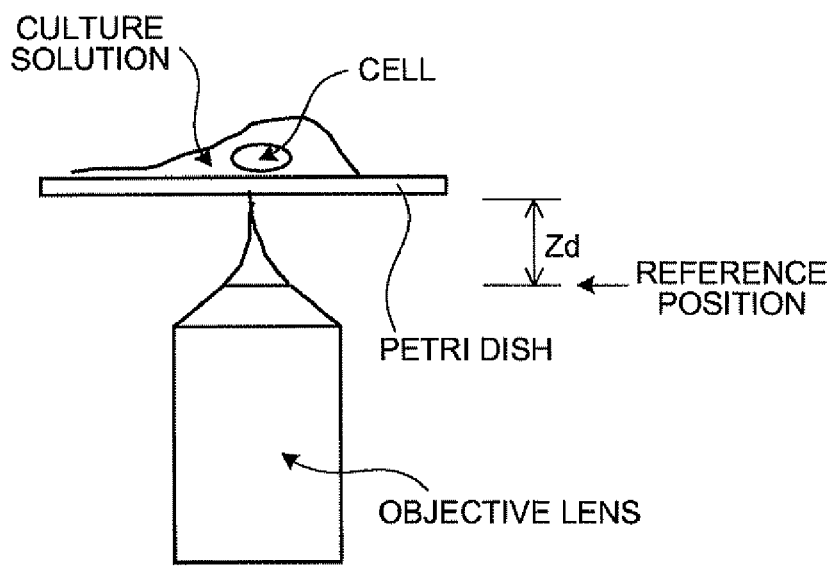
FIG. 5 is a view schematically showing the focal position of the objective lens when the objective lens is focused on the position of the outer bottom surface of the petri dish.

Firstly, as the objective lens is moved along the optical axis, the HeLa cell is imaged as irradiated with the illumination light source, in order to select the imaged image (illumination image) taken at the far point of the objective lens and having the highest contrast and the imaged image (illumination image) taken at the near point of the objective lens and having the highest contrast. On the other hand, the HeLa cell is imaged without being irradiated while moving the objective lens along the optical axis in order to select the imaged image (luminescent image) having the highest contrast. Then, the focal position of the objective lens (×20, ×40) on the optical axis when the selected two illumination images are imaged and the focal position of the objective lens (×20, ×40) on the optical axis when the selected luminescent image is imaged are measured. The result of the measurement is shown in FIG. 4. As shown in FIG. 5, the measured focal position is the same as the distance from the position (reference position) of the objective lens on the optical axis when the objective lens is focused on the position of the outer bottom surface of the specimen container (petri dish).

Figure 6A:
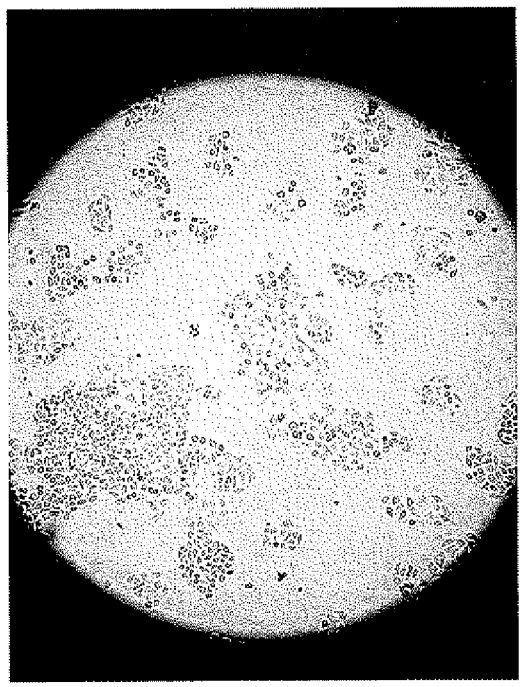
FIG. 6A is a view showing an illumination image having the highest contrast imaged at the near point.
Figure 6B:
FIG. 6B is a view showing a luminescent image having the highest contrast imaged at the near point.
Figure 7:
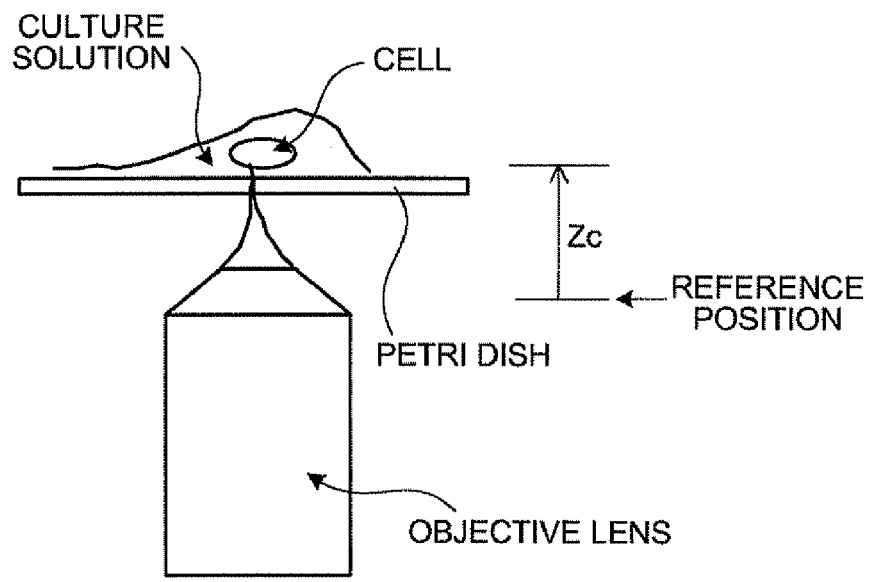
FIG. 7 is a view schematically showing the focal position of the objective lens when the images in FIG. 6A and FIG. 6B are imaged.
Figure 8A:
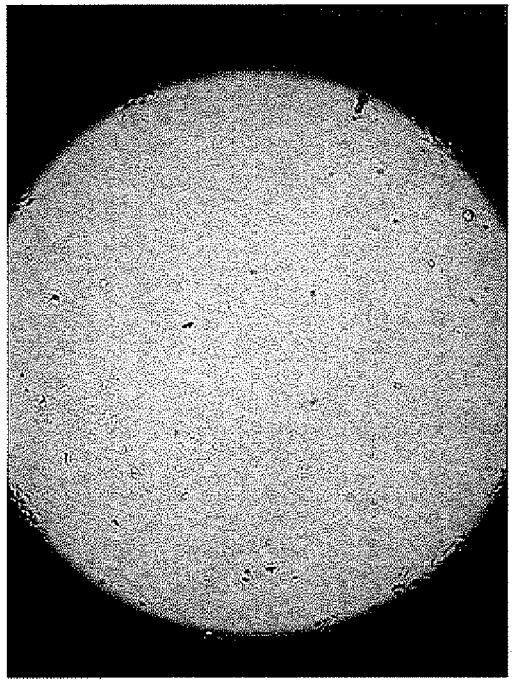
FIG. 8A is a view showing an illumination image having the highest contrast imaged at the central point.
Figure 8B:
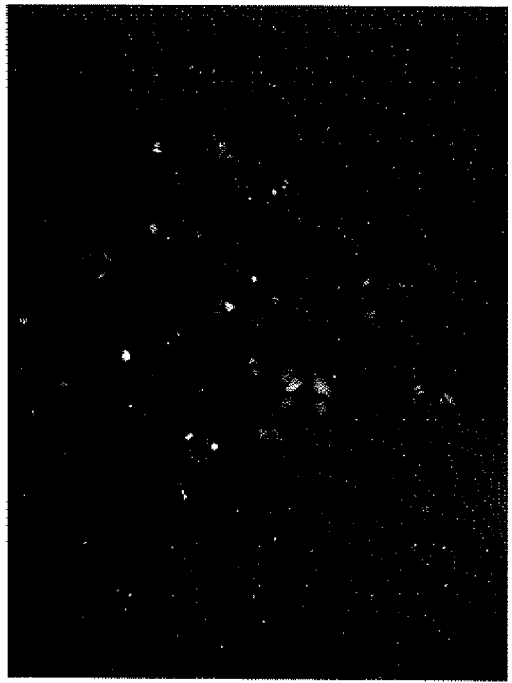
FIG. 8B is a view showing a luminescent image having the highest contrast imaged at the central point.
Figure 9:
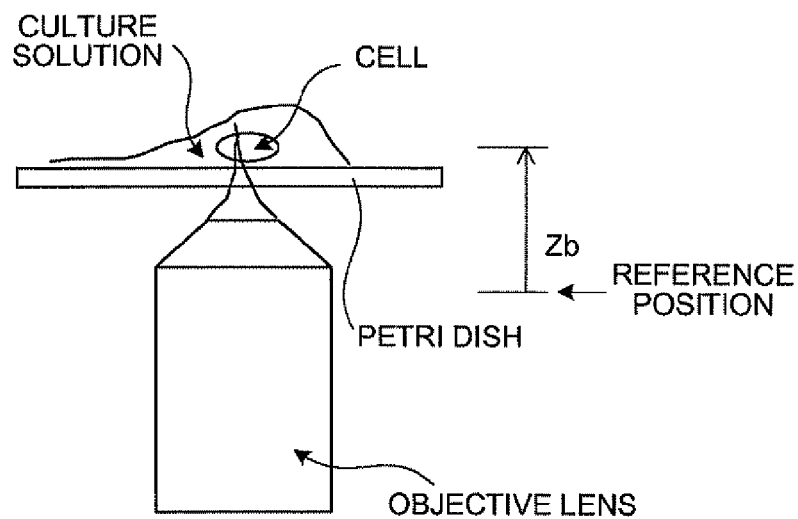
FIG. 9 is a view schematically showing the focal position of the objective lens when the images in FIG. 8A and FIG. 8B are imaged.
Figure 10A:
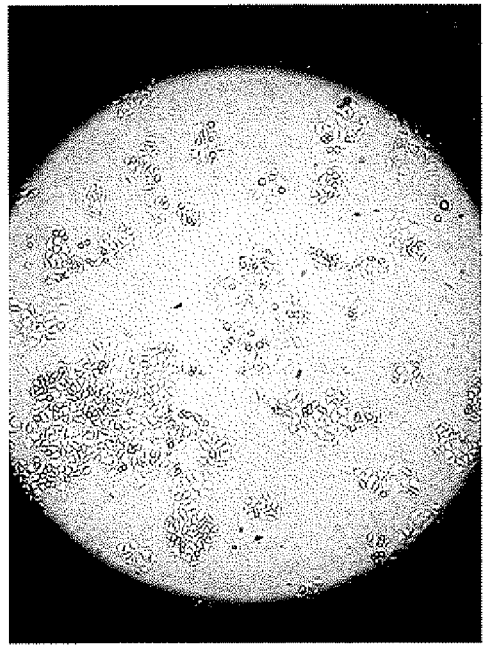
FIG. 10A is a view showing an illumination image having the highest contrast imaged at the far point.
Figure 10B:
FIG. 10B is a view showing a luminescent image having the highest contrast imaged at the far point.
Figure 11:
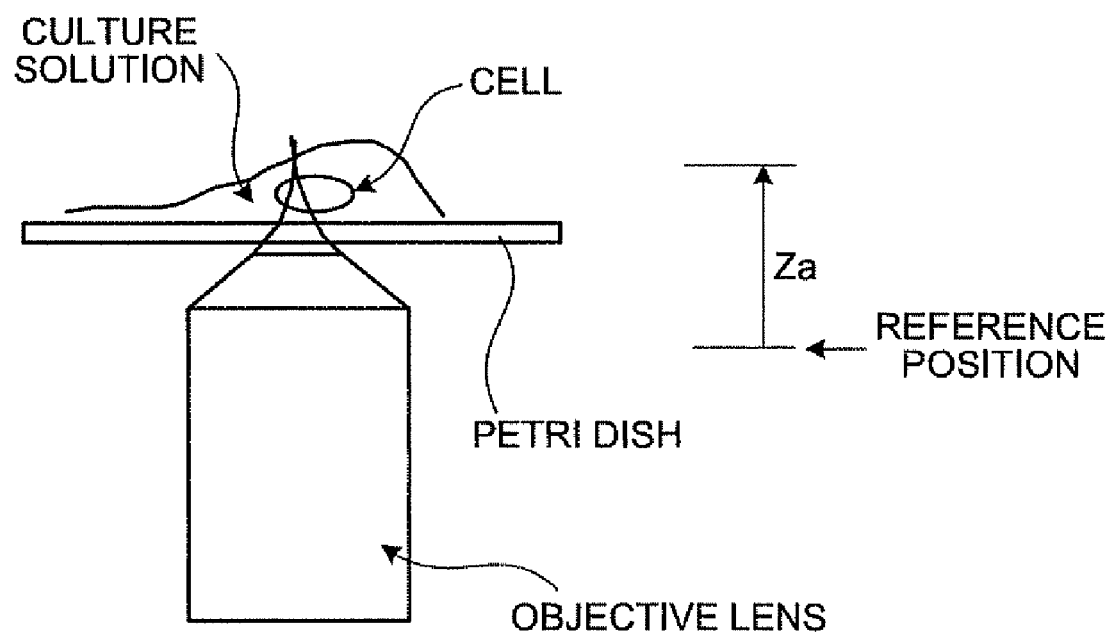
FIG. 11 is a view schematically showing the focal position of the objective lens when the images in FIG. 10A and FIG. 10B are imaged.

As shown in FIG. 4, the focal position (10.507, 10.506 described in the column of "central point" in FIG. 4; "Zb" illustrated in FIG. 9) of the objective lens when the selected luminescent image (FIG. 8B) is imaged is approximately the center of the focal position (10.512, 10.590 described in the column of "far point side" in FIG. 4; "Za" illustrated in FIG. 11) of the objective lens when the illumination image (FIG. 10A) corresponding to the far point is imaged and the focal position (10.500, 10.503 described in the column of "near point side" in FIG. 4; "Zc" illustrated in FIG. 7) of the objective lens when the illumination image (FIG. 6A) corresponding to the near point. Thus, it can be confirmed that the focal position of the objective lens determined based on the focal positions of the objective lens ("Zc" illustrated in FIG. 7 and "Za" illustrated in FIG. 11) when the selected two illumination images (FIG. 6A and FIG. 10A) are imaged is focused on the approximate central region (e.g., luminescent region) in the cell. Specifically, according to the above-mentioned calculation, the objective lens is focused on the approximate central region (e.g., luminescent region) in the cell. FIG. 6A is a view showing the illumination image having the highest contrast and imaged at the near point and FIG. 6B is a view showing the luminescent image having the highest contrast and imaged at the near point. FIG. 7 is a view schematically showing the focal position of the objective lens when the image shown in FIGS. 6A and 6B is imaged. FIG. 8A is a view showing the illumination image having the highest contrast and imaged at the central point and FIG. 8B is a view showing the luminescent image having the highest contrast and imaged at the central point. FIG. 9 is a view schematically showing the focal position of the objective lens when the image shown in FIGS. 8A and 8B is imaged. FIG. 10A is a view showing the illumination image having the highest contrast and imaged at the far point and FIG. 10B is a view showing the luminescent image having the highest contrast and imaged at the far point. FIG. 11 is a view schematically showing the focal position of the objective lens when the image shown in FIGS. 10A and 10B is imaged.

The explanation of the basic principle of the present invention is ended here.

2. Structure of Apparatus

Figure 12:
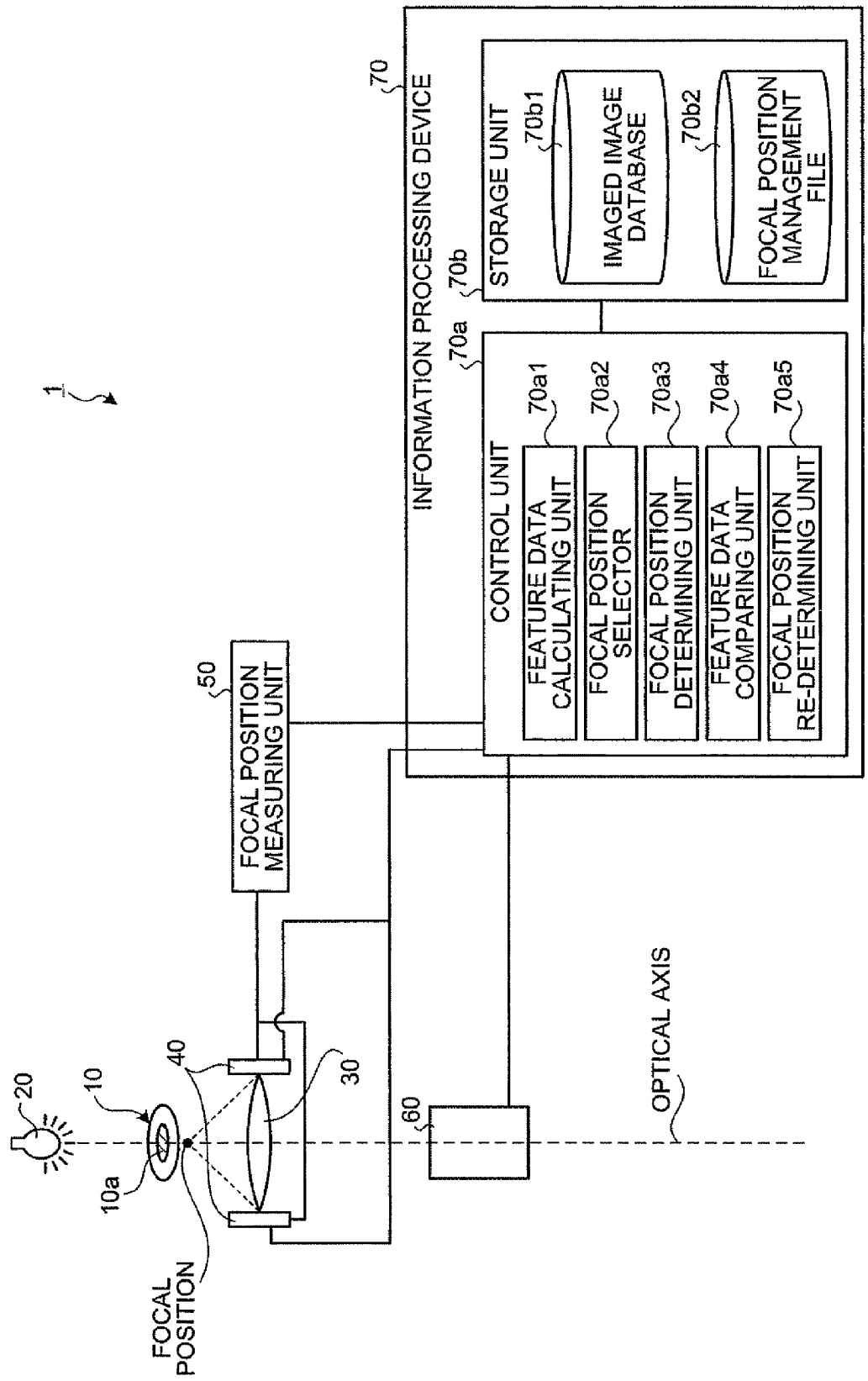
FIG. 12 is a view showing a basic configuration of a focal position determining apparatus 1 according to a first embodiment.

Next, the structure of the focal position determining apparatus 1 according to the first embodiment of the present invention will be explained in detail with reference to FIGS. 12 to 17. Firstly, the basic structure of the focal position determining apparatus 1 according to the first embodiment will be explained with reference to FIG. 12. FIG. 12 is a view showing a basic structure of the focal position determining apparatus 1 according to the first embodiment. The focal position determining apparatus 1 determines the focal position of an objective lens 30 focused on an observed target region 10a in a specimen 10 at the time of setting the specimen 10 such as a living cell or tissue for a luminescent observation. The focal position determining apparatus 1 includes, as shown in FIG. 12, a light irradiating unit 20, the objective lens 30, a focal position changing unit 40, a focal position measuring unit 50, a specimen imaging unit 60, and an information processing device 70.

The light irradiating unit (light source) 20 irradiates light to the specimen 10. The light irradiating unit 20 is an incoherent light source that emits light having a wavelength of visible light region (visible light). Specifically, the light irradiating unit 20 is a halogen lamp, LED (Light Emitting Diode), tungsten lamp, mercury lamp, etc. A coherent light source such as laser may be used as the light irradiating unit 20. In this case, the light (laser beam, or the like) emitted from the coherent light source is changed to an incoherent light with the use of a diffusion plate, and then, irradiated to the specimen 10. Further, a light source emitting infrared ray may be used as the light irradiating unit 20. In this case, since the determination of the focal position by infrared ray can be performed with non-illuminated state, the generation of an image noise caused by self-fluorescence can be prevented, and object information clearer than that obtained by visible light can be obtained. The determination of the focal position by means of infrared ray has an advantage that the determination of the focal position can be performed precisely. Light whose wavelength is partly overlapped with that of the feeble light to be detected, or light that has the same wavelength with that of the feeble light but can significantly detect the feeble light with strong light intensity and in a short period (e.g., within 0.5 second) can be used as irradiation light for determining the focal position.

The objective lens 30 is used for forming an image of the specimen 10. A variable focus lens may be employed as the objective lens 30.

The focal position changing unit 40 executes any one of moving any one of the position of the specimen 10 and the position of the objective lens 30 in the optical axis direction or both and changing the focal distance of the objective lens 30 or both, thereby changing the focal position of the objective lens 30.

The focal position measuring unit 50 is connected to the focal position changing unit 40 for measuring the focal position of the objective lens 30 based on at least one of the position of the specimen 10 on the optical axis, the position of the objective lens 30 on the optical axis, and the focal distance of the objective lens 30.

The specimen imaging unit 60 images the specimen 10. The specimen imaging unit 60 is specifically a high-sensitive CCD camera having an imaging device.

The information processing device 70 is specifically a commercially available personal computer, and is connected to the focal position changing unit 40, the focal position measuring unit 50 and the specimen imaging unit 60. The information processing device 70 includes a control unit 70*a* and a storage unit 70*b*. The control unit 70*a* is a CPU (Central Processing Unit) or the like that integrally controls the control unit 70*a*. The control unit 70*a* has an internal memory for storing a control program such as OS (Operating System), a program prescribing various process procedures, etc., and necessary data, and performs information processing for executing various processes based on the programs.

The control unit 70*a* controls each unit so as to repeatedly operate the focal position changing unit 40, the focal position measuring unit 50, the specimen imaging unit 60, and a later-described feature data calculating unit 70*a*1, and controls each unit provided to the control unit 70*a*. When an input device such as a keyboard or a mouse or an output device such as a TV (Television) monitor is connected to the information processing device 70, the control unit 70*a* acquires information input by the input device and outputs the information to the output device. The control unit 70*a* is composed of the feature data calculating unit 70*a*1, a focal position selector 70*a*2, a focal position determining unit 70*a*3, feature data comparing unit 70*a*4, and a focal position re-determining unit 70*a*5. The feature data calculating unit 70*a*1 calculates feature data (e.g., contrast of an imaged image, an integrated value of brightness of an imaged image, a statistical amount obtained from the brightness distribution of the imaged image, a ratio of a number of pixels having brightness exceeding a predetermined threshold value in the imaged image to the total pixel number, etc.) that characterizes the imaged image based on the imaged image taken by the specimen imaging unit 60. The focal position selector 70*a*2 selects at least one focal position from plural focal positions (focal positions measured at the focal position measuring unit 50) accumulated by the repeated execution of the units (specifically, the focal position changing unit 40, the focal position measuring unit 50, the specimen imaging unit 60, and the feature data calculating unit 70*a*1) by the control unit 70*a* based on the feature data accumulated by the repeated execution. The focal position determining unit 70*a*3 determines the focal position of the objective lens focused on the observed target region 10*a* in the specimen 10 based on the focal position selected by the focal position selector 70*a*2. The feature data comparing unit 70*a*4 compares the two feature data individually calculated beforehand at the feature data calculating unit 70*a*1. The focal position re-determining unit 70*a*5 again determines the focal position of the objective lens focused on the observed target region 10*a* in the specimen 10 based on the result of the comparison made by the feature data comparing unit 70*a*4.

The storage unit 70*b* is storage means. Specifically, a memory device such as a RAM (Random Access Memory) or ROM (Read Only Memory), a fixed disk device such as a hard disk, flexible disk, optical disk, etc., may be employed as the storage unit 70*b*. The storage unit 70*b* stores an imaged image database 70*b*1 and a focal position management file 70*b*2 as shown in the figure. The imaged image database 70*b*1 stores image identification information for uniquely identifying an imaged image, an imaged image, the focal position of the objective lens when the imaged image is taken, and the feature data of the imaged image, as associated with one another. The focal position management file 70*b*2 stores the focal position (specifically, the focal position determined by the focal position determining unit 70*a*3 or the focal position re-determined by the focal position re-determining unit 70*a*5) of the objective lens focused on the observed target region 10*a* in the specimen 10. The imaged image includes an illumination image, luminescent image and fluorescent image.

Figure 13:
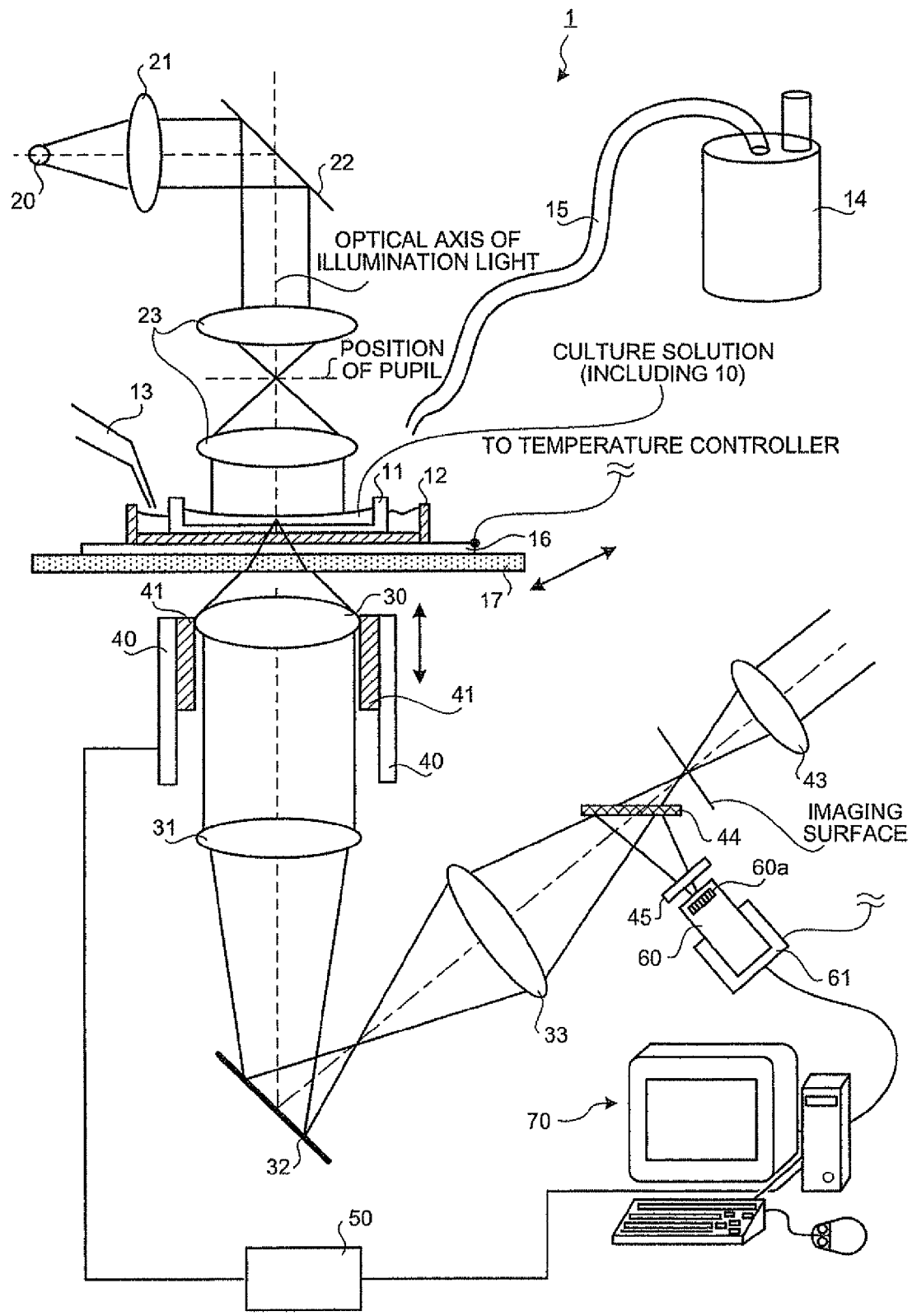
FIG. 13 is a view showing a specific example of the configuration of the focal position determining apparatus 1 according to the first embodiment.

Next, a specific example of the structure of the focal position determining apparatus 1 according to the first embodiment will be explained with reference to FIG. 13. The explanation overlapped with the aforesaid explanation may sometimes be omitted. FIG. 13 is a view showing a specific example of the structure of the focal position determining apparatus 1 according to the first embodiment. The focal position determining apparatus 1 shown in FIG. 13 has a structure with an inverted microscope as a base. Like the focal position determining apparatus 1 shown in FIG. 12, it is used for a luminescent observation of a living cell that emits feeble light. The focal position determining apparatus 1 shown in FIG. 13 includes, in addition to the aforesaid units (light irradiating unit 20, objective lens 30, focal position changing unit 40, focal position measuring unit 50, specimen imaging unit 60, information processing device 70), an illumination optical system, observation optical system, ocular lens 43, etc. Each of the units composing the focal position determining apparatus 1 will be explained below in detail.

The specimen 10 is immersed in culture solution put into a specimen container 11.

The specimen container 11 is specifically a petri dish, with at least its bottom surface being optically transparent (that can be handled with an ordinary objective lens). The bottom surface is made of a material same as a cover glass for a microscope, and has a thickness of 0.17 mm. A slide glass, or microplate can be used as the specimen container 11 instead of the petri dish. A cover 18 may be arranged on the specimen container 11 as shown in FIG. 14. Returning back to FIG. 13, the specimen container 11 is put into a water tank 12 filled with pure water supplied through a nozzle 13. The pure water is put into the water tank 12 in order to keep the humidity in the specimen container 11.

A gaseous mixture (including 5% of carbon dioxide ($CO_2$) and 95% of oxygen ($O_2$)) discharged from a gas cylinder 14 is fed from above the water tank 12 through a gas feed tube 15 with a flow rate of 50 mL/mm. The water tank 12 may be formed into a shape enclosing the entire specimen container 11 as shown in FIG. 14. In this case, a detachable lid 19 is mounted to the upper part of the water tank 12. Returning back to FIG. 13, the water tank 12 is arranged on a heat plate 16.

The heat plate 16 is for setting an environment temperature, and arranged on a specimen stage 17. The heat plate 16 can perform the setting of the environment temperature at 0.5° C. intervals thanks to the control of a temperature controller (not shown) connected to the heat plate 16.

The specimen stage 17 is a plate-like member on which the specimen 10 or the like is set. The specimen stage 17 is arranged so as to be orthogonal to the optical axis (z axis) as shown in the figure. The specimen stage 17 is movable in the direction (e.g., x direction or y direction) orthogonal to the optical axis (z axis) from the position where the stage is arranged by the driving force of two stepping motors (not shown) mounted at the predetermined position of the stage so as to be orthogonal to each other (90° direction). Each of the stepping motors is controlled by a specimen stage controller (not shown) connected to the corresponding motor. The specimen stage controller is connected to the information processing device 70, whereby the specimen stage controller appropriately drives the corresponding stepping motor based on the instruction from the information processing device 70 so as to move the specimen stage 17.

The illumination optical system directs the illumination light emitted from the light source 20 to the specimen 10. The illumination optical system is composed of a collector lens 21, a deflection mirror 22 that deflects the optical axis of the illumination light, and a condenser lens 23 that projects an image of the light source 20.

Figure 15A:
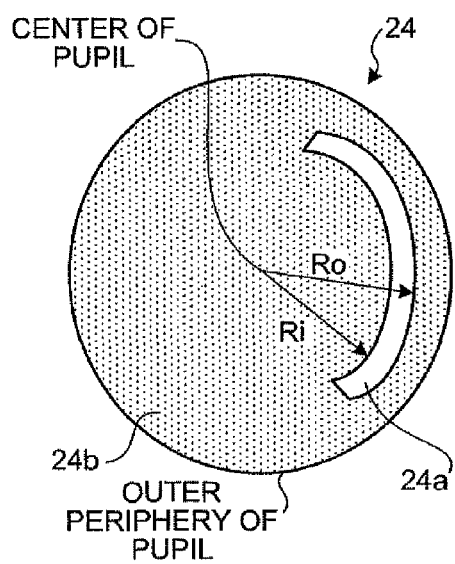
FIG. 15A is a view showing one example of a configuration of an aperture unit 24.
Figure 15B:
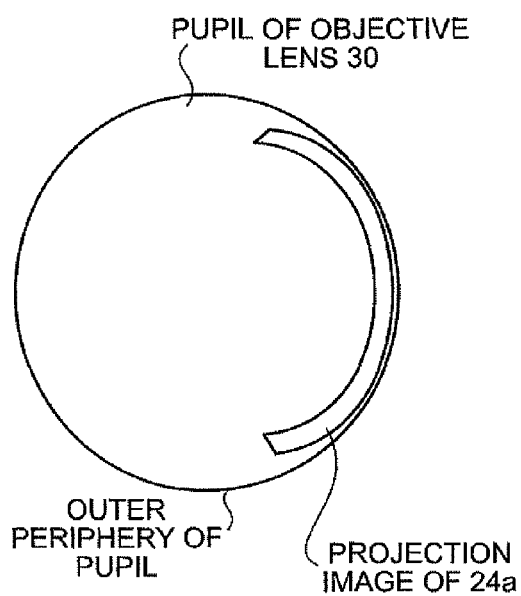
FIG. 15B is a view showing one example of a projection image of the aperture at the pupil of the objective lens 30.

An aperture unit 24 shown in FIG. 15A is detachably arranged at the pupil position of the condenser lens 23. FIGS. 15A and 15B are views showing the structure of the aperture unit 24 and one example of the projected image of an aperture at the pupil of the objective lens 30. The aperture unit 24 is composed of an aperture 24a of a partial annular zone and a light-shielding plate 24b having light shielding property. The aperture 24a is arranged relative to the optical axis so as to be decentered with respect to the center of the pupil, whereby the aperture 24a can freely laterally be shifted. The diameter of the aperture 24a is determined such that the projection image of the aperture 24a substantially touches internally the outer peripheral portion of the pupil of the objective lens 30 as shown in FIG. 15B. The width of the aperture 24a ("Ro-Ri" shown in FIG. 15A) is desirably not more than a third of the pupil radius of the objective lens 30 that is in conjugated relation. Thus, the moving amount of the objective lens 30 can appropriately be set depending upon the type of the living cell to be observed, whereby an image having the optimum contrast can be obtained.

Figure 16A:
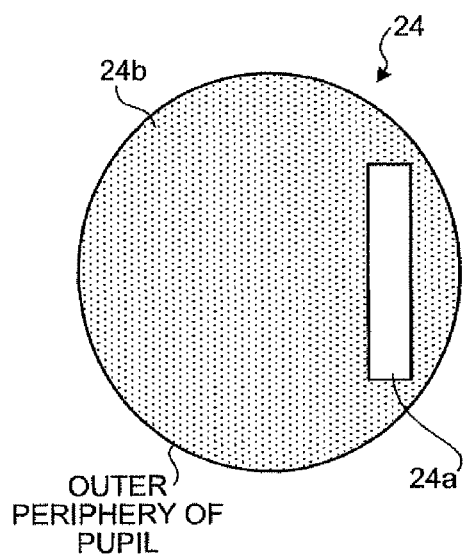
FIG. 16A is a view showing another configuration of an aperture unit 24.
Figure 16B:
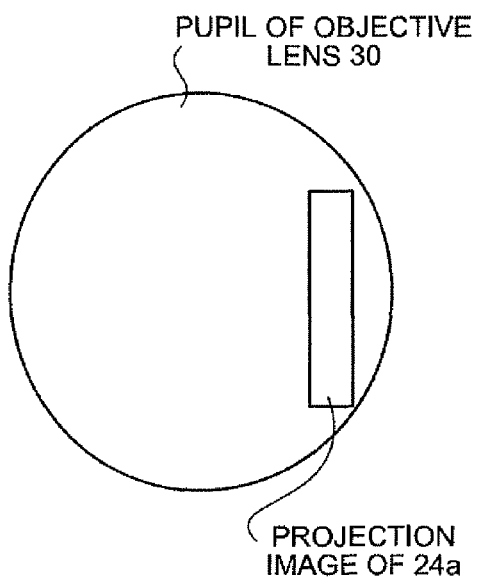
FIG. 16B is a view showing one example of a projection image of the aperture at the pupil of the objective lens 30.

The aperture unit 24 may be provided with a rectangular aperture 24a as shown in FIG. 16A. FIGS. 16A and 16B are views showing another example of the structure of the aperture unit 24 and the projection image of the aperture at the pupil of the objective lens 30. The rectangular aperture 24a is arranged at the position, apart from the central position of the pupil by a predetermined distance, as decentered relative to the center of the pupil. When the specimen 10 is obliquely illuminated with the use of the aperture unit 24 having the rectangular aperture 24a, the image of the aperture 24a is projected on the pupil of the objective lens 30. Since the rectangular aperture 24a is not arranged concentrically relative to the center of the pupil, an image having a high contrast can be obtained in a case where a living cell to be observed is long and slender. The oblique illumination light is incident on a living cell having a solid size, divided into transmitted light, refraction light and diffraction light, and emitted from the living cell. In the living cell, refraction light is greatly emitted from the portion that is the outline having a shape of approximately a sphere or ellipse, while transmitted light and diffraction light are greatly emitted from the flat portion. Some refraction lights refracted at the portion having the shape approximately a sphere or ellipse in the cell become greater than the NA of the objective lens 30, so that they are not taken into the objective lens 30.

Figure 17:
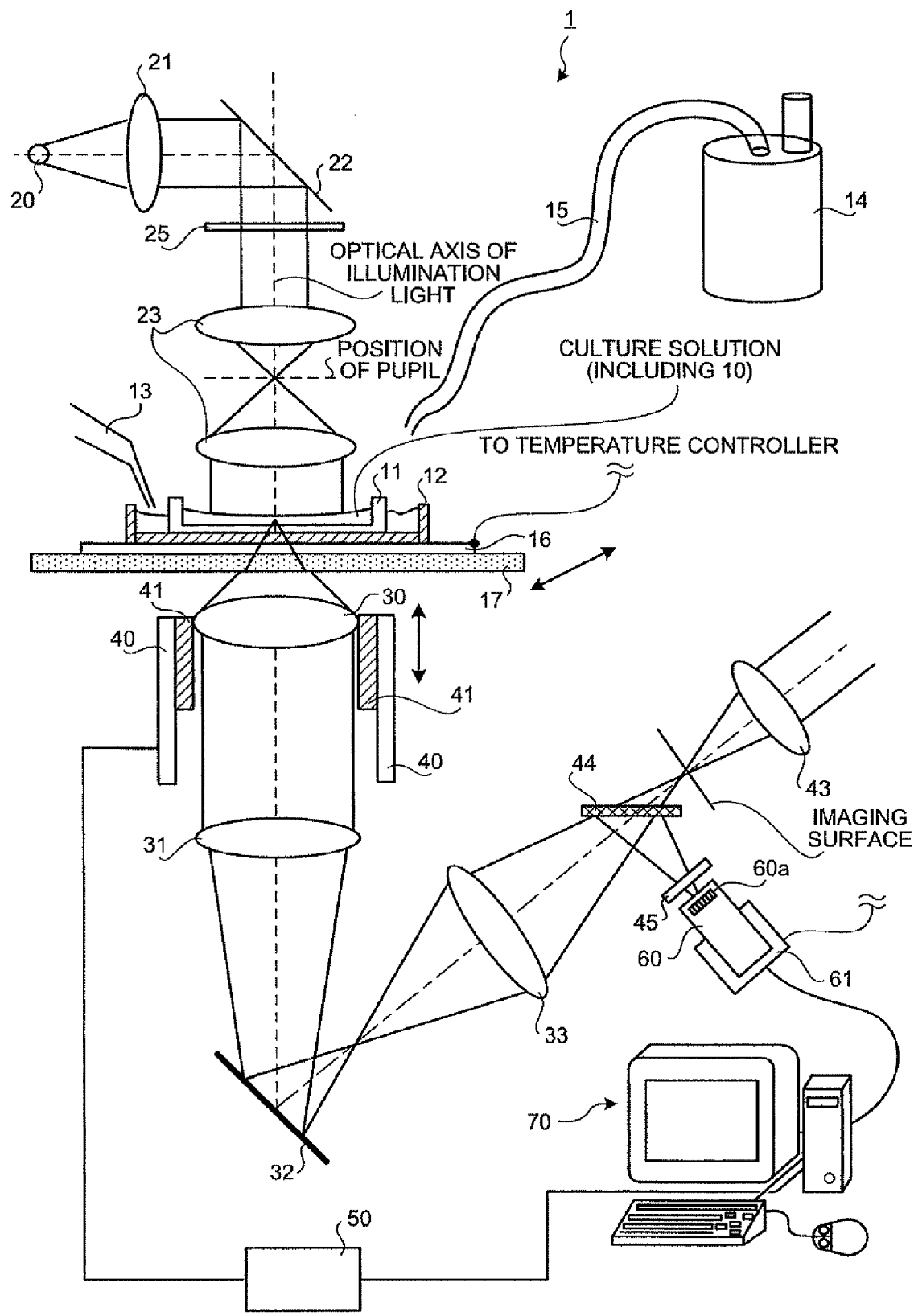
FIG. 17 is a view showing another specific example of the configuration of the focal position determining apparatus 1 according to the first embodiment.

As shown in FIG. 17, an interference filter 25 for providing the light source 20 having a quasi-monochromatic color may be arranged below the deflection mirror 22. With this structure, the illumination light emitted from the light source 20 is deflected by the deflection mirror 22, the deflected illumination light passes through the interference filter 25 to become a monochromatic light whose wavelength band width is extremely narrow, and then, directs toward the condenser lens 23. A narrow-band-pass filter may be employed instead of the interference filter.

Returning back to FIG. 13, the observation optical system is used for forming an image of the specimen 10, and arranged invertedly below the specimen stage 17. The observation optical system is composed of a relay lens 31 that images the image (image of the specimen 10) formed by the objective lens 30 on the imaging surface, a deflection mirror 32 that deflects the light from the objective lens 30, and a relay lens 33 that images the image (image of the specimen 10) formed by the objective lens 30 on the imaging surface with the relay lens 31, in addition to the objective lens 30.

The focal position changing unit 40 is specifically an objective lens z-axis moving (driving) mechanism that moves (drives) the objective lens 30 in the optical axis direction (z axis direction) by a rack-and-pinion mechanism (not shown). A knob included in the rack-and-pinion mechanism is rotated by a stepping motor (not shown) controlled by a computer. The objective lens z-axis moving mechanism may move the objective lens 30 in the optical axis direction by a friction roller mechanism instead of the rack-and-pinion mechanism. The focal position changing unit 40 may be configured to move the specimen stage 17 along the optical axis, instead of the structure in which the objective lens 30 is moved along the optical axis. As illustrated in the figure, an objective lens heater 41 is mounted in the objective lens z-axis moving mechanism.

The objective lens heater 41 is attached around the objective lens 30 as coming in contact with the objective lens 30 as illustrated in the figure. The objective lens heater 41 is controlled by a temperature adjusting device (not shown) connected to the objective lens heater 41. The objective lens heater 41 sets the temperature of the objective lens 30 from the outside of the objective lens 30 at 0.5° C. intervals so as to keep the temperature of the objective lens 30 constant.

The ocular lens 43 magnifies the image of the specimen 10. The ocular lens 43 is used for allowing an operator to visually observe the image of the specimen 10.

A switching mirror 44 is arranged between the ocular lens 43 and the relay lens 33 as shown in the figure. With this structure, the visual observation of the specimen 10 by the ocular lens 43 and the observation of the specimen 10 by the specimen imaging unit 60 can optionally be switched. In addition to the type of mechanically switching two optical paths, a type of separating two optical paths with the use of a half mirror may be employed as the switching mirror 44.

The infrared ray cut filter 45 is detachably mounted above the light-receiving surface of the specimen imaging unit 60 as shown in the figure for shielding infrared ray that becomes a background light. In other words, the infrared ray cut filter 45 prevents the infrared ray, which becomes the background light, from being incident on the specimen imaging unit 60, as needed.

The specimen imaging unit 60 is specifically a CCD camera having an imaging device 60a on its light-receiving surface. The pixel number of the imaging device 60a is 1360× 1024. The one having a sensitivity as high as possible is used for the CCD camera in order to be capable of detecting feeble light emitted from the specimen 10. A three-plate color camera may be used as the CCD camera in order to image a color bright-field image. The specimen imaging unit 60 is not limited to the CCD camera. For example, a CMOS (Complementary Metal Oxide Semiconductor) image sensor or SIT (Silicon Intensified Target) camera may be used as the specimen imaging unit 60. The specimen imaging unit 60 is connected to the information processing device 70 (a TV monitor connected to the information processing device 70) via a signal cable. A cooling device 61 is arranged at the bottom part of the specimen imaging unit 60 for preventing dark current emitted from the CCD camera.

The cooling device 61 is composed of a Peltier element for cooling the temperature of the specimen imaging unit 60 to 0° C. and keeping this temperature.

The information processing device 70 further has an input/output device (TV monitor, keyboard, mouse, etc.). The information processing device 70 describes the image imaged by the specimen imaging unit 60 on a TV monitor.

In the focal position determining apparatus 1 shown in FIG. 13, light emitted from the light irradiating unit 20 is firstly made into parallel light by the collector lens 21, and this parallel light is projected at the position of the pupil of the condenser lens 23. The image of the light emitted from the light irradiating unit 20 illuminates the specimen 10 by the condenser lens 23 as Koehler illumination. The light illuminating the specimen 10 transmits the specimen 10 to be incident on the objective lens 30. Then, the light (measurement light) incident on the objective lens 30 forms an image of the specimen 10 by the objective lens 30, the relay lens 31 and the relay lens 32 on the imaging surface. The image of the specimen 10 formed on the imaging surface is incident intact on the ocular lens 43 and is imaged on the imaging device 60a of the CCD camera 60 by the switching mirror 44.

The explanation of the focal position determining apparatus 1 according to the first embodiment is now ended here.

3. Process of Focal Position Determining Apparatus 1

Figure 18:
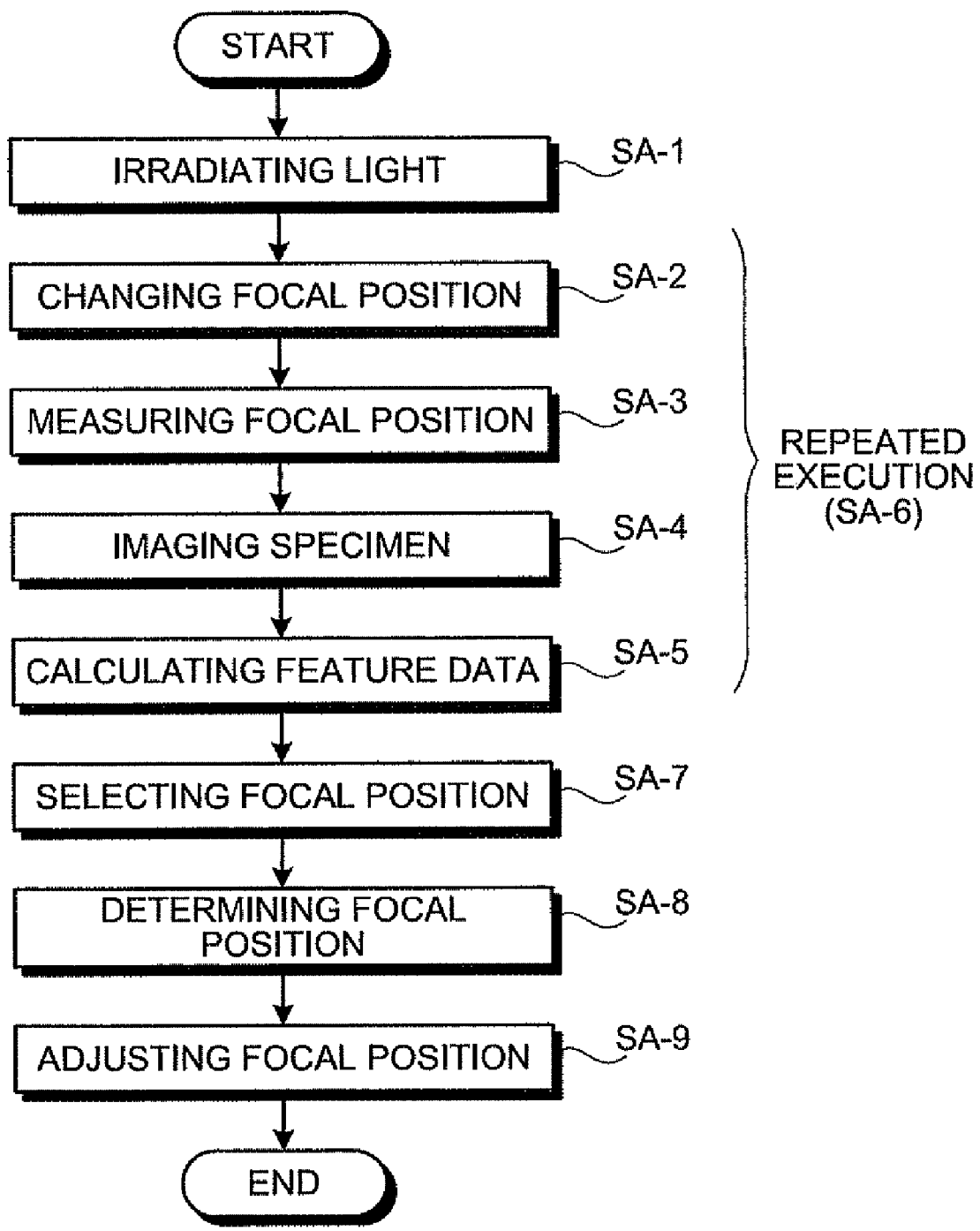
FIG. 18 is a flowchart showing one example of a focal position determining process executed by the focal position determining apparatus 1 according to the first embodiment.

Next, the focal position determining process executed by the focal position determining apparatus 1 according to the first embodiment will be explained with reference to FIG. 18. FIG. 18 is a flowchart showing one example of the focal position determining process executed by the focal position determining apparatus 1 according to the first embodiment. The focal position determining process in which a luminescence observation of a living cell is performed by using the focal position determining apparatus 1 shown in FIG. 13 will be explained here.

When an operator sets the specimen container 11 in which a living cell that is the specimen 10 is put on the specimen stage 17, and starts the focal position determining apparatus 1 and the light source 20, the focal position determining apparatus 1 performs the following process.

Firstly, the focal position determining apparatus 1 irradiates the illumination light emitted from the light source 20 to the living cell (step SA-1).

Next, the focal position determining apparatus 1 operates the objective lens z-axis moving mechanism, which is the focal position changing unit 40, by the control unit 70a of the information processing device 70, so as to move the objective lens 30 from the initial position along the optical axis by a predetermined amount by the objective lens z-axis moving mechanism. Therefore, the focal position of the objective lens 30 is changed (step SA-2).

Then, the focal position determining apparatus 1 operates the focal position measuring unit 50 by the control unit 70a of the information processing device 70 so as to measure the focal position of the objective lens 30 by the focal position measuring unit 50 (step SA-3).

Next, the focal position determining apparatus 1 operates the CCD camera, which is the specimen imaging unit 60, by the control unit 70a of the information processing device 70 so as to image the living cell by the CCD camera (step SA-4).

Then, the focal position determining apparatus 1 operates the feature data calculating unit 70a1 by the control unit 70a of the information processing device 70 so as to calculate a contrast of the imaged image by the feature data calculating unit 70a1 based on the image imaged at the step SA-4 (step SA-5).

The focal position determining apparatus 1 stores the focal position measured at the step SA-3, the image imaged at the step SA-4 and the contrast calculated at the step SA-5 in the imaged image database 70b1 of the storage unit 70b, as associated with one another, by the control unit 70a of the information processing device 70.

Next, the focal position determining apparatus 1 repeatedly executes the processes from the step SA-2 to the step SA-5 by the control unit 70a of the information processing device 70, until the focal position of the objective lens 30 that is changed at the step SA-2 exceeds the predetermined position on the optical axis (step SA-6).

Then, the focal position determining apparatus 1 operates the focal position selector 70a2 by the control unit 70a of the information processing device 70 so as to select two contrasts, among the plural contrasts stored in the imaged image database 70b1, which are the maximum, and acquires the focal position stored in the imaged image database 70b1 as associated with the selected contrast by the focal position selector 70a2 (step SA-7). In other words, the focal position determining apparatus 1 selects the focal position (substantial focal position) at the near point of the objective lens 30 and the focal position (substantial focal position) at the far point of the objective lens 30 from the plural focal positions stored in the imaged image database 70b1 based on the plural feature data stored in the imaged image database 70b1 by the focal position selector 70a2.

Then, the focal position determining apparatus 1 operates the focal position determining unit 70a3 by the control unit 70a of the information processing device 70 so as to determine the central position (the position at the approximate center) between two focal positions as the focal position of the objective lens 30 focused on the observed target region 10a in the living cell by the focal position determining unit 70a3 based on the two focal positions selected at the step SA-7 (step SA-8).

Next, the focal position determining apparatus 1 operates the objective lens z-axis moving mechanism by the control unit 70a of the information processing device 70 so as to adjust the position of the objective lens 30 by the objective lens z-axis moving mechanism in such a manner that the focal position of the objective lens 30 is focused on the central position (the position at the approximate center) determined at the step SA-8 (step SA-9).

As explained above, the focal position determining apparatus 1 according to the first embodiment irradiates illumination light to the living cell from the light source 20. Then, the focal position determining apparatus 1 repeatedly moves the objective lens 30 along the optical axis by a predetermined amount by the objective lens z-axis moving mechanism, and every time the objective lens 30 is moved, it measures the focal position of the objective lens 30 by the focal position measuring unit 50. The focal position determining apparatus 1 illuminates and images the living cell by the CCD camera, and calculates the contrast of the imaged image by the feature data calculating unit 70a1. The focal position determining apparatus 1 then selects two maximum contrasts, among the accumulated plural contrasts obtained by repeatedly moving the objective lens 30, by the focal position selector 70a2, and acquires the focal positions of the objective lens 30 when the images corresponding to the selected contrasts are imaged from the accumulated plural focal positions obtained by repeatedly moving the objective lens 30. Then, the focal position determining apparatus 1 determines, by the focal position determining unit 70a3, the central position (the position at the approximate center) between two focal positions as the focal position of the objective lens 30 focused on the observed target region 10a in the living cell, and moves the objective lens 30 by the objective lens z-axis moving mechanism so as to adjust the focal position of the objective lens 30 to the determined focal position. Accordingly, when the specific region in the living cell is defined as the observed target region 10a and the luminescent observation of the observed target region 10a is performed, the focal position of the objective lens 30 focused on the observed target region 10a can be determined at the time of setting the living cell, with the result that the focal position of the objective lens 30 can be focused on the observed target region 10a. Specifically, according to the focal position determining apparatus 1, the objective lens can automatically be focused on a luminescent region (a region where a bioluminescent protein is located) in a living cell without confirming the luminescence from the living cell, in a microscope that observes a living cell, which emits feeble light, with the use of magnification imaging optical means including a lens, measures luminescence from the living cell, or observes feeble luminescence from a bioluminescent protein in the living cell, for example. Accordingly, when a specimen emitting feeble light is observed with the use of magnification imaging optical means including a lens, the focal position of the objective lens can quickly and precisely be set to the target region in the specimen, compared to the manual setting. The focal position determining apparatus 1 employs an illumination image of a specimen for determining the focal position of the objective lens. This illumination image is bright and has a high contrast. Therefore, compared to the case in which the focal position of the objective lens 30 focused on the observed target region 10a in the specimen 10 is visually set, the focal position of the objective lens 30 focused on the observed target region 10a in the specimen 10 can easily and quickly be determined. Further, in the focal position determining apparatus 1, the focal positions of the objective lens 30 when the illumination image of the specimen 10 with high contrast is imaged correspond to the substantial upper and lower peripheral edge portions of the specimen 10, the central position (substantial central position) between them may be determined as the focal position of the objective lens 30 focused on the observed target region 10a in the specimen 10. Thus, the focal position of the objective lens 30 focused on the observed target region 10a in the specimen 10 can easily and simply be determined.

Since the intensity of luminescence from a living body (living cell, or the like) is extremely feeble at the time of setting the specimen when a luminescent phenomenon of the living body is measured, the feeble light cannot be detected even by a high-performance CCD camera. Specifically, the objective lens cannot be focused while confirming the observed target region (cell, or the like) in the living body like an ordinary microscopic observation. In other words, an internal structure of a living body cannot be observed at the time of setting the living body, When regions where bioluminescent protein is localized in cell (that emit feeble light) are simultaneously observed in both cells by a microscope that is used for the observation of fluorescence or luminescence (chemiluminescence or bioluminescence), the objective lens is not focused on the luminescent region of the luminescent protein localized in the cell at the focal position of the objective lens detected based on the illumination image of the phase object such as a cell, so that the observation image may be blurred. In the fluorescent observation, the position where the fluorescent intensity is the greatest in the phase object emitting fluorescence by fluorescent exciting light is determined as the focal position. In this determination method, it is necessary to reduce the number of times of the determination of the focal position as much as possible, since the phototoxicity caused by the exciting light is strong, and it is undesirable to repeatedly determine the focal position to the specimen such as a living cell having bioactivity. However, when the number of times of the determination of the focal position is reduced in a long-term fluorescent observation, the resolution of the observation image might be unstable. In view of this, in the focal position determining apparatus 1, light emitted from the light source 20, such as a halogen lamp, is irradiated to a living body so as to acquire an illumination image of the living body by a microscope, and the focal position of the objective lens 30 is determined based on the acquired illumination image as an image observation by illumination light. Specifically, a living cell is imaged under illumination for estimating the position of the inside of the living cell. Accordingly, the internal structure of the living body can be observed at the time of setting the living body. Further, when regions (that emit feeble light) where bioluminescent protein is localized in a cell are simultaneously observed in both cells, the objective lens can be focused on the luminescent region of the bioluminescent protein localized in the cell. Further, the focal position determining apparatus 1 does not determine the focal position of the objective lens by using fluorescence, a long-term fluorescent observation can be carried out.

The focal position determining apparatus 1 may select the focal position of the objective lens 30 at the near point (the focal position of the objective lens 30 when an imaged image having a high contrast is obtained at the near point of the objective lens 30) by the focal position selector 70a2 from the plural focal positions stored in the imaged image database 70b1 based on the plural feature data stored in the imaged image database 70b1 at the step SA-7, and may determine, by the focal position determining unit 70a3, the position apart upwardly of the optical axis from the selected focal position of the objective lens 30 at the near point by a distance a half the thickness of the living cell that has already been measured as the focal position of the objective lens 30 focused on the observed target region 10a in the living cell at the step SA-8. In other words, the focal position determining apparatus 1 may select the focal position of the objective lens 30 at the near point when an image having a high contrast is obtained in the observation under illumination, and determine the position apart upwardly of the optical axis from the selected focal position by a distance a half the thickness of the living cell as the focal position of the objective lens 30 focused on the observed target region 10a in the living cell. The focal position determining apparatus 1 may select the focal position of the objective lens 30 at the far point (the focal position of the objective lens 30 when an imaged image having a high contrast is obtained at the far point of the objective lens 30) by the focal position selector 70a2 from the plural focal positions stored in the imaged image database 70b1 based on the plural feature data stored in the imaged image database 70b1 at the step SA-7, and may determine, by the focal position determining unit 70a3, the position apart downwardly of the optical axis from the selected focal position of the objective lens 30 at the far point by a distance a half the thickness of the living cell that has already been measured as the focal position of the objective lens 30 focused on the observed target region 10a in the living cell at the step SA-8. In other words, the focal position determining apparatus 1 may select the focal position of the objective lens 30 at the far point when an image having a high contrast is obtained in the observation under illumination, and determine the position apart downwardly of the optical axis from the selected focal position by a distance a half the thickness of the living cell as the focal position of the objective lens 30 focused on the observed target region 10a in the living cell. Thus, compared to the case in which the objective lens 30 or the specimen 10 is moved to select the defocus position at the near point and at the far point, the focal position of the objective lens focused on the observed target region 10a in the specimen 10 can easily and simply be determined.

The focal position determining apparatus 1 may execute a step 1 to a step 6 described below so as to determine the focal position of the objective lens 30 focused on the observed target region 10a in a living cell arranged in the specimen container 11.

(Step 1) The power of the light source 20 is turned on, and the shutter of the light source 20 is opened and closed to irradiate illumination light from above the specimen container 11.

(Step 2) The focal position (corresponding to "Zd" in FIG. 14) of the objective lens 30 focused on the bottom surface (outer bottom surface or inner bottom surface) of the specimen container 11 is determined. Specifically, the objective lens 30 is moved along the optical axis by the objective lens z-axis moving mechanism by a predetermined amount, and every time the objective lens 30 is moved by the predetermined amount, the living cell is imaged under the illumination by the CCD camera. The integrated value (intensity of the output signal from the CCD camera) of the light intensity from all pixels of the imaged image is calculated by the feature data calculating unit 70a1. The control unit 70a confirms whether the calculated integrated value is the maximum value or not. When the calculated integrated value is confirmed to be the maximum value, it is considered that the objective lens 30 is focused on the bottom surface of the specimen container 11 when the imaged image, which is the original of the maximum value, is imaged, so that the focal position (corresponding to "Zd" in FIG. 14) of the objective lens 30 at the time of imaging is measured by the focal position measuring unit 50. Specifically, the maximum value of the reflection light from the bottom surface of the specimen container 11 is determined with the illumination image, while moving the objective lens 30 along the optical axis.

(Step 3) The focal position (corresponding to "Zc" in FIG. 14) of the objective lens 30 when the image having a high contrast is imaged is determined at the near point of the objective lens 30. Specifically, the objective lens 30 is further moved from the position where the objective lens is moved at the (step 2) along the optical axis by a predetermined amount by the objective lens z-axis moving mechanism, and every time the objective lens 30 is moved by the predetermined amount, the living cell is imaged under the illumination by the CCD camera. The contrast of the imaged image is calculated by the feature data calculating unit 70a1, and the control unit 70a confirms whether the calculated contrast is the maximum value or not. When it is confirmed that the calculated contrast is the maximum value, it is considered that the objective lens 30 is focused on the substantial lower end surface of the living cell when the imaged image, which is the original of the maximum value, is imaged, so that the focal position (corresponding to "Zc" in FIG. 14) of the objective lens 30 at the time of imaging is measured by the focal position measuring unit 50.

(Step 4) The focal position (corresponding to "Za" in FIG. 14) of the objective lens 30 when the image having a high contrast is imaged is determined at the far point of the objective lens 30. Specifically, the objective lens 30 is further moved from the position where the objective lens is moved at the (step 3) along the optical axis by a predetermined amount by the objective lens z-axis moving mechanism, and every time the objective lens 30 is moved by the predetermined amount, the living cell is imaged under the illumination by the CCD camera. The contrast of the imaged image is calculated by the feature data calculating unit 70a1, and the control unit 70a confirms whether the calculated contrast is the maximum value or not. When it is confirmed that the calculated contrast is the maximum value, it is considered that the objective lens 30 is focused on the substantial upper end surface of the living cell when the imaged image, which is the original of the maximum value, is imaged, so that the focal position (corresponding to "Za" in FIG. 14) of the objective lens 30 at the time of imaging is measured by the focal position measuring unit 50.

(Step 5) The position (e.g., corresponding to "Zb((Zc+Za)÷2)" in FIG. 14) at approximately the center between the focal position (corresponding to "Zc" in FIG. 14) determined at the (step 3) and the focal position (corresponding to "Za" in FIG. 14) determined at the (step 4) is determined as the focal position of the objective lens 30 focused on the observed target region 10a in the living cell.

(Step 6) The objective lens 30 is moved such that the focal position of the objective lens 30 is adjusted to the central position determined at the (step 5).

The focal position of the objective lens 30 corresponding to "Zc" or "Za" in FIG. 14 may be determined at the step 4 and the step 5 as described below. Specifically, every time the objective lens 30 is moved by a predetermined amount, the living cell is imaged under the illumination by the CCD camera, and the focal position of the objective lens 30 at the time of the imaging is measured. The contrasts (sum of the output signals from each pixel of the plural imaged images) of the plural imaged images taken as moving the objective lens 30 are calculated. The calculated contrasts (sum) are compared to one another so as to select the maximum contrast (sum), and the focal position of the objective lens 30 when the imaged image corresponding to the selected contrast (sum) is imaged is selected from the plural focal positions of the objective lens 30 measured as moving the objective lens 30, whereby the focal position of the objective lens 30 corresponding to "Zc" or "Za" in FIG. 14 is determined. The focal position determining apparatus 1 may be provided with a photodiode instead of the CCD camera. In this case, at the step 4 and the step 5, every time the objective lens 30 is moved by a predetermined amount, the output current of the photodiode may be amplified and converted into a voltage signal, as well as the focal position of the objective lens 30 may be measured. The intensities of the plural voltage signals converted as moving the objective lens 30 may be compared to one another so as to select the intensity of the maximum voltage signal. The focal position of the objective lens 30 corresponding to the intensity of the selected voltage signal may be selected from the plural focal positions of the objective lens 30 measured as moving the objective lens 30, whereby the focal position of the objective lens 30 corresponding to "Zc" or "Za" in FIG. 14 may be determined. In the focal position determining apparatus 1, the amount (moving amount) for moving the objective lens 30 or the specimen 10 is desirably within the range with which the image taken by the CCD camera is not blurred. Specifically, the moving amount is desirably not more than the value ($\lambda \div NA^2$: $\lambda$ is a wavelength, NA is a numerical aperture) obtained by dividing the wavelength of the light emitted from the light source 20 by the square of NA of the objective lens 30.

The focal position determining apparatus 1 may employ, as the light source 20, a light source (such as a laser) having high monochromaticity. When the monochromaticity of the light source is high, little wavelength distribution appears when illumination light is irradiated to the phase object, whereby a sharp diffraction light can be obtained. Therefore, the contrast of the image imaged at the near point and the contrast of the image imaged at the far point become extremely high compared to the case of using white light source. Accordingly, the focal position of the objective lens when the image having the maximum contrast is imaged can easily be selected.

In the focal position determining apparatus 1, an operator may visually determine two positions of the objective lens where the contrast of the image of the living cell becomes high through the ocular lens 43 while manually turning the knob of the objective lens z-axis moving mechanism, the determined focal position of the objective lens may be measured by the focal position measuring unit 50, and the central position (substantial central position) between the measured two focal positions may be determined as the focal position of the objective lens focused on the observed target region 10*a* in the living cell by the focal position determining unit 70*a*3.

According to the focal position determining apparatus 1, the position of the objective lens 30 is moved in the forward direction or rearward direction by a slight amount relative to the specimen 10 from the focusing position in an ordinary observation, whereby an image having a contrast same as that in the phase contrast observation can be obtained without using an objective lens for a phase contrast. Further, according to the focal position determining apparatus 1, it is unnecessary to consider the pupil aberration between the objective lens 30 and the condenser lens 23, whereby an objective lens having a low magnification can be used. Specifically, according to the focal position determining apparatus 1, a phase object such as a cultured cell can be observed even by using an objective lens at ×1 or ×2 magnification that cannot be used in the phase contrast observation. Therefore, an observation in a wide range, which cannot be realized in a conventional observation method, can be performed. According to the focal position determining apparatus 1, an image having a high contrast and a relief-like texture in which the phase distribution is shaded can be obtained by oblique illumination. The focal position determining apparatus 1 can switch the visual observation and the observation by the TV monitor by the switching mirror 44. By using a half mirror as the switching mirror 44, the visual observation and the observation by the TV monitor can simultaneously be performed. When the aperture is removed, the focal position determining apparatus 1 can be employed as an ordinary microscope to observe a specimen. According to the focal position determining apparatus 1, the focal position of the objective lens 30 is determined in two steps, whereby a focal position can be determined even when an objective lens having a high magnification is used. Since the focal position determining apparatus 1 does not use exciting light, the focal position determining apparatus 1 has an advantage that there is little affect by phototoxicity even if the focal position determining process is repeatedly executed to a biological specimen emitting fluorescence. In other words, in a case where a living cell is continuously observed over time, a clear image can be continuously imaged by repeating the focal position determining process. When the focal position determining process is performed by using infrared ray in the focal position determining apparatus 1, the focal position of the objective lens is adjusted and further, a dark field image of a specimen can be imaged, while maintaining the state in which the illumination by visible light is not performed. Therefore, it can effectively be prevented that noise is caused on the imaged image due to self-luminescence.

Figure 19:
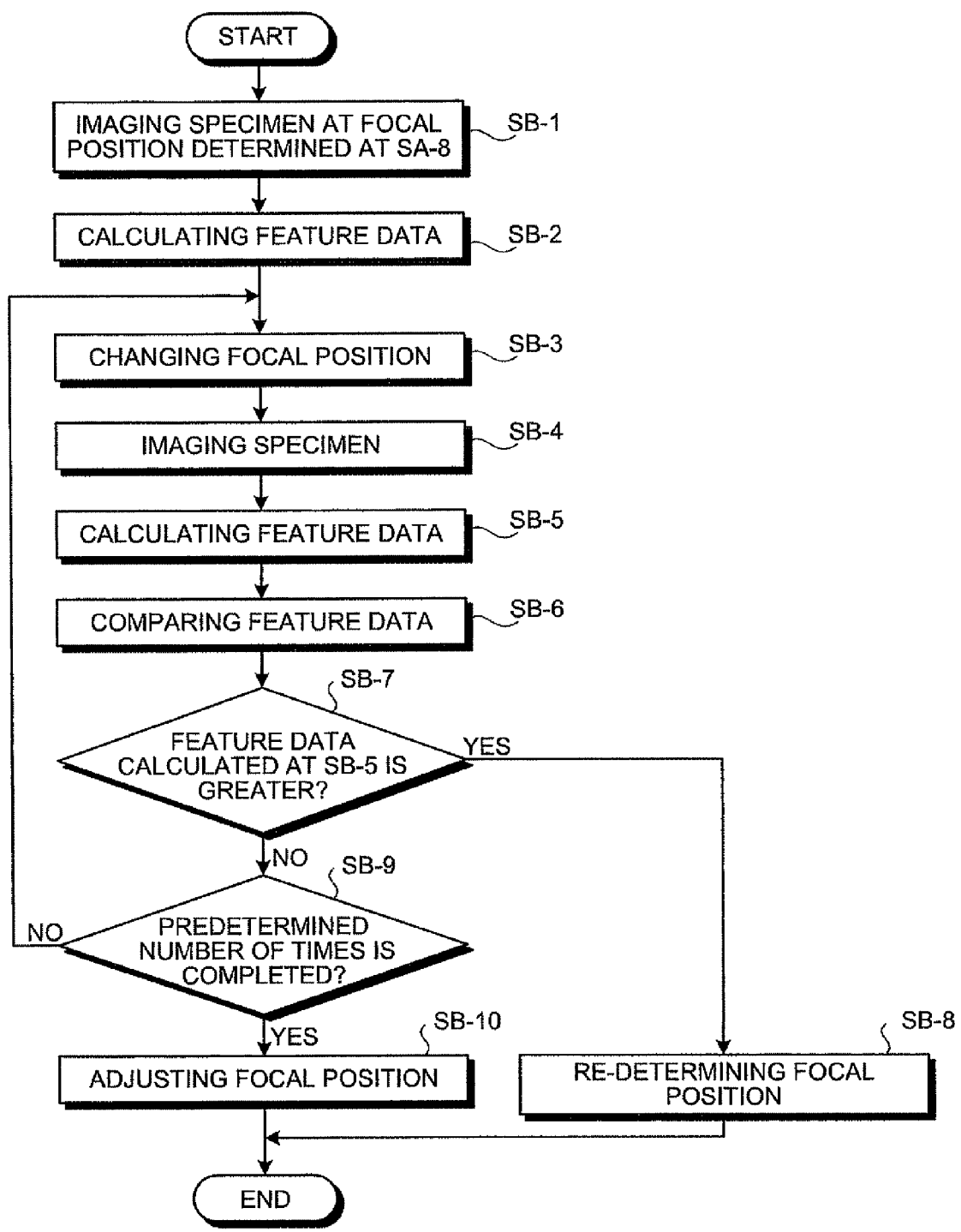
FIG. 19 is a flowchart showing one example of a focal position re-determining process executed by the focal position determining apparatus 1 according to the first embodiment.

When the intensity of the luminescence emitted from the specimen 10 is in the degree that can be detected by the CCD camera, the focal position determining apparatus 1 may re-determine the focal position of the objective lens focused on the observed target region 10*a* in the specimen 10, which focal position is determined at the time of setting the specimen 10 (focal position re-determining process). When the luminescence from the specimen 10 is observed by the objective lens 30 having high magnification (e.g., ×40 or more), the image of the specimen 10 is blurred unless the focal position of the objective lens 30 is accurately focused on the observed target region 10*a* in the specimen 10, since the focal depth becomes extremely shallow as the magnification of the objective lens 30 increases. Although the focal position determined by the aforesaid focal position determining process is focused on the approximate center of the specimen 10, it is necessary to determine the focal position of the objective lens 30 more precisely focused on the observed target region 10*a* in the specimen 10, when the luminescence from the specimen 10 is acquired with high precision. In view of this, the focal position re-determining process is executed, whereby the focal position of the objective lens focused on the observed target region 10*a* in the specimen 10 can be continuously determined not only at the time of setting the specimen 10 but also after the start of the luminescent observation of the specimen 10. As a result, the focal position of the objective lens can always be focused on the observed target region 10*a*. The focal position re-determining process executed by the focal position determining apparatus 1 will be explained with reference to FIG. 19. FIG. 19 is a flowchart showing one example of the focal position re-determining process executed by the focal position determining apparatus 1 according to the first embodiment.

Firstly, the focal position determining apparatus 1 operates the CCD camera by the control unit 70*a* so as to image the specimen 10 by the CCD camera without the illumination at the focal position (the focal position of the objective lens 30 determined at the step SA-8 in FIG. 18 and focused on the observed target region 10*a* in the specimen 10) determined by the focal position determining unit 70*a*3 (step SB-1).

Then, the focal position determining apparatus 1 operates the feature data calculating unit 70*a*1 by the control unit 70*a* so as to calculate feature data (e.g., luminescent intensity from each pixel of the luminescent image, statistical amount obtained from the luminescent intensity distribution of the luminescent image, contrast of the luminescent image) by the feature data calculating unit 70*a*1 based on the image (luminescent image) imaged at the step SB-1 (step SB-2).

Next, the focal position determining apparatus 1 operates the objective lens z-axis moving mechanism by the control unit 70*a* so as to move the objective lens 30 by the objective lens z-axis moving mechanism along the optical axis by a predetermined amount, thereby changing the focal position determined by the focal position determining unit 70*a*3 (step SB-3). The focal position may be changed not only by moving the objective lens 30 but also by moving the specimen stage 17.

Then, the focal position determining apparatus 1 operates the CCD camera by the control unit 70*a* so as to image by the CCD camera the specimen 10 without the illumination at the focal position changed at the step SB-3 (step SB-4).

Next, the focal position determining apparatus 1 operates the feature data calculating unit 70*a*1 by the control unit 70*a* so as to calculate feature data (e.g., luminescent intensity from each pixel of the luminescent image, statistical amount obtained from the luminescent intensity distribution of the luminescent image, contrast of the luminescent image) by the feature data calculating unit 70*a*1 based on the image (luminescent image) imaged at the step SB-4 (step SB-5).

Then, the focal position determining apparatus 1 operates the feature data comparing unit 70*a*4 by the control unit 70*a* so as to compare the feature data calculated at the step SB-2 and the feature data calculated at the step SB-5 by the feature data comparing unit 70*a*4 (step SB-6). In the comparison of the feature data, there may be the case in which the feature data are appropriately compared by a contrast or the case in which the feature data are appropriately compared by the statistical amount obtained from the distribution of the luminescent intensity depending upon the type or property of the specimen 10, but finally, the feature data are compared by an S/N (signal-to-noise ratio).

Next, when the feature data calculated at the step SB-5 is greater as a result of the comparison at the step SB-6 (step SB-7: Yes), the focal position determining apparatus 1 operates the focal position determining unit 70*a*5 by the control unit 70*a* so as to determine the focal position changed at the step SB-3 as the focal position of the objective lens focused on the observed target region 10*a* in the living cell by the focal position determining unit 70*a*5 (step SB-8).

On the other hand, when the feature data calculated at the step SB-5 is not greater as a result of the comparison at the step SB-6 (step SB-1: No), the focal position determining apparatus 1 confirms, by the control unit 70*a*, whether or not the number of times of the execution at the step SB-3 reaches the predetermined number of times (whether or not the moving amount of the objective lens 30 at the step SB-3 reaches the predetermined amount). When it reaches the predetermined number of times (step SB-9: Yes), the focal position determining apparatus 1 operates the objective lens z-axis moving mechanism by the control unit 70*a* so as to return the focal position of the objective lens 30 changed at the step SB-3 to the focal position determined at the beginning by the focal position determining unit 70*a*3 (the focal position of the objective lens 30 determined at the step SA-8 in FIG. 18 and focused on the observed target region 10*a* in the living cell) (step SB-10). When the number of times of the execution does not reach the predetermined number of times (step SB-9: No), the focal position determining apparatus 1 returns to the process at the step SB-3 by the control unit 70*a*.

The explanation of the focal position determining apparatus 1 according to the first embodiment is now ended.

Second Embodiment

Next, the structure of the focal position determining apparatus 1 according to the second embodiment will be explained in detail with reference to FIGS. 20 to 22. The explanation of the parts overlapped with those in the first embodiment may sometimes be omitted.

Figure 20:
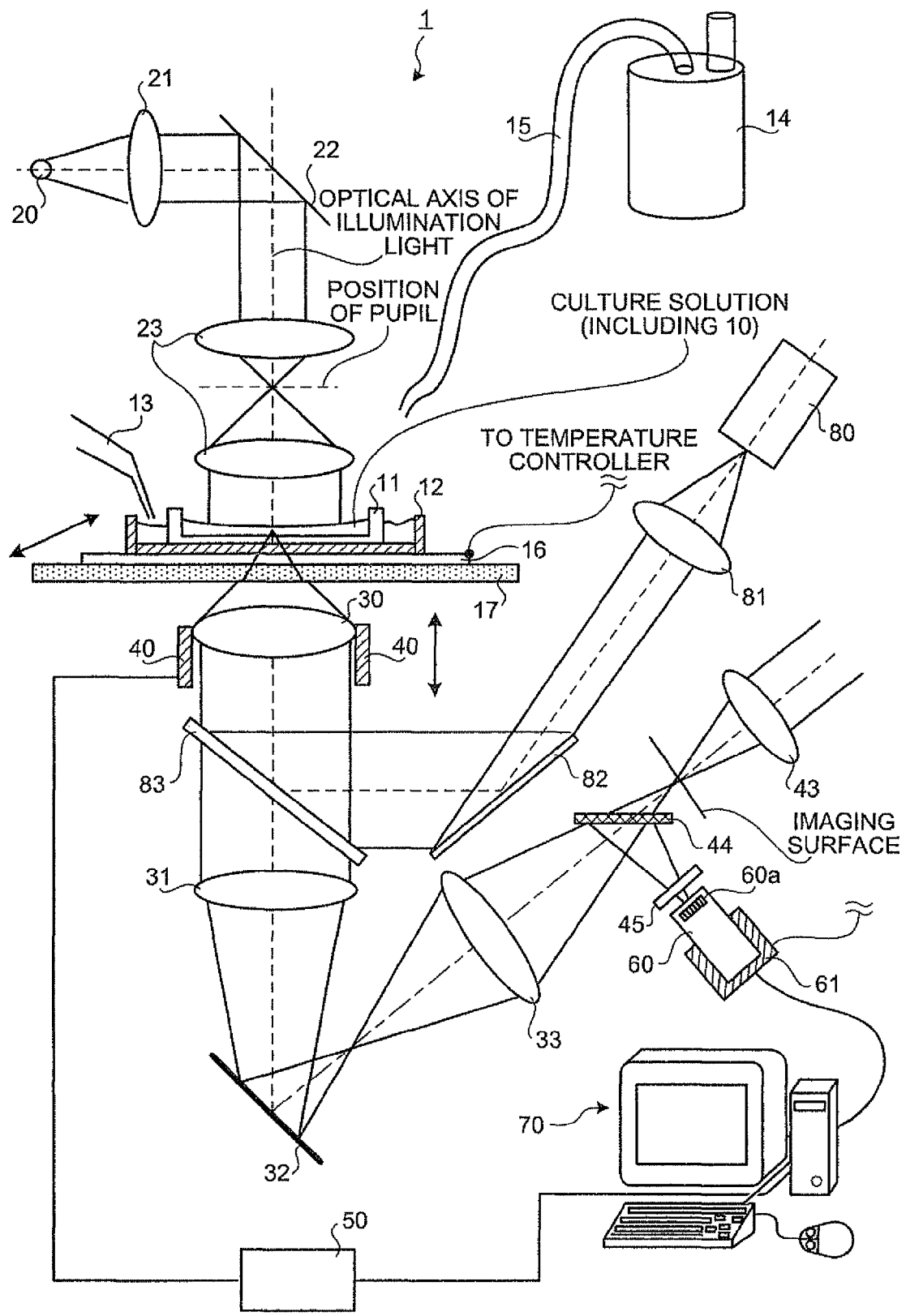
FIG. 20 is a view showing a specific example of the configuration of the focal position determining apparatus 1 according to a second embodiment.

FIG. 20 is a view showing one specific example of the structure of the focal position determining apparatus 1 according to the second embodiment. The focal position determining apparatus 1 shown in FIG. 20 has a structure with an inverted microscope as a base, and is used for observing simultaneously luminescence and fluorescence of a living cell that emits feeble light. In simultaneously observing fluorescence and luminescence, the focal position determining apparatus 1 determines the focal position of the objective lens 30 focused on the observed target region 10*a* in the specimen 10 at the time of setting the specimen 10 such as a living cell or tissue. As shown in FIG. 20, the focal position determining apparatus 1 has an exciting optical system including an exciting light irradiating unit (exciting light source) 80, a collimator lens 81, a deflection mirror 82 and a dichroic mirror 83.

When the specimen 10 is present in the air (when the specimen 10 is not immersed into liquid such as culture solution), the focal position determining apparatus 1 shown in FIG. 20 employs the objective lens 30 having the numerical aperture (NA) of about 0.9, while when the specimen 10 is immersed into liquid, it employs the objective lens having the numerical aperture of not less than 1.0. The specimen 10 is dyed beforehand with Rohdamine Green (RhG) that is a fluorescent pigment (fluorescent material). Instead of Rhodamine Green, usable fluorescent materials include TMR (Tetramethylrhodamine), 5-Tamra (5-carboxytetramethylrhodamine), FITC (Fluorescein-i-sothiocyanate), TOTO1, Acridine-Orange, Texas-Red, etc.

The exciting light irradiating unit 80 is a gas laser (e.g., argon laser, helium-neon laser (He.Ne laser), etc.) emitting laser beam having a wavelength in a visible light region. Specifically, the exciting light irradiating unit 80 is an argon laser having a wavelength of 488 nm and output of 10 mW. When the specimen 10 is dyed with TMR that is a fluorescent material, the argon laser having a wavelength of 514.5 nm is used as the exciting light irradiating unit 80 in order to excite the TMR. When the specimen 10 is dyed with 5-Tamra that is a fluorescent material, the He.Ne laser having a wavelength of 543.5 nm is used as the exciting light irradiating unit 80 in order to excite the 5-Tamra.

The collimator lens 81 converts the laser beam emitted from the exciting light irradiating unit 80 into annular parallel flux having a beam width.

The deflection mirror 82 deflects the optical axis of the laser beam, which is converted into the parallel flux by the collimator lens 81.

The dichroic mirror 83 is specifically a switching dichroic mirror, and introduces the laser beam deflected by the deflection mirror 82 to the objective lens 30. The switching dichroic mirror has a spectral characteristic of reflecting light having an oscillation wavelength of the exciting light source 80 and transmitting the spectrum of the fluorescent signal and the luminescent signal. The dichroic mirror 83 is housed in a holder (not shown), so that it is replaceably arranged according to the oscillation wavelength of the laser beam. If it is unnecessary to change the wavelength of the laser beam emitted from the exciting light irradiating unit 80, an ordinary dichroic mirror, not the switching dichroic mirror, may be used as the dichroic mirror 83.

In the focal position determining apparatus 1 shown in FIG. 20, the fluorescence and luminescence emitted from the specimen 10 reaches the dichroic mirror 83 through the objective lens 30. The fluorescence and luminescence having reached the dichroic mirror 83 transmits the dichroic mirror 83, and are reflected by the switching mirror 44 through the relay lens 31 and the relay lens 33 to be focused on the imaging device 60a on the light-receiving surface of the CCD camera 60. When the switching mirror 44 is removed from the optical path, the fluorescence and luminescence emitted from the specimen 10 reaches the ocular lens 43. Accordingly, an operator can directly observe the image of the specimen 10.

Next, another specific example of the focal position determining apparatus 1 according to the second embodiment will be explained in detail with reference to FIG. 21. FIG. 21 is a view showing another specific example of the focal position determining apparatus 1 according to the second embodiment.

Figure 21:
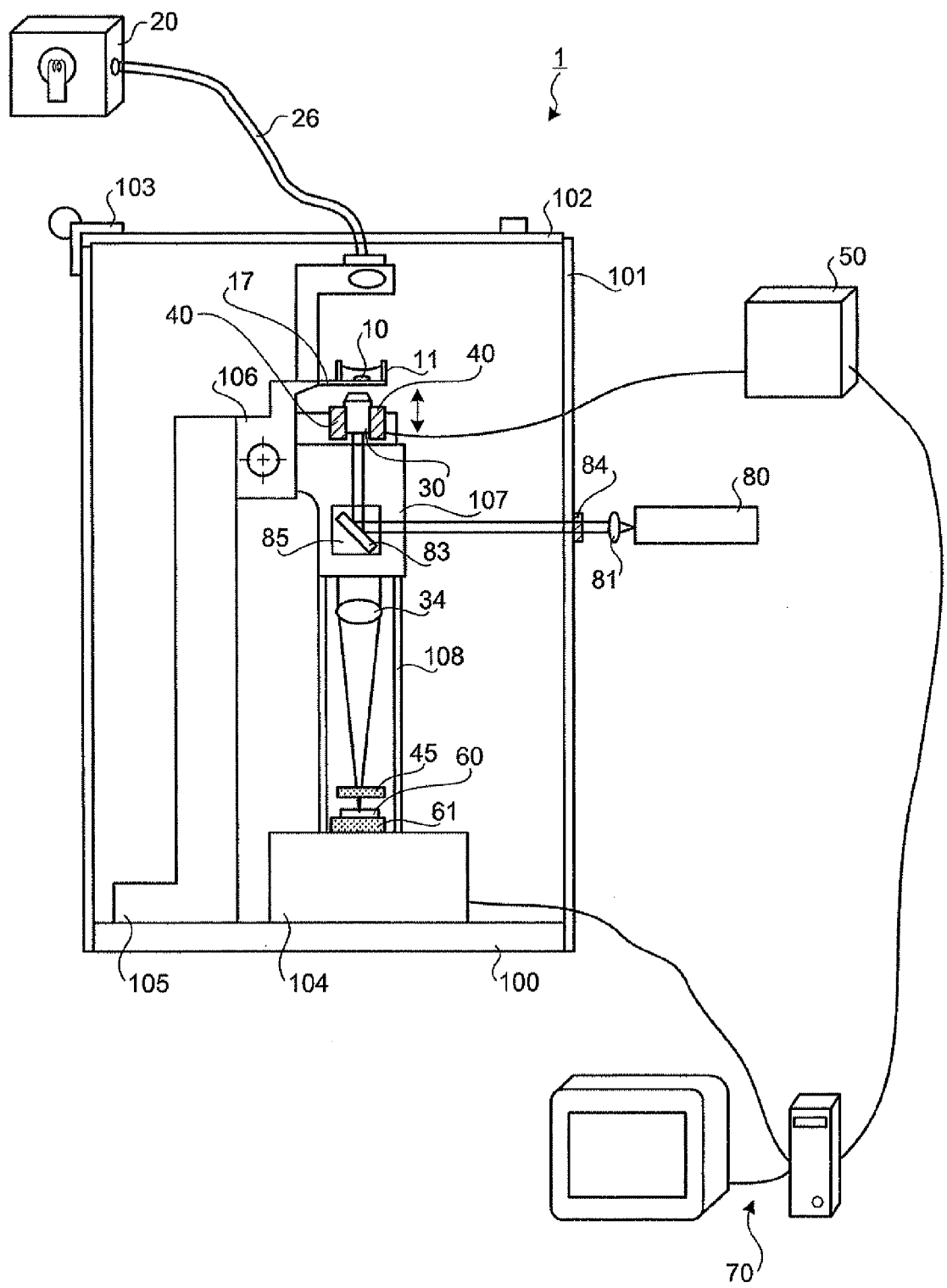
FIG. 21 is a view showing another specific example of the configuration of the focal position determining apparatus 1 according to the second embodiment.

As shown in FIG. 21, the main body (portion of the optical system) of the focal position determining apparatus 1 is fixed on a main body rack 106. The main body rack 106 is vertically movable. The main body rack 106 is attached to a column 105. The column 105 is fixed on a bottom plate 100. The observation optical system and the CCD camera 60, etc. in the focal position determining apparatus 1 are housed in a lens barrel. The lens barrel is composed of a lens barrel upper part 107 and a lens barrel tower part 108 connected to the lens barrel upper part 107. The lens barrel upper part 107 is fixed to the main body rack 106. The lens barrel lower part 108 is fixed to a base rack 104. The lens barrel is attached so as to be vertically movable. The base rack 104 is fixed on the bottom plate 100. The main body of the focal position determining apparatus 1 is enclosed by a light-shielding box 101 having light shielding property. The light-shielding box 101 is fixed to the bottom plate 100. A light-shielding lid 102 is mounted to the upper surface of the light-shielding box 101. One end of the light-shielding lid 102 is coupled to the light-shielding box 101 with a hinge 103 in order to make the lid openable and closable.

The specimen container 11 having the specimen 10 put therein is set on the specimen stage 17. As shown in FIG. 22, the specimen container 11 may be put into a water tank 12 to be set on the specimen stage 17.

Returning back to FIG. 21, a halogen lamp, metal halide lamp or the like is used as the light irradiating unit 20. Light emitted from the light irradiating unit 20 is irradiated to the specimen container 11 containing the specimen 10 on the specimen stage 17 through an optical fiber 26.

In the observation optical system, the deflection mirror 32 is not used, and instead, a relay lens 34 for imaging the image (image of the specimen 10) formed by the objective lens 30 is arranged at the lens barrel lower part 108 as shown in the figure.

Figure 22:
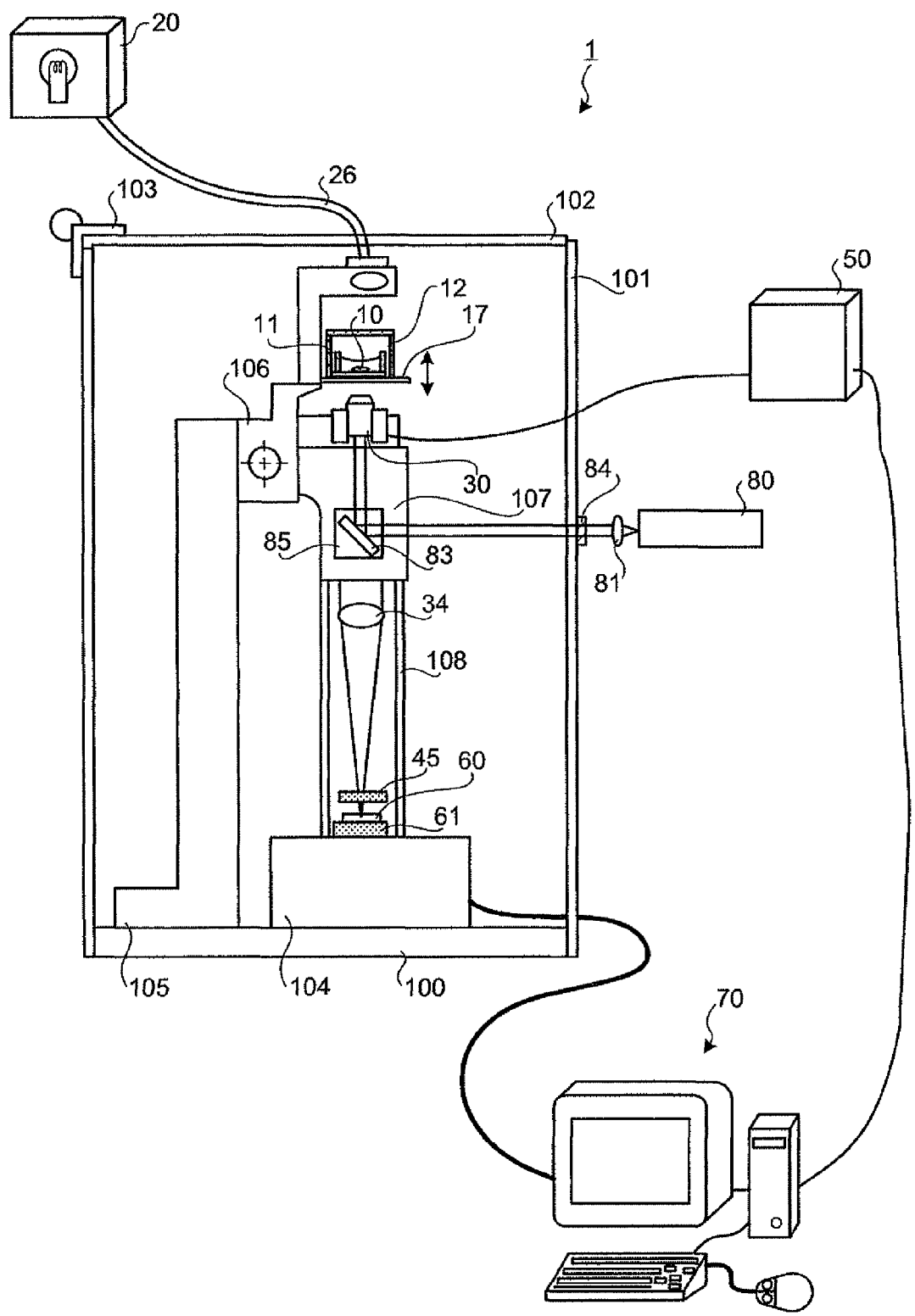
FIG. 22 is a view showing another specific example of the configuration of the focal position determining apparatus 1 according to the second embodiment.

As shown in FIG. 22, the focal position determining apparatus 1 shown in FIG. 21 may have a stage z-axis moving mechanism for moving the specimen stage 17 along the z axis as the focal position changing unit 40, instead of the objective lens z-axis moving mechanism. In FIG. 22, a Z-axis moving stage provided with the stage z-axis moving mechanism is mounted to the main body rack 106. The Z-axis moving stage is mounted below the XY specimen stage, which is movable in XY direction, so as to hold the XY specimen stage. The specimen container 11 is arranged above the Z-axis moving stage, whereby the specimen container 11 vertically moves with the vertical movement of the Z-axis moving stage. The Z-axis moving stage vertically moves by a rack-and-pinion mechanism. The operation of the rack-and-pinion mechanism is executed by turning a knob (not shown) of the rack-and-pinion mechanism by a stepping motor. The drive of the stepping motor is controlled by a computer. Thus, the operation same as that when the objective lens 30 is vertically moved can be achieved. The Z-axis moving stage may manually be moved vertically. The operation of the rack-and-pinion mechanism may be executed by turning a knob (not shown) of the rack-and-pinion mechanism.

Returning back to FIG. 21 again, the CCD camera 60 is arranged in such a manner that the center of the light-receiving surface substantially matches the optical axis. The fluorescence and luminescence emitted from the specimen (living cell) 10 transmits the dichroic mirror 83, and converges onto the light-receiving surface of the CCD camera 60 through the relay lens 34. An infrared ray cut filter 45 attached at the front surface of the CCD camera 60 is removed before starting the focal position determining apparatus 1 in order to take out infrared ray. The CCD camera 60 is connected to the information processing device 70, which processes the output signal from the CCD camera 60, via a cable.

The information processing device 70 describes and analyzes the luminescent image from the output signal from the CCD camera, measures the change over time of the intensity of the luminescence, and analyzes the output signal. The information processing device 70 further operates the CCD camera by the control unit 70a in order to receive the fluorescence and luminescence from the specimen 10 after the focal position of the objective lens 30 is focused on the observed target region 10a in the specimen 10.

The exciting light irradiating unit 80 is an argon laser having a wavelength of 488 nm and output of 10 mW, and is arranged at the outside of the light-shielding box 101 as shown in the figure. A laser inlet port 84 through which the optical fiber is inserted is formed to the light-shielding box 101. The laser beam emitted from the exciting light irradiating unit 80 passes through the collimator lens 81 and propagates in the optical fiber. The propagated laser beam reaches the dichroic mirror 83. The laser beam reaching the dichroic mirror 83 is reflected by the dichroic mirror 83 to be incident on the objective lens 30 from below. The incident laser beam is converged to be irradiated onto the specimen 10. The dichroic mirror 83 is housed in a holder 85, so that it is replaceably mounted according to the oscillation wavelength of the laser beam.

In the focal position determining apparatus 1 shown in FIG. 21, the fluorescence and luminescence emitted from the specimen 10 reaches the dichroic mirror 83 through the objective lens 30. The fluorescence and luminescence having reached the dichroic mirror 83 passes the dichroic mirror 83 to be focused on the imaging device 60a on the light-receiving surface of the CCD camera through the relay lens 34.

The explanation of the structure of the focal position determining apparatus 1 according to the second embodiment is now ended.

Next, the focal position determining process and the focal position re-determining process executed by the focal position determining apparatus 1 according to the second embodiment are the same as those explained in the first embodiment, so that the explanation thereof is omitted.

As explained above, the focal position determining apparatus 1 according to the second embodiment further includes the exciting optical system. In the focal position determining apparatus 1 according to the second embodiment, irradiation light is irradiated to the living cell from the light source 20. The focal position determining apparatus 1 repeatedly moves the objective lens 30 along the optical axis by the objective lens z-axis moving mechanism by a predetermined amount, and every time the objective lens 30 is moved, the focal position determining apparatus 1 measures the focal position of the objective lens 30 by the focal position measuring unit 50, images the living cell under the illumination by the CCD camera, and calculates the contrast of the imaged image by the feature data calculating unit 70a1. The focal position determining apparatus 1 then selects two maximum contrasts, among the accumulated plural contrasts obtained by repeatedly moving the objective lens 30, by the focal position selector 70a2, and acquires the focal positions of the objective lens 30 when the images corresponding to the selected contrasts are imaged from the accumulated plural focal positions obtained by repeatedly moving the objective lens 30. Then, the focal position determining apparatus 1 determines, by the focal position determining unit 70a3, the central position (the position at approximately the center) between two focal positions as the focal position of the objective lens 30 focused on the observed target region 10a in the living cell based on the acquired focal position, and moves the objective lens 30 by the objective lens z-axis moving mechanism so as to adjust the focal position of the objective lens 30 to the determined focal position. Accordingly, when the fluorescence and the luminescence of the observed target region 10a are simultaneously observed with the specific region in the living cell defined as the observed target region 10a, the focal position of the objective lens 30 focused on the observed target region 10a can be determined at the time of setting the living cell, with the result that the focal position of the objective lens 30 can be focused on the observed target region 10a.

Some of the techniques for measuring the ATP amount in the living cell as simultaneously observing the luminescent image and the fluorescent image of the living cell by using the focal position determining apparatus 1 according to the second embodiment will be explained below. Since the luminescent reaction (intensity of the luminescence) of luciferase depends upon the ATP amount, the quantification of the ATP by utilizing the luminescent reaction of luciferase has conventionally been executed. In a field of biotechnology, clinical examination, food hygiene, etc., an ATP amount in a cell has been measured with the use of luciferase. An ATP (adenosine-3-phosphoric acid) is a supply source of energy in a cell, and it is a material deeply related to a life phenomenon. On the other hand, luciferase in a firefly catalyzes the reaction for generating oxiluciferin, $CO_2$, AMP, and pyrophosphoric acid under the presence of ATP, $O_2$ and $Mg^{2+}$ with D-luciferin defined as a luminescent substrate, and emits light by this reaction.

The measurement of the ATP amount in a living cell is generally performed in steps (1A) to (1C) described below (H. J. Kennedy, A. E. Pouli, E. K. Ainscow, L. S. Jouaville, R. Rizzuto, G. A. Rutter, "Glucose generates sub-plasma membrane ATP microdomains in single islet β-cells", Journal of Biological Chemistry, vol. 274, pp. 13281-13291, 1999).

(1A) A cell or germ is dissolved to extract an ATP.

(1B) The extract is added to reaction solution containing luciferine and luciferase.

(1C) The amount of luminescence produced from the reaction solution having the extract added thereto is measured, whereby the ATP in the cell is quantified.

An ATP amount in a cell is generally measured by the steps (2A) to (2C) described below.

(2A) A luciferase gene is transduced to a cell for expression.

(2B) Luciferine is added to culture solution containing the cell.

(2C) The amount of luminescence produced from the culture solution to which luciferine is added is detected so as to quantify the ATP in the cell.

An ATP amount at a predetermined region (specifically, mitochondria) in a living cell is measured over time by the steps (3A) to (3B) described below (H. J. Kennedy, A. E. Pouli, E. K. Ainscow, L. S. Jouaville, R. Rizzuto, G. A. Rutter, "Glucose generates sub-plasma membrane ATP microdomains in single islet β-cells", Journal of Biological Chemistry, vol. 274, pp. 13281-13291, 1999).

(3A) A mitochondria localization signal gene is fused to luciferase gene, and the fusion gene is transduced to a cell. The fusion gene transduced to the cell is obtained by fusing a fluorescence-related gene that expresses fluorescent protein in addition to a transfer base sequence and a luminescence-related gene.

(3B) The amount of luminescence from the cell is measured over time on the presupposition that the luciferase is localized in mitochondria in the cell, whereby the variation over time in the ATP amount in the mitochondria in the cell is measured. Specifically, a fluorescent image of the cell to which the fusion gene is transduced is imaged, and it is determined whether luminescent protein is localized or not at the predetermined region based on the obtained fluorescent image. When it is determined that the luminescent protein is localized, the amount of luminescence from the cell is detected. Accordingly, it can be determined whether luminescent protein is localized or not at the predetermined region in the cell. Specifically, the localization of luminescent protein in the living cell to which the fusion gene is transduced is confirmed, and further, the amount of luminescence from the cell is measured. Further, it can be confirmed that the measured amount of luminescence is from the predetermined region.

When plural living cells to which the fusion gene is transduced are present within the range of an imaging field, plural fluorescent images and luminescent images of the cell are imaged, and it is determined for every cell whether luminescent protein is localized or not at the predetermined region based on the fluorescent image. Then, the imaged fluorescent image and the imaged luminescent image are overlapped with each other so as to select the cell to be measured among the cells in which luminescent protein is determined to be localized, whereby the amount of luminescence from the selected cell is measured. Thus, an individual cell is identified among plural cells, and the amount of luminescence from a predetermined region of a single cell can be measured as separated from the other cells. Moreover, the fluorescent image and the luminescent image are simultaneously obtained, whereby the localization of luminescent protein in the cell to be measured and the intensity of luminescence emitted from the cell can simultaneously be obtained. Therefore, it makes it possible to perform an analysis from which an influence caused by the difference in a physiological condition of an individual cell due to a transduction efficiency of a gene or a cell cycle is eliminated. As one example, it may be determined whether luminescent protein is localized or not at the predetermined region after the fluorescent image is taken, and when it is determined that the luminescent protein is localized, a luminescent image may be taken. The determination of the localization may be performed after a fluorescent image and a luminescent image are imaged.

The explanation of the focal position determining apparatus 1 according to the second embodiment is now ended.

Third Embodiment

Next, the outline, structure and process of a focal position determining apparatus 1' according to the third embodiment of the present invention will be explained in detail with reference to the drawings. The parts overlapped with those in the first and second embodiments may sometimes be omitted.

Firstly, the outline of the present invention will be explained. The present invention images a specimen (specifically, a biological specimen containing a luminescent material) while moving an objective lens, and measures the focal position of the objective lens. Then, a contrast, which is a difference between the maximum value and the minimum value of pixel values of each pixel composing the image, is calculated based on the imaged image. Then, the focal position of the objective lens focused on the observed target region is determined based on the calculated contrast and the measured focal position of the objective lens. Specifically, in the present invention, the contrast of the image obtained by imaging the specimen when the objective lens is located at a position z and the contrast of the image obtained by imaging the specimen after the objective lens is moved to the position apart from the position z by Δz are compared, whereby the focal position of the objective lens is determined. Specifically, the present invention pays an attention to the relationship between the position of the objective lens and the contrast of the image so as to obtain the focal position of the objective lens focused on the observed target region. Therefore, in the present invention, the relationship between the position of the objective lens and the contrast of the image is obtained before determining the focal position of the objective lens focused on the observed target region. Thus, when the luminescence of the observed target region, which is a specific region in the specimen, is observed, the focal position of the objective lens focused on the observed target region can be determined at the time of setting the specimen, with the result that the objective lens can be focused on the observed target region. Accordingly, when the luminescence at the luminescent region in the specimen is observed, the objective lens can be focused on the luminescent region in the specimen without confirming the luminescence from the luminescent region. Meanwhile, sometimes a contrast of an image does not change smoothly in accordance with the change in the position of the objective lens. In other words, a curve indicating the relationship between the contrast of the image and the position of the objective lens does not become smooth, so that the value of the contrast might vary. In this case, the present invention performs a smoothing process to the data in which the position of the objective lens and the contrast of the image are associated with each other, in order to achieve a smooth curve indicating the relationship between the contrast of the image and the position of the objective lens. After performing the smoothing process, the present invention may determine the focal position of the objective lens focused on the observed target region with the use of the data that has already been subject to the smoothing process.

In the present invention, the contrast may be the difference between the average value of plural high-order pixel values including the maximum value among the pixel values of each pixel composing the image and the average value of plural low-order pixel values including the minimum value among the pixel values of each pixel composing the image. With this configuration, a high contrast having high reliability can be calculated from the image even if the imaged image contains a false signal (e.g., caused by noise light such as reflection light or scattering light).

Figure 26:
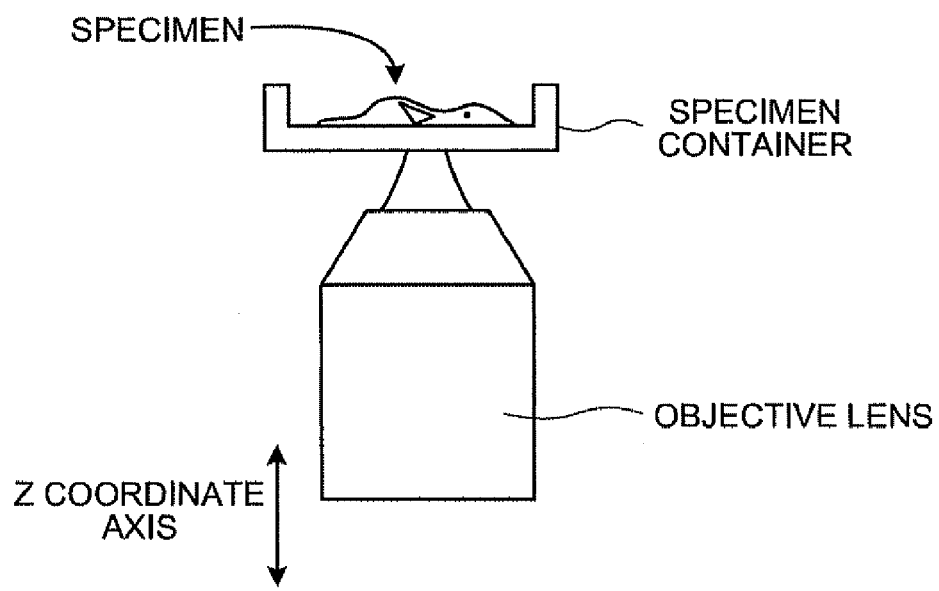
FIG. 26 is a view showing one example of a positional relationship between the objective lens and the specimen.
Figure 27:
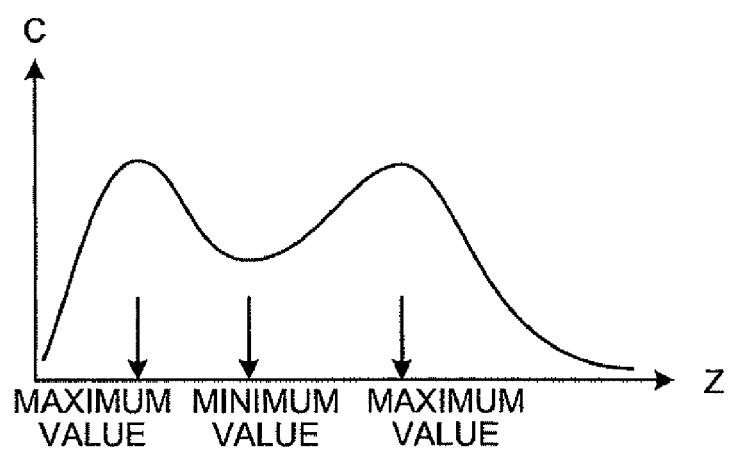
FIG. 27 is a graph showing one example of a relationship between the position of the objective lens and the contrast of the image.

Moreover, in the present invention, the calculated contrast may be compared to the others so as to search one minimum value, and the focal position of the objective lens when the image that is the original of the searched minimum value is taken may be determined as the focal position of the objective lens focused on the observed target region. Further, the calculated contrast may be compared to the others so as to search two maximum values, and the center of the focal positions of the objective lens when the images that are the originals of the searched maximum values are taken may be determined as the focal position of the objective lens focused on the observed target region. Thus, the focal position of the objective lens focused on the observed target region in the specimen can easily be determined. Meanwhile, a biological specimen such as a cell is a phase object, and has a difference in a refractive index in the subject area. Therefore, when the objective lens is moved in the z-axis direction as shown in FIG. 26 for observing the phase object described above, the contrast of the image changes as shown in FIG. 27, with the result that two maximum values and one minimum value sandwiched between two maximum values are obtained. In view of this, the present inventor has found based on this fact that the focal position of the objective lens focused on the observed target region is the focal position of the objective lens when the contrast of the image takes the minimum value, and further, the focal position of the objective lens focused on the observed target region is at approximately the center of two focal positions of the objective lens when the contrast of the image takes the maximum values.

In the present invention, the objective lens may be moved in such a manner that its moving amount is stepwisely reduced. Specifically, in the present invention, the objective lens may be moved by the moving amount that is reduced to the half of the moving amount at the previous movement. With this operation, the focal position of the objective lens focused on the observed target region in the specimen can quickly be determined.

Figure 28:
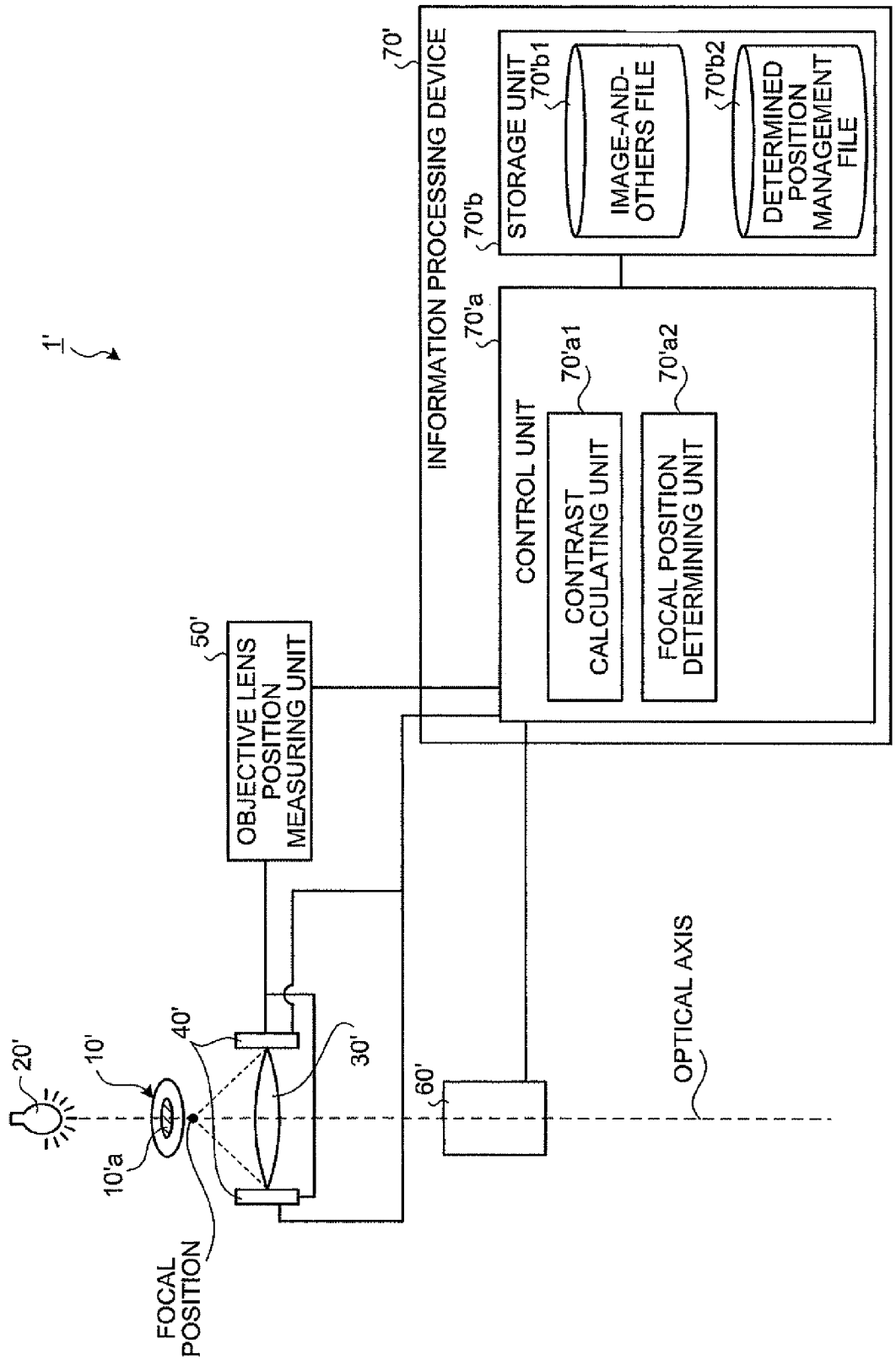
FIG. 28 is a block diagram showing a configuration of a focal position determining apparatus 1' according to a third embodiment.

Next, the structure of the focal position determining apparatus 1' according to the third embodiment of the present invention will be explained in detail with reference to FIG. 28. The focal position determining apparatus 1' is composed of a light irradiating unit 20', objective lens 30', objective lens moving unit 40', objective lens position measuring unit 50', specimen imaging unit 60', and information processing device 70'.

The light irradiating unit (light source) 20' irradiates light to a specimen 10' such as a biological specimen containing a luminescent material. The light irradiating unit 20' is an incoherent light source that emits light (visible light) having a wavelength of visible light region. Specifically, the light irradiating unit 20 is a halogen lamp, LED, tungsten lamp, mercury lamp, etc. The objective lens 30' is used for forming an image of the specimen 10'. The objective lens moving unit 40' moves the objective lens 30' in the direction of the optical axis (z axis). The objective lens position measuring unit 50' is connected to the focal position changing unit 40' so as to measure the position of the objective lens 30' on the optical axis.

The specimen imaging unit 60' images the specimen 10'. The specimen imaging unit 60' is specifically a highly-sensitive CCD camera having an imaging device.

The information processing device 70' is specifically a commercially available personal computer, and is connected to the objective lens moving unit 40', the objective lens position measuring unit 50' and the specimen imaging unit 60'. The information processing device 70' includes a control unit 70'$a$ and a storage unit 70'$b$.

The control unit 70'$a$ is a CPU or the like that integrally controls the control unit 70$a$. It has an internal memory for storing a control program such as OS (Operating System), etc., a program prescribing various process procedures, and necessary data, and performs information processing for executing various processes based on the programs. The control unit 70'$a$ controls each unit provided to the control unit, and further, controls the objective lens moving unit 40', objective lens position measuring unit 50', and specimen imaging unit 60'. When an input device such as a keyboard or a mouse or an output device such as a TV monitor is connected to the information processing device 70', the control unit 70'$a$ acquires information input by the input device or outputs the information to the output device. The control unit 70'$a$ is composed of a contrast calculating unit 70'$a1$, and a focal position determining unit 70'$a2$. The contrast calculating unit 70'$a1$ calculates a contrast defined by the difference between the maximum value and the minimum value of the pixel values of each pixel composing the image based on the imaged image taken by the specimen imaging unit 60'. The focal position determining unit 70'$a3$ determines the focal position of the objective lens focused on the observed target region based on the contrast calculated at the contrast calculating unit 70'$a1$ and position of the objective lens measured at the objective lens position measuring unit 50'.

The storage unit 70'$b$ is storage means. Specifically, a memory device such as a RAM or ROM, a fixed disk device such as a hard disk, flexible disk, optical disk, etc., may be employed as the storage unit 70'$b$. The storage unit 70'$b$ includes an image-and-others file 70'$b1$ and a determined position management file 70'$b2$. The image-and-others file 70'$b1$ stores the image imaged by the specimen imaging unit 60', the contrast calculated at the contrast calculating unit 70'$a1$ and the position of the objective lens measured at the objective lens position measuring unit 50' as associated with one another. Specifically, the image-and-others file 70'$b1$ stores image identification information for uniquely identifying an imaged image, an image, a contrast, and the position of the objective lens when the image is imaged, as associated with one another. The determined position management file 70'$b2$ stores the focal position of the objective lens 30' focused on the observed target region 10'$a$ in the specimen 10' (specifically, the focal position determined at the focal position determining unit 70'$a2$).

Next, the focal position determining process executed by the focal position determining apparatus 1' according to the third embodiment will be explained in detail with reference to FIGS. 29, 30, 34, 35, and the like. Firstly, one example of the focal position determining process executed by the focal position determining apparatus 1' according to the third embodiment will be explained in detail with reference to FIGS. 29, 30, and the like, and then, another example of the focal position determining process executed by the focal position determining apparatus 1' according to the third embodiment will be explained in detail with reference to FIGS. 34, 35, and the like.

Figure 29:
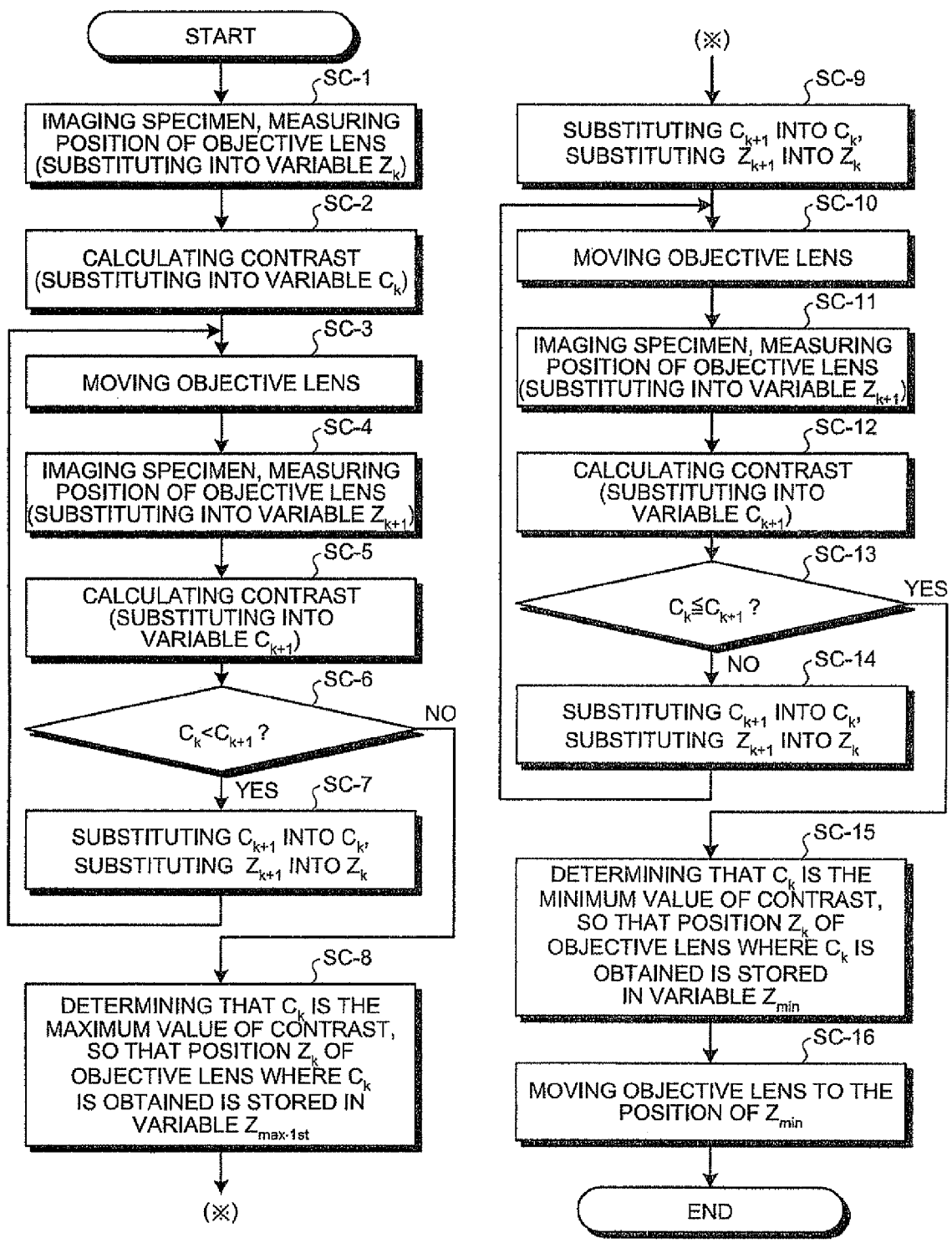
FIG. 29 is a flowchart showing one example of a focal position determining process executed by the focal position determining apparatus 1' according to the third embodiment.

When an operator sets the specimen 10' such as a living cell at a predetermined position, and starts the focal position determining apparatus 1' and the light source 20', the focal position determining apparatus 1, performs the following process shown in FIG. 29.

Firstly, the focal position determining apparatus 1' operates the specimen imaging unit 60' by the control unit 70'$a$ of the information processing device 70' so as to image the specimen 10', to which the illumination light is irradiated from the light source 20', by the specimen imaging unit 60', and stores the image of the specimen in the predetermined storage area in the image-and-others file 70'$b1$ by the control unit 70'$a$ of the information processing device 70' (step SC-1). The focal position determining apparatus 1' then operates the objective lens position measuring unit 50', by the control unit 70'$a$ of the information processing device 70', so as to measure the position of the objective lens 30' on the optical axis (z axis) by the objective lens position measuring unit 50', and substitutes, by the control unit 70'$a$ of the information processing device 70', the measured position of the objective lens 30' into a variable $Z_k$, which is set beforehand, and stores the same into the predetermined storage area in the image-and-others file 70'$b1$ (step SC-1).

Figure 31:
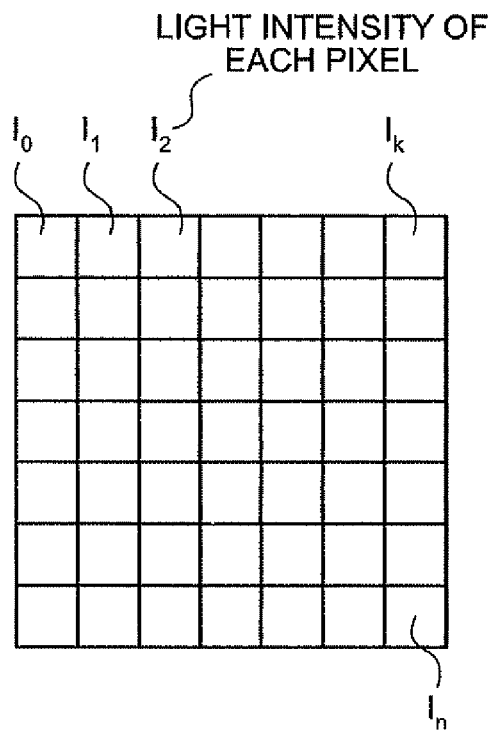
FIG. 31 is a view showing one example of a light-receiving intensity of each pixel composing an image.
Figure 32:
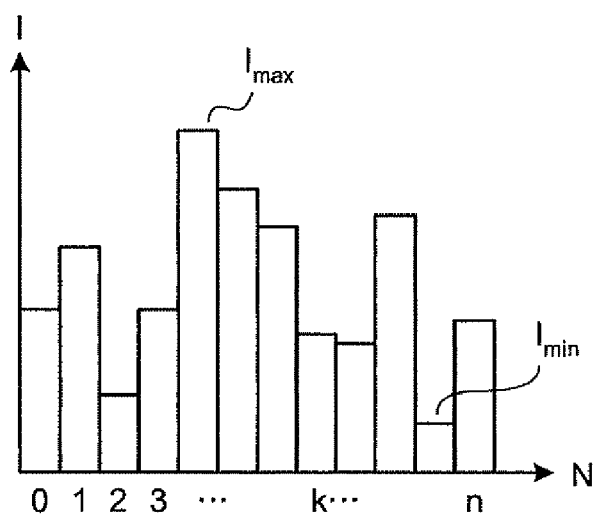
FIG. 32 is a view showing one example of the two-dimensional distribution of a light-receiving intensity of each pixel composing an image.

Then, the focal position determining apparatus 1' operates the contrast calculating unit 70'$a1$ by the control unit 70' of the information processing device 70' so as to calculate the contrast of the image from the image taken at the step SC-1 by the contrast calculating unit 70'$a1$, and then, substitutes the calculated contrast into a variable $C_k$, which is set beforehand, as well as stores the same into the predetermined storage area in the image-and-others file 70'$b1$ (step SC-2). The contrast of the image is defined by the difference between the maximum value $I_{max}$ and the minimum value $I_{min}$, i.e., "$I_{max}-I_{min}$", of the light-receiving intensity obtained by two-dimensionally reproducing the distribution of the light-receiving intensity $I_i$ ($I_0, I_1, I_2, \ldots, I_k, \ldots, I_n$ in FIG. 31) of each pixel composing the image as shown in FIG. 32.

Figure 33:
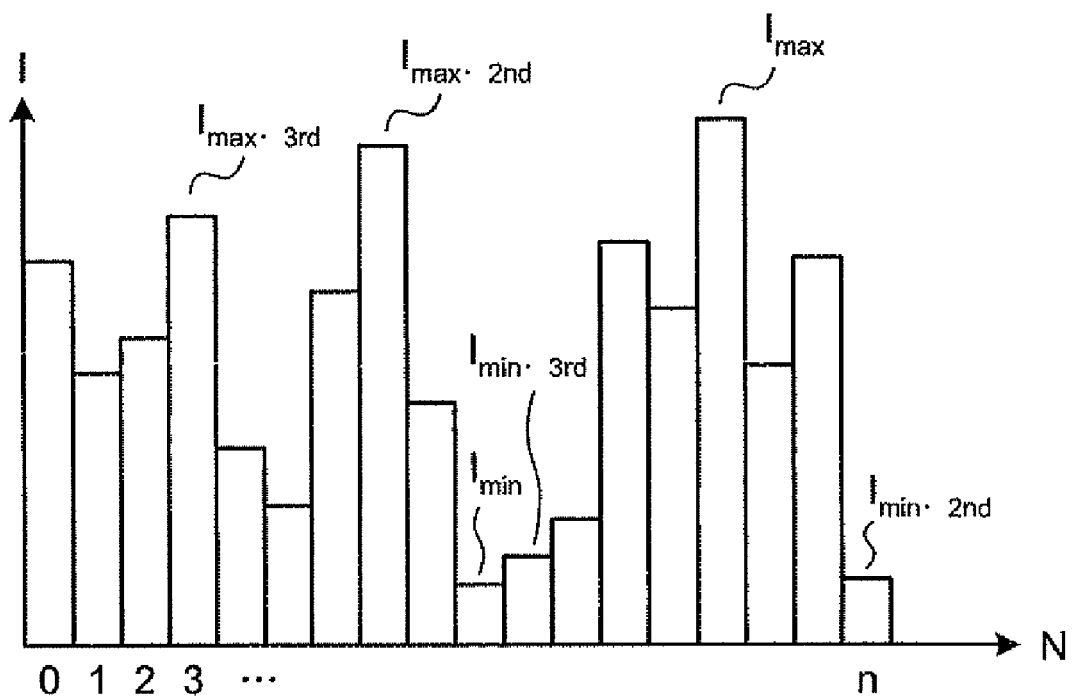
FIG. 33 is a view showing one example of the two-dimensional distribution of a light-receiving intensity of each pixel composing an image.

A false signal (e.g., a signal caused by noise light such as a reflection light or scattering light) might enter the measurement data (light-receiving intensity of each pixel composing the image). Therefore, in order to enhance the reliability of the calculated contrast, the contrast may be defined by the difference between the value of the light-receiving intensity $I_{max\cdot mean}$ and the value of the light-receiving intensity $I_{min\cdot mean}$, i.e., "$I_{max\cdot mean}-I_{min\cdot mean}$". Accordingly, the measurement error (error in the light-receiving intensity) due to the noise light can be reduced. The value of the light-receiving intensity $I_{max\cdot mean}$ is an average value of the plural high-order light-receiving intensities including the greatest light-receiving intensity $I_{max}$, i.e., the average value of the light-receiving intensities from the first light-receiving intensity to the Nth light-receiving intensity in a descending order. For example, as shown in FIG. 33, the value of the light-receiving intensity $I_{max\cdot mean}$ may be defined by the average value of the greatest light-receiving intensity $I_{max}$, the second greatest light-receiving intensity $I_{max}.2_{nd}$ and the third greatest light-receiving intensity $I_{max}.3_{rd}$, i.e., "$(I_{max}+I_{max}.2_{nd}+I_{max}.3_{rd})/3$". The value of the light-receiving intensity $I_{min\cdot mean}$ is an average value of the plural low-order light-receiving intensities including the smallest light-receiving intensity $I_{min}$, i.e., the average value of the light-receiving intensities from the first light-receiving intensity to the Nth light-receiving intensity in an ascending order. For example, as shown in FIG. 33, the value of the light-receiving intensity $I_{min\cdot mean}$ may be defined by the average value of the smallest light-receiving intensity $I_{min}$, the second smallest light-receiving intensity $I_{min}.2_{nd}$ and the third smallest light-receiving intensity $I_{min}.3_{rd}$, i.e., "$(I_{min}+I_{min}.2_{nd}+I_{min}.3_{rd})/3$".

Then, the focal position determining apparatus 1' operates the objective lens moving unit 40' by the control unit 70'$a$ of the information processing device 70' so as to move the objective lens 30' from the initial position in the direction of the optical axis by a fixed amount by the objective lens moving unit 40' (step SC-3).

Next, the focal position determining apparatus 1' operates the specimen imaging unit 60' by the control unit 70'$a$ of the information processing device 70' so as to image the specimen 10' by the specimen imaging unit 60', and stores the imaged image of the specimen into a predetermined storage area of the image-and-others file 70'$b1$ by the control unit 70'$a$ of the information processing device 70/(step SC-4). The focal position determining apparatus 1' also operates the objective lens position measuring unit 50' by the control unit 70'$a$ of the information processing device 70' so as to measure the position of the objective lens 30' on the z axis by the objective lens position measuring unit 50', substitutes the measured position of the objective lens 30' into a variable $Z_{k+1}$, which is set beforehand, and stores the same in the predetermined storage area of the image-and-others file 70'$b1$ (step SC-4).

Then, the focal position determining apparatus 1' operates the contrast calculating unit 70'$a1$ by the control unit 70'$a$ of the information processing device 70' so as to calculate the contrast of the image taken at the step SC-4 by the contrast calculating unit 70'$a1$, and then, substitutes the calculated contrast value into a variable $C_{k+1}$, which is set beforehand, as well as stores the same in the predetermined storage area of the image-and-others file 70'$b1$ (step SC-5).

Next, the focal position determining apparatus 1' operates the focal position determining unit 70'$a2$ by the control unit 70'$a$ of the information processing device 70' so as to substitute the value of $C_{k+1}$ in $C_k$ and substitute the value of $Z_{k+1}$ in $Z_k$ by the control unit 70'$a$ of the information processing device 70', when the inequality of "$C_k < C_{k+1}$" (step SC-6: Yes) is established as the result of the comparison between the value of $C_k$ and the value of $C_{k+1}$ by the focal position determining unit 70'$a2$ (step SC-7), and then, returns to the step SC-3. When the inequality of "$C_k < C_{k+1}$" (step SC-6: No) is not established as the result of the comparison between the value of $C_k$ and the value of $C_{k+1}$, the focal position determining unit 70'$a2$ determines that the value of $C_k$ is the first maximum value (first maximum value) of the contrast, so that the focal position determining apparatus 1' stores, in a variable $Z_{max}.1_{st}$ set beforehand, the value of the position $Z_k$ of the objective lens where $C_k$ is obtained (step SC-8).

Then, the focal position determining apparatus 1' substitutes the value of $C_{k+1}$ into $C_k$, and substitutes the value of $Z_{k+1}$ into $Z_k$ by the control unit 70'$a$ of the information processing device 70/(step SC-9).

Next, the focal position determining apparatus 1' operates the objective lens moving unit 40' by the control unit 70'$a$ of the information processing device 70' so as to move the objective lens 30' in the direction of the optical axis by a fixed amount by the objective lens moving unit 40' (step SC-10).

Then, the focal position determining apparatus 1' operates the specimen imaging unit 60' by the control unit 70'$a$ of the information processing device 70' so as to image the specimen 10' by the specimen imaging unit 60', and stores the imaged image of the specimen by the control unit 70'$a$ of the information processing device 70' into the predetermined storage area of the image-and-others file 70'$b1$ (step SC-11). The focal position determining apparatus 1' also operates the objective lens position measuring unit 50' by the control unit 70'$a$ of the information processing device 70' so as to measure the position of the objective lens 30' on the z axis by the objective lens position measuring unit 50', substitutes the measured position of the objective lens 30' into the variable $Z_{k+1}$, and stores the same in the predetermined storage area of the image-and-others file 70'$b1$ by the control unit 70'$a$ of the information processing device 70' (step SC-11).

Then, the focal position determining apparatus 1' operates the contrast calculating unit 70'$a1$ by the control unit 70'$a$ of the information processing device 70' so as to calculate the contrast of the image taken at the step SC-11 by the contrast calculating unit 70'$a1$, and then, substitutes the calculated contrast value into the variable $C_{k+1}$, as well as stores the same in the predetermined storage area of the image-and-others file 70'$b1$ by the control unit 70'$a$ of the information processing device 70' (step SC-12).

Next, the focal position determining apparatus 1' operates the focal position determining unit 70'$a2$ by the control unit 70'$a$ of the information processing device 70' so as to substitute the value of $C_{k+1}$ in $C_k$ and substitute the value of $Z_{k+1}$ in $Z_k$ by the control unit 70'$a$ of the information processing device 70', when the inequality of "$C_k \leq C_{k+1}$" is not established (step SC-13: No) as the result of the comparison between the value of $C_k$ and the value of $C_{k+1}$ by the focal position determining unit 70'$a2$ (step SC-14), and then, returns to the step SC-10. When the inequality of "$C_k \leq C_{k+1}$" is established (step SC-13: Yes) as the result of the comparison between the value of $C_k$ and the value of $C_{k+1}$, the focal position determining unit 70'$a2$ determines that the value of $C_k$ is the first minimum value of the contrast and determines that the position of the objective lens 30' corresponding to the minimum value is the focal position of the objective lens 30' focused on the observed target region 10'$a$ in the specimen 10', so that the focal position determining apparatus 1' stores, in a variable $Z_{min}$ set beforehand, the value of the position $Z_k$ of the objective lens where $C_k$ is obtained (step SC-15).

Next, the focal position determining apparatus 1' operates the objective lens moving unit 40' by the control unit 70'$a$ of the information processing device 70' so as to move the objective lens 30' to the position corresponding to the value of the variable $Z_{min}$ by the objective lens moving unit 40' (step SC-16).

The explanation of the focal position determining process shown in FIG. 29 is now ended.

Figure 30:
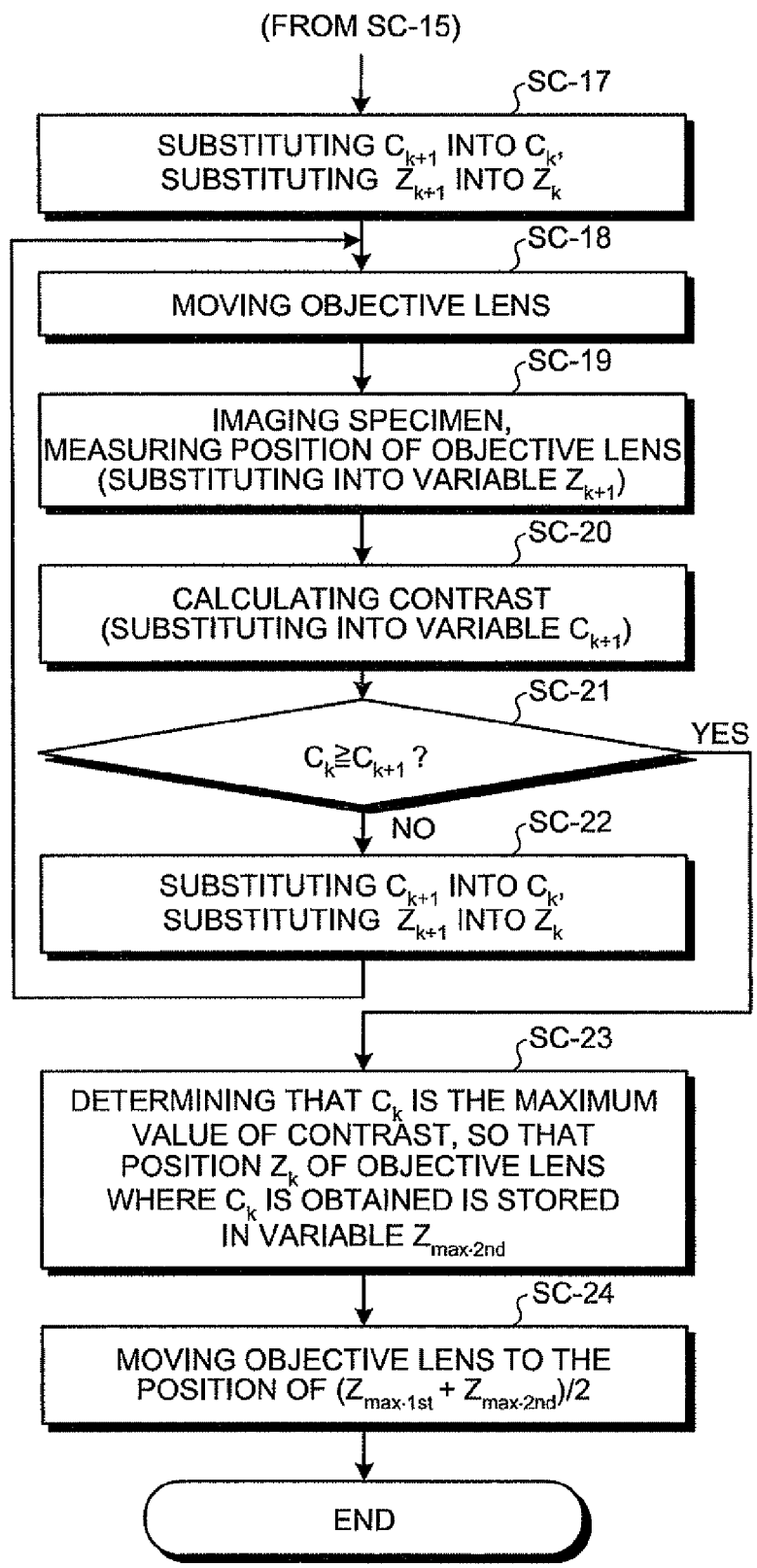
FIG. 30 is a flowchart showing one example of a focal position determining process executed by the focal position determining apparatus 1' according to the third embodiment.

The focal position determining apparatus 1' may execute the focal position determining process shown in FIG. 30 subsequent to the step SC-15. With this, the measurement precision of the focal position of the objective lens 30' focused on the observed target region 10'$a$ of the specimen 10' can further be enhanced. The focal position determining process shown in FIG. 30 will be explained below. The parts overlapped with those in the aforesaid explanation may sometimes be omitted.

Subsequent to the step SC-15, the focal position determining apparatus 1' substitutes the value of $C_{k+1}$ into $C_k$ and the value of $Z_{k*1}$ into $Z_k$ by the control unit 70'$a$ of the information processing device 70' (step SC-17).

Then, the focal position determining apparatus 1' operates the objective lens moving unit 40' by the control unit 70'$a$ of the information processing device 70' so as to move the objective lens 30' from the initial position in the direction of the optical axis by a fixed amount by the objective lens moving unit 40' (step SC-18).

Next, the focal position determining apparatus 1' operates the specimen imaging unit 60' by the control unit 70'$a$ of the information processing device 70' so as to image the specimen 10 by the specimen imaging unit 60', and stores the imaged image of the specimen into a predetermined storage area of the image-and-others file 70'$b1$ by the control unit 70'$a$ of the information processing device 70' (step SC-19). The focal position determining apparatus 1' also operates the objective lens position measuring unit 50' by the control unit 70'$a$ of the information processing device 70' so as to measure the position of the objective lens 30' on the z axis by the objective lens position measuring unit 50', substitutes the measured position of the objective lens 30' into the variable $Z_{k+1}$, and stores the same in the predetermined storage area of the image-and-others file 70'$b1$ by the control unit 70'$a$ of the information processing device 70' (step SC-19).

Then, the focal position determining apparatus 1' operates the contrast calculating unit 70'$a1$ by the control unit 70'$a$ of the information processing device 70' so as to calculate the contrast of the image taken at the step SC-19 by the contrast calculating unit 70'$a1$, and then, substitutes the calculated contrast value into the variable $C_{k+1}$, as well as stores the same in the predetermined storage area of the image-and-others file 70'$b1$ by the control unit 70'$a$ of the information processing device 70' (step SC-20).

Next, the focal position determining apparatus 1' operates the focal position determining unit 70'$a2$ by the control unit 70'$a$ of the information processing device 70' so as to substitute the value of $C_{k+1}$ in $C_k$ and substitute the value of $Z_{k+1}$ in $Z_k$ by the control unit 70'$a$ of the information processing device 70', when the inequality of "$C_k \geq C_{k+1}$" is not established (step SC-21: No) as the result of the comparison between the value of $C_k$ and the value of $C_{k+1}$ by the focal position determining unit 70'$a2$ (step SC-22), and then, returns to the step SC-18. When the inequality of "$C_k \geq C_{k+1}$" is established (step SC-21: Yes) as the result of the comparison between the value of $C_k$ and the value of $C_{k+1}$, the focal position determining unit 70'$a2$ determines that the value of $C_k$ is the second maximum value (second maximum value) of the contrast, so that the focal position determining apparatus 1' determines that the center of the position of the objective lens 30' corresponding to the first maximum value obtained at the step SC-8 and the position of the objective lens 30' corresponding to the second maximum value is the focal position of the objective lens 30' focused on the observed target region 10'$a$ in the specimen 10' and stores, in a variable $Z_{max}.2_{nd}$ set beforehand, the value of the position $Z_k$ of the objective lens where $C_k$ is obtained (step SC-23).

Next, the focal position determining apparatus 1' operates the objective lens moving unit 40' by the control unit 70'$a$ of the information processing device 70' so as to move the objective lens 30' to the position corresponding to the value of the variable "$(Z_{max}.1_{st}+Z_{max}.2_{nd})/2$" by the objective lens moving unit 40' (step SC-24).

The explanation of the focal position determining process shown in FIG. 30 is now ended.

Next, another example of the focal position determining process executed by the focal position determining apparatus 1' according to the third embodiment will be explained with reference to FIGS. 34, 35, and the like. The parts overlapped with those in the aforesaid explanation may sometimes be omitted.

The focal position determining apparatus 1' moves the objective lens 30' in a greater amount at the initial stage, then, gradually reduces its moving amount while changing the moving direction of the objective lens 30', and finally, converges the position of the objective lens 30, to the position where the contrast of the image takes the minimum value.

Specifically, the focal position determining apparatus 1' executes the steps 1 to 11 described below.

Step 1: A contrast ($C_1$) of an image is acquired at the start position (initial position) of the objective lens 30'.

Step 2: The objective lens 30' is greatly moved to the position exceeding the position corresponding to the second maximum value in the positive (+) direction of the z axis set beforehand.

Step 3: A contrast ($C_k$) of an image is acquired at the position where the objective lens 30' is moved at the step 2.

Step 4: The objective lens 30' is moved in the positive direction of the z axis by one step (a moving amount per one movement set beforehand).

Step 5: A contrast ($C_{k+1}$) of an image is acquired at the position where the objective lens 30' is moved at the step 4.

Step 6: The value of $C_k$ and the value of $C_{k+1}$ are compared.

Step 7: When the inequality of "$C_k > C_{k+1}$" is established, the objective lens 30' is greatly moved to the vicinity of the position corresponding to the first maximum value in the negative (−) direction of the z axis. Further, when the inequality of "$C_k < C_{k+1}$" is established, the objective lens 30' is moved in the negative direction of the z axis by one step.

Step 8: A contrast ($C_{k+1}$) of the image is acquired at the position where the objective lens 30' is moved at the step 7.

Step 9: The value of $C_k$ and the value of $C_{k+1}$ are compared.

Step 10: When the inequality of "$C_k < C_{k+1}$" is established, the objective lens 30' is greatly moved to the vicinity of the position corresponding to the second maximum value in the positive direction of the z axis.

Step 11: The above-mentioned steps are repeated as reducing the moving amount of the objective lens 30', whereby the position of the objective lens 30' corresponding to the minimum value of the contrast of the image is obtained. This position is determined as the focal position of the objective lens 30' focused on the observed target region 10'$a$ in the specimen 10'.

The focal position determining apparatus 1, may set the moving amount of the objective lens 30' in and after the second time to a half the moving amount of the previous movement, compare the value of $C_k$ and the value of $C_{k+1}$ at the position where the objective lens 30' is moved, and set the moving amount in the next movement to a half the moving amount of the last-time movement, in the above-mentioned steps. These movement and comparison may be repeated. Specifically, the moving amount of the objective lens 30' is reduced to a half every comparison of the contrast, whereby the moving distance of the objective lens 30' is reduced, and finally, the position of the objective lens 30' may be converged to the position of the objective lens where the contrast takes the minimum value. Specifically, the focal position determining apparatus 1' may execute the focal position determining process shown in FIGS. 34 and 35. Accordingly, the focal position of the objective lens 30' focused on the observed target region 10'$a$ in the specimen 10' can be determined with higher speed.

The focal position determining process shown in FIGS. 34 and 35 will be explained here. The parts overlapped with those in the above-mentioned explanation may sometimes be omitted. When an operator sets the specimen 10', such as a living cell, at a predetermined position, and starts up the focal position determining apparatus 1' and the light source 20', the focal position determining apparatus 1' executes the following process.

Firstly, the focal position determining apparatus 1' operates the specimen imaging unit 60' by the control unit 70'$a$ of the information processing device 70' so as to image the specimen 10', to which the illumination light is irradiated from the light source 20', by the specimen imaging unit 60', and stores the imaged image of the specimen in the predetermined storage area in the image-and-others file 70'$b1$ by the control unit 70'$a$ of the information processing device 70' (step SD-1). The focal position determining apparatus 1' then operates the objective lens position measuring unit 50', by the control unit 70'$a$ of the information processing device 70', so as to measure the position of the objective lens 30' on the optical axis (z axis) by the objective lens position measuring unit 50', and substitutes the position of the objective lens 30' measured at the objective lens position measuring unit 50' into a variable $Z_k$, which is set beforehand, and stores the same into the predetermined storage area in the image-and-others file 70'$b1$ by the control unit 70'$a$ of the information processing device 70' (step SD-1).

Then, the focal position determining apparatus 1' operates the contrast calculating unit 70'$a1$ by the control unit 70'$a$ of the information processing device 70' so as to calculate the contrast of the image from the image taken at the step SD-1 by the contrast calculating unit 70'$a1$, and then, substitutes the calculated contrast into a variable $C_k$, which is set beforehand, as well as stores the same into the predetermined storage area in the image-and-others file 70'$b1$ by the control unit 70'$a$ of the information processing device 70' (step SD-2).

Then, the focal position determining apparatus 1' operates the objective lens moving unit 40' by the control unit 70'$a$ of the information processing device 70' so as to move, by the objective lens moving unit 40', the objective lens 30' from the initial position in the positive (+) direction of the optical axis (z axis) by a moving step number N(N is a variable storing the moving step number), which is set beforehand (step SD-3). The positive and negative directions of the optical axis and the moving amount per one step are set beforehand.

Next, the focal position determining apparatus 1' operates the specimen imaging unit 60' by the control unit 70'$a$ of the information processing device 70' so as to image the specimen 10' by the specimen imaging unit 60', and stores the imaged image of the specimen into the predetermined storage area of the image-and-others file 70'$b1$ by the control unit 70'$a$ of the information processing device 70' (step SD-4). The focal position determining apparatus 1' also operates the objective lens position measuring unit 50' by the control unit 70'$a$ of the information processing device 70' so as to measure the position of the objective lens 30' on the z axis by the objective lens position measuring unit 50', substitutes the measured position of the objective lens 30' into a variable $Z_{k+1}$, which is set beforehand, and stores the same in the predetermined storage area of the image-and-others file 70'$b1$ by the control unit 70'$a$ of the information processing device 70' (step SD-4).

Then, the focal position determining apparatus 1' operates the contrast calculating unit 70'$a1$ by the control unit 70'$a$ of the information processing device 70' so as to calculate the contrast of the image taken at the step SD-4 by the contrast calculating unit 70'$a1$, and then, substitutes the calculated contrast value into the variable $C_{k+1}$, which is set beforehand, as well as stores the same in the predetermined storage area of the image-and-others file 70'$b1$ by the control unit 70'$a$ of the information processing device 70' (step SD-5).

Then, the focal position determining apparatus 1' substitutes a half (N/2) of the value of N into the variable N that stores the moving step number by the control unit 70'$a$ of the information processing device 70' (step SD-6).

Next, the focal position determining apparatus 1' operates the focal position determining unit 70'$a2$ by the control unit 70'$a$ of the information processing device 70' so as to compare the value of $C_k$ and the value of $C_{k+1}$. When "$C_k<C_{k+1}$" is established (step SD-7: Yes), the focal position determining apparatus 1' operates the objective lens moving unit 40' by the control unit 70'$a$ of the information processing device 70' so as to move, by the objective lens moving unit 40', the objective lens 30' in the negative (−) direction of the optical axis (z axis) by the moving step number N that is updated at the step SD-6 (step SD-8), substitutes the value of $C_{k+1}$ in $C_k$ and substitutes the value of $Z_{k+1}$ in $Z_k$ by the control unit 70'$a$ of the information processing device 70' (step SD-9). Then, the focal position determining apparatus 1' returns to the step SD-4. When "$C_k<C_{k+1}$" is not established (step SD-7: No), the focal position determining apparatus 1' operates the objective lens moving unit 40' by the control unit 70'$a$ of the information processing device 70' so as to move, by the objective lens moving unit 40', the objective lens 30' in the positive (+) direction of the optical axis (z axis) by the moving step number N that is updated at the step SD-6 (step SD-10), substitutes the value of $C_{k+1}$ in $C_k$ and substitutes the value of $Z_{k+1}$ in $Z_k$ by the control unit 70'$a$ of the information processing device 70' (step SD-11).

Next, the focal position determining apparatus 1' operates the specimen imaging unit 60' by the control unit 70'$a$ of the information processing device 70' so as to image the specimen 10' by the specimen imaging unit 60', and stores the imaged image of the specimen into the predetermined storage area of the image-and-others file 70'$b1$ by the control unit 70'$a$ of the information processing device 70' (step SD-12). The focal position determining apparatus 1' also operates the objective lens position measuring unit 50' by the control unit 70'$a$ of the information processing device 70' so as to measure the position of the objective lens 30' on the z axis by the objective lens position measuring unit 50', substitutes the measured position of the objective lens 30' into the variable $Z_{k+1}$, and stores the same in the predetermined storage area of the image-and-others file 70'$b1$ by the control unit 70'$a$ of the information processing device 70' (step SD-12).

Then, the focal position determining apparatus 1' operates the contrast calculating unit 70'$a1$ by the control unit 70'$a$ of the information processing device 70' so as to calculate the contrast of the image taken at the step SD-12 by the contrast calculating unit 70'$a1$, and then, substitutes the calculated contrast value into the variable $C_{k+1}$, as well as stores the same in the predetermined storage area of the image-and-others file 70'$b1$ by the control unit 70'$a$ of the information processing device 70' (step SD-13).

Then, the focal position determining apparatus 1' substitutes a half (N/2) of the value of N into the variable N by the control unit 70'$a$ of the information processing device 70' (step SD-14).

Next, the focal position determining apparatus 1' operates the focal position determining unit 70'$a2$ by the control unit 70'$a$ of the information processing device 70' so as to compare the value of $C_k$ and the value of $C_{k+1}$. When "$C_k>C_{k+1}$" is established (step SD-15: Yes), the focal position determining apparatus 1' operates the objective lens moving unit 40' by the control unit 70'$a$ of the information processing device 70' so as to move, by the objective lens moving unit 40', the objective lens 30' in the negative (−) direction of the optical axis (z axis) by the moving step number N that is updated at the step SD-14 (step SD-16), substitutes the value of $C_{k+1}$ in $C_k$ and substitutes the value of $Z_{k+1}$ in $Z_k$ by the control unit 70'$a$ of the information processing device 70' (step SD-17). Then, the focal position determining apparatus 1' returns to the step SD-12. When "$C_k>C_{k+1}$" is not established (step SD-15: No), the focal position determining apparatus 1' operates the objective lens moving unit 40' by the control unit 70'$a$ of the information processing device 70' so as to move, by the objective lens moving unit 40', the objective lens 30' in the positive (+) direction of the optical axis (z axis) by the moving step number N that is updated at the step SD-14 (step SD-18), substitutes the value of $C_{k+1}$ in $C_k$ and substitutes the value of $Z_{k+1}$ in $Z_k$ by the control unit 70'$a$ of the information processing device 70' (step SD-19).

Figure 35:
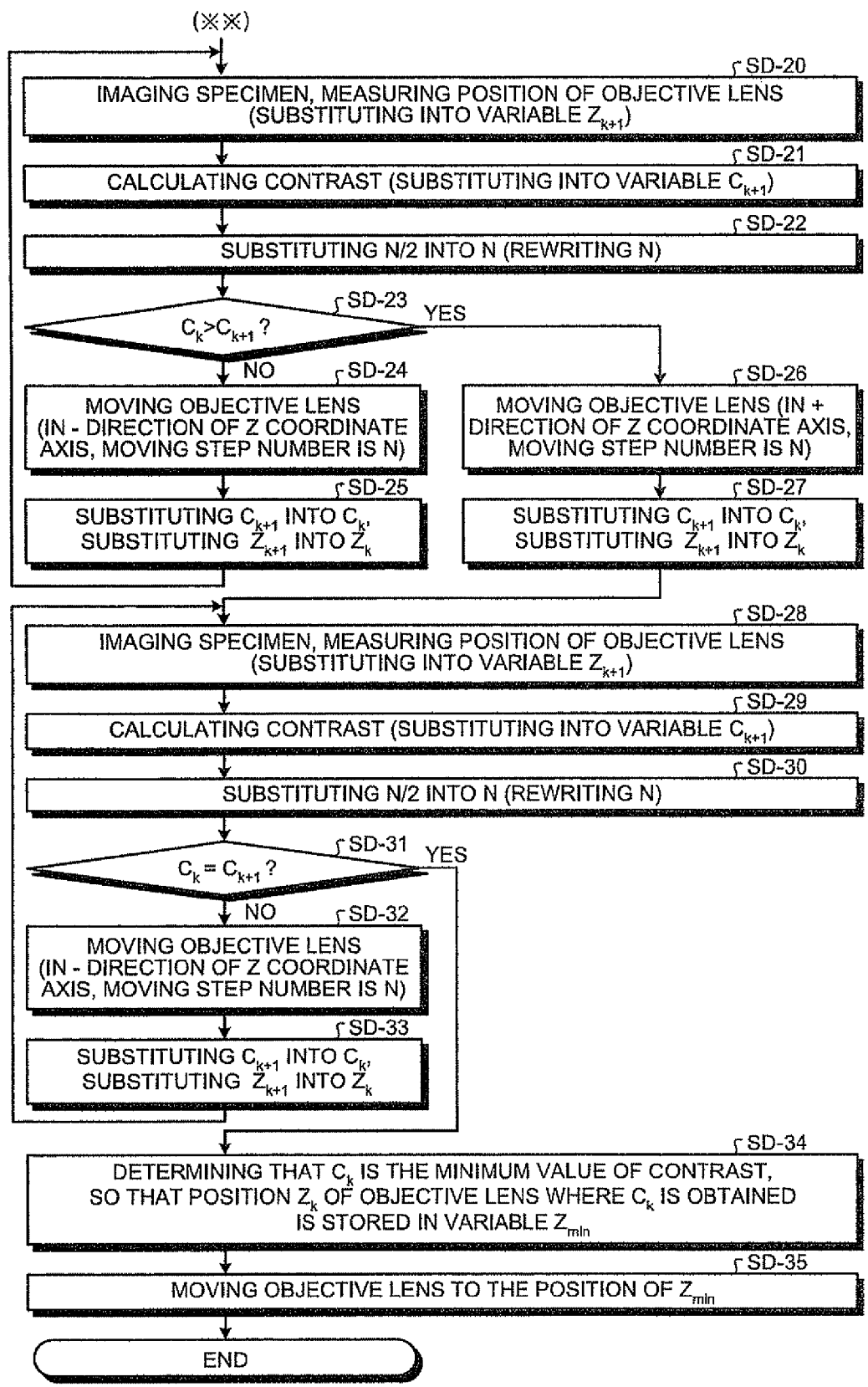
FIG. 35 is a flowchart showing one example of the focal position determining process executed by the focal position determining apparatus 1' according to the third embodiment.

Next, referring next to FIG. 35, the focal position determining apparatus 1' operates the specimen imaging unit 60' by the control unit 70'$a$ of the information processing device 70' so as to image the specimen 10' by the specimen imaging unit 60', and stores the imaged image of the specimen into the predetermined storage area of the image-and-others file 70'b1 by the control unit 70'a of the information processing device 70' (step SD-20). The focal position determining apparatus 1' also operates the objective lens position measuring unit 50' by the control unit 70'a of the information processing device 70' so as to measure the position of the objective lens 30' on the z axis by the objective lens position measuring unit 50', substitutes the measured position of the objective lens 30' into the variable $Z_{k+1}$, and stores the same in the predetermined storage area of the image-and-others file 70'b1 by the control unit 70'a of the information processing device 70' (step SD-20).

Then, the focal position determining apparatus 1' operates the contrast calculating unit 70'a1 by the control unit 70'a of the information processing device 70' so as to calculate the contrast of the image taken at the step SD-20 by the contrast calculating unit 70'a1, and then, substitutes the calculated contrast value into the variable $C_{k+1}$, as well as stores the same in the predetermined storage area of the image-and-others file 70'b1 by the control unit 70'a of the information processing device 70' (step SD-21).

Then, the focal position determining apparatus 1' substitutes a half (N/2) of the value of N into the variable N by the control unit 70'a of the information processing device 70' (step SD-22).

Next, the focal position determining apparatus 1' operates the focal position determining unit 70'a2 by the control unit 70'a of the information processing device 70' so as to compare the value of $C_k$ and the value of $C_{k+1}$. When "$C_k > C_{k+1}$" is not established (step SD-23: No), the focal position determining apparatus 1' operates the objective lens moving unit 40' by the control unit 70'a of the information processing device 70' so as to move, by the objective lens moving unit 40', the objective lens 30' in the negative (−) direction of the optical axis (z axis) by the moving step number N that is updated at the step SD-22 (step SD-24), substitutes the value of $C_{k+1}$ in $C_k$ and substitutes the value of $Z_{k+1}$ in $Z_k$ by the control unit 70'a of the information processing device 70' (step SD-25). Then, the focal position determining apparatus 1' returns to the step SD-20. When "$C_k > C_{k+1}$" is established (step SD-23: Yes), the focal position determining apparatus 1' operates the objective lens moving unit 40' by the control unit 70'a of the information processing device 70' so as to move, by the objective lens moving unit 40', the objective lens 30' in the positive (+) direction of the optical axis (z axis) by the moving step number N that is updated at the step SD-22 (step SD-26), substitutes the value of $C_{k+1}$ in $C_k$ and substitutes the value of $Z_{k+1}$ in $Z_k$ by the control unit 70'a of the information processing device 70' (step SD-27).

Next, the focal position determining apparatus 1' operates the specimen imaging unit 60' by the control unit 70'a of the information processing device 70' so as to image the specimen 10' by the specimen imaging unit 60', and stores the imaged image of the specimen into the predetermined storage area of the image-and-others file 70'b1 by the control unit 70'a of the information processing device 70' (step SD-28). The focal position determining apparatus 1' also operates the objective lens position measuring unit 50' by the control unit 70'a of the information processing device 70' so as to measure the position of the objective lens 30' on the z axis by the objective lens position measuring unit 50', substitutes the measured position of the objective lens 30' into the variable $Z_{k+1}$, and stores the same in the predetermined storage area of the image-and-others file 70'b1 by the control unit 70'a of the information processing device 70' (step SD-28).

Then, the focal position determining apparatus 1' operates the contrast calculating unit 70'a1 by the control unit 70'a of the information processing device 70' so as to calculate the contrast of the image taken at the step SD-28 by the contrast calculating unit 70'a1, and then, substitutes the calculated contrast value into the variable $C_{k+1}$, as well as stores the same in the predetermined storage area of the image-and-others file 70'b1 by the control unit 70'a of the information processing device 70' (step SD-29).

Then, the focal position determining apparatus 1' substitutes a half (N/2) of the value of N into the variable N by the control unit 70'a of the information processing device 70' (step SD-30).

Next, the focal position determining apparatus 1' operates the focal position determining unit 70'a2 by the control unit 70'a of the information processing device 70' so as to compare the value of $C_k$ and the value of $C_{k+1}$. When "$C_k = C_{k+1}$" is not established (step SD-31: No), the focal position determining apparatus 1' operates the objective lens moving unit 40 by the control unit 70'a of the information processing device 70, so as to move, by the objective lens moving unit 40', the objective lens 30' in the negative (−) direction of the optical axis (z axis) by the moving step number N that is updated at the step SD-30 (step SD-32), substitutes the value of $C_{k+1}$ in $C_k$ and substitutes the value of $Z_{k+1}$ in $Z_k$ by the control unit 70'a of the information processing device 70' (step SD-33). Then, the focal position determining apparatus 1' returns to the step SD-28. When "$C_k = C_{k+1}$" is established (step SD-31: Yes), the focal position determining unit 70'a2 determines that the value of $C_k$ is the minimum value of the contrast, so that the focal position determining unit 70'a2 determines that the position of the objective lens 30' corresponding to the minimum value is the focal position of the objective lens 30' focused on the observed target region 10'a in the specimen 10' and the focal position determining apparatus 1' stores, in a variable $Z_{min}$ set beforehand, the value of the position $Z_k$ of the objective lens where $C_k$ is obtained (step SD-34).

Next, the focal position determining apparatus 1' operates the objective lens moving unit 40' by the control unit 70'a of the information processing device 70' so as to move the objective lens 30' to the position corresponding to the value of the variable $Z_{min}$ by the objective lens moving unit 40' (step SD-35).

Figure 34:
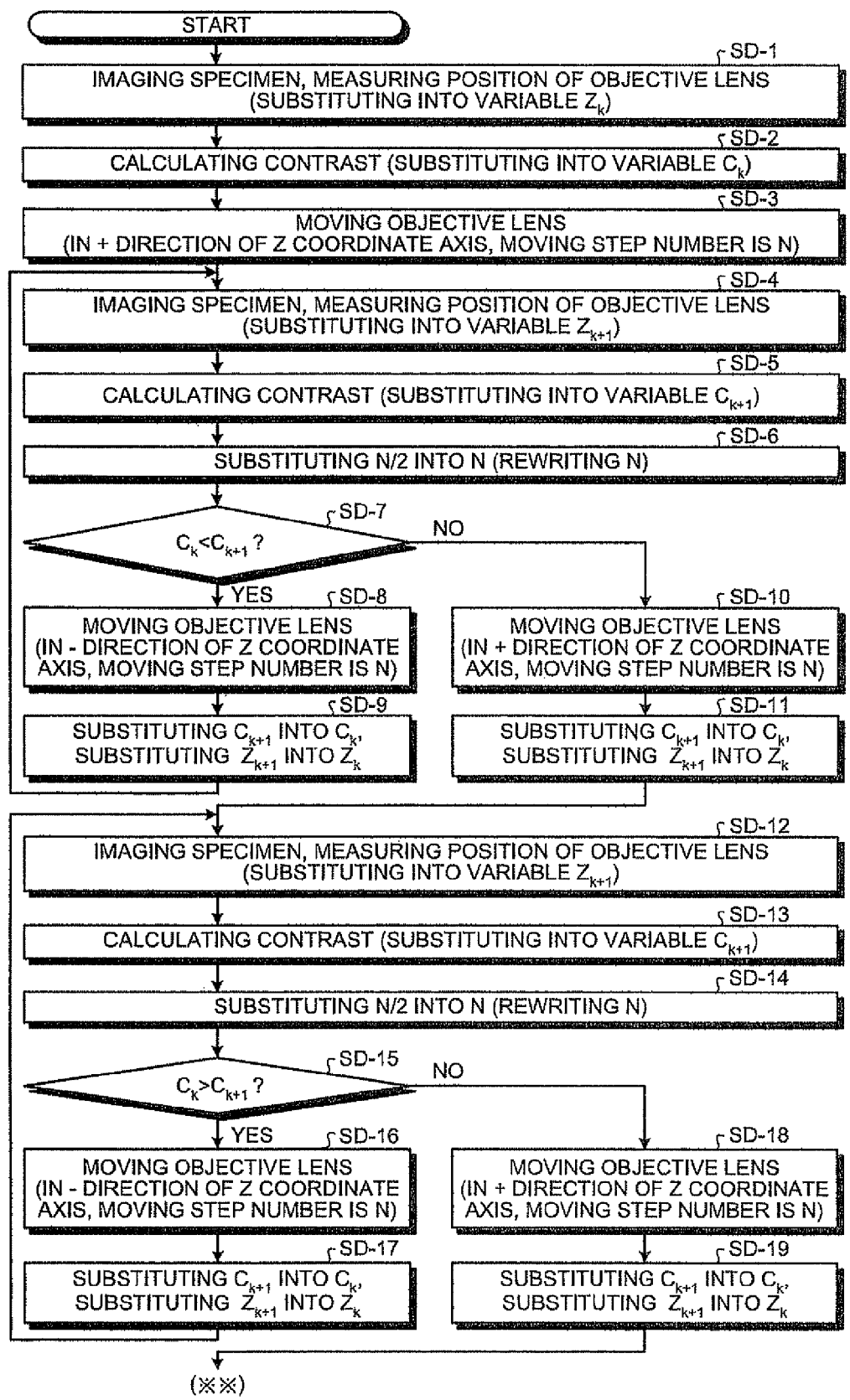
FIG. 34 is a flowchart showing one example of the focal position determining process executed by the focal position determining apparatus 1' according to the third embodiment.

The explanation of the focal position determining process shown in FIGS. 34 and 35 is now ended.

As explained above, the focal position determining apparatus 1' according to the third embodiment images a specimen as well as measures the focal position of the objective lens, while moving the objective lens. A contrast, which is the difference between the maximum value and the minimum value of a pixel value of each pixel composing the image is calculated based on the imaged image. Then, the focal position of the objective lens focused on the observed target region is determined based on the calculated contrast and the measured focal position of the objective lens. Accordingly, when a specific region in a specimen is defined as the observed target region, and the luminescence of the observed target region is observed, the focal position of the objective lens focused on the observed target region can be determined at the time of setting the specimen, with the result that the focal position of the objective lens can be focused on the observed target region. Further, when a luminescence from a luminescent region in the specimen is observed, the objective lens can be focused on the luminescent region in the specimen without confirming the luminescence from the luminescent region.

The focal position determining apparatus 1' according to the third embodiment may compare the calculated contrast with the others so as to search one minimum value, and may determine the focal position of the objective lens when the image that is the original of the searched minimum value is imaged as the focal position of the objective lens focused on the observed target region. Specifically, the focal position determining apparatus $1'$ according to the third embodiment may move the objective lens in the z-axis direction for every step, compare the contrasts of the images at every step, and may determine the position of the objective lens on the z axis when the contrast of the image becomes the minimum as the focal position of the objective lens focused on the observed target region. Thus, the focal position of the objective lens focused on the observed target region in the specimen can easily be determined.

The focal position determining apparatus $1'$ according to the third embodiment may compare the calculated contrast with the others so as to search two maximum values, and may determine the center of the focal positions of the objective lens when the images that are the originals of the searched maximum values are imaged as the focal position of the objective lens focused on the observed target region. Specifically, the focal position determining apparatus $1'$ according to the third embodiment may move the objective lens in the z-axis direction for every step, compare the contrasts of the images at every step, determine two positions of the objective lens on the z axis where the contrasts of the images become the maximum, and determine the central position between the positions of the objective lens on the z axis corresponding to two maximum values as the focal position of the objective lens focused on the observed target region. Thus, the focal position of the objective lens focused on the observed target region in the specimen can easily be determined.

The focal position determining apparatus $1'$ according to the third embodiment may move the objective lens as reducing the moving amount stepwise. Specifically, in the focal position determining apparatus $1'$ according to the third embodiment, the objective lens may be moved by the moving width that is reduced to the half of the moving width at the previous movement for every moving step. With this operation, the focal position of the objective lens focused on the observed target region in the specimen can quickly be determined.

The focal position determining apparatus $1'$ according to the third embodiment may define the contrast as the difference between the average value of plural high-order pixel values including the maximum value among the pixel values of each pixel composing the image and the average value of plural low-order pixel values including the minimum value among the pixel values of each pixel composing the image. With this configuration, a high contrast having high reliability can be calculated from the image even if the imaged image contains a false signal (e.g., caused by noise light such as reflection light or scattering light).

[II] Embodiments of a feeble light detecting apparatus and a feeble light detecting method according to the present invention will be explained in detail with reference to the drawings. It is to be noted that the embodiments does not limit the present invention.

First Embodiment

Figure 36:
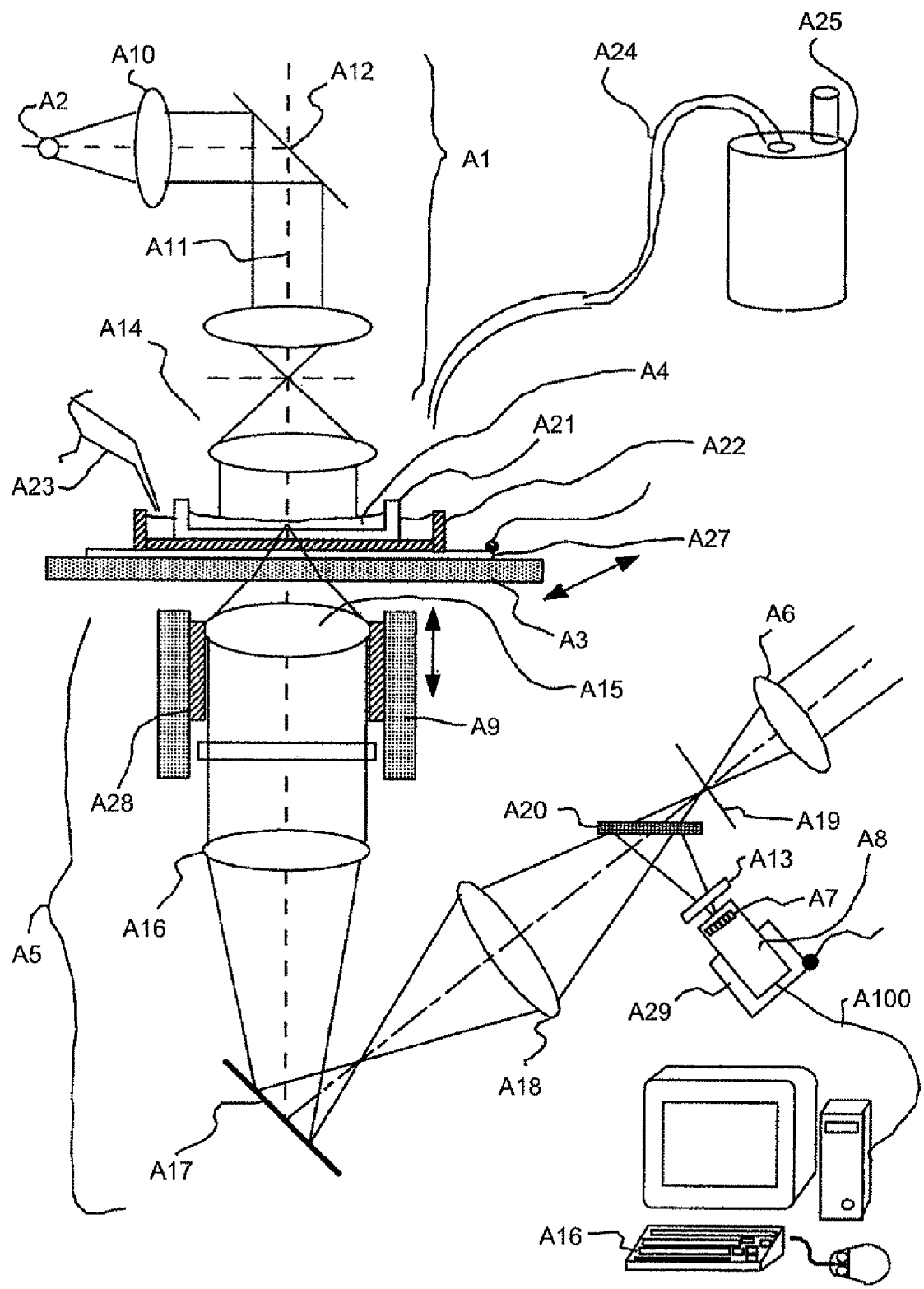
FIG. 36 is a view showing a structure of an optical system involved with the first embodiment of the present invention.
Figure 37:
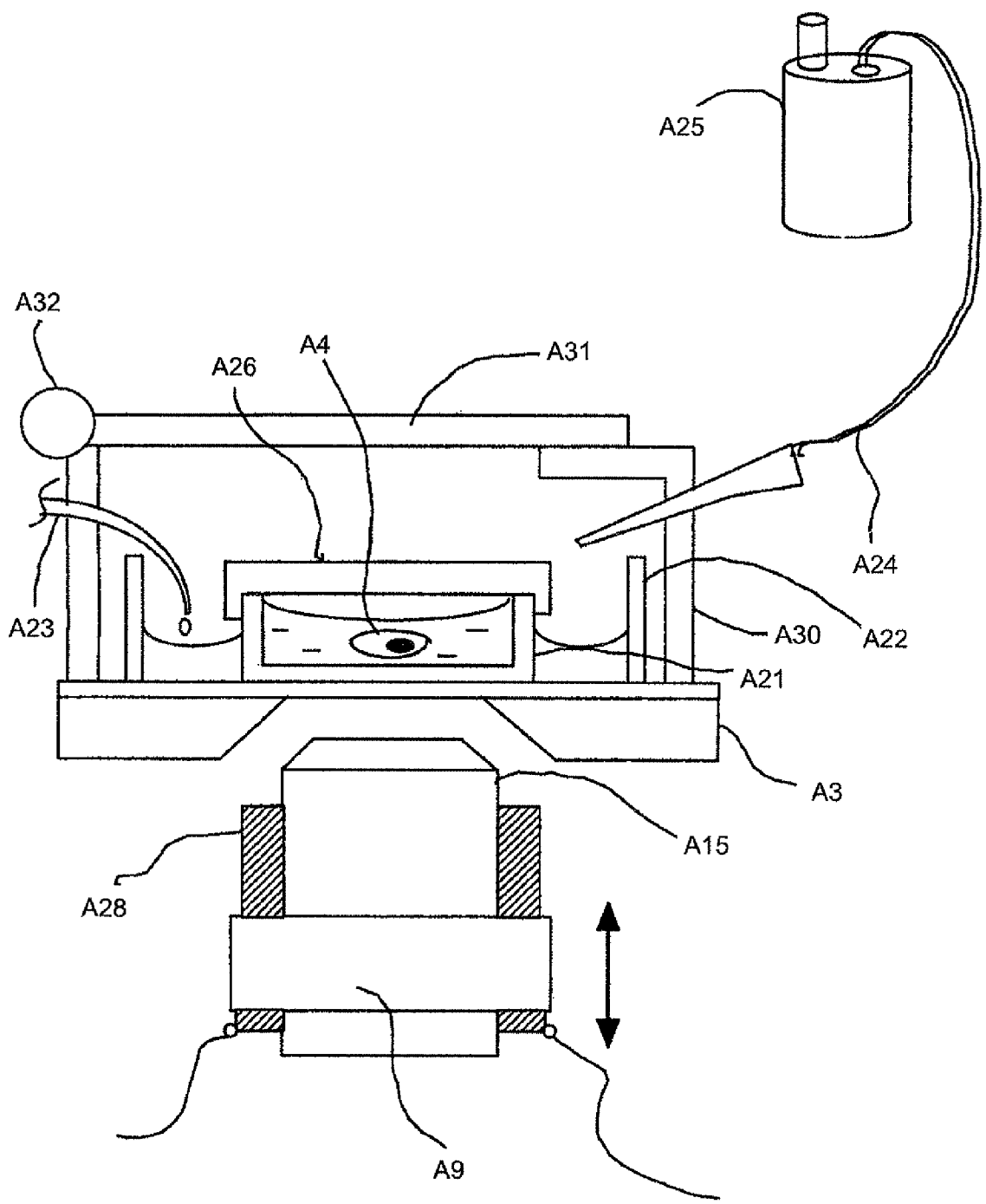
FIG. 37 is a view showing the structure in the vicinity of the specimen container involved with the first embodiment of the present invention.

The structure of the first embodiment will be explained with reference to FIGS. 36 and 37. FIG. 36 is a schematic view of a feeble light detecting apparatus with an inverted microscope as a base. The feeble light detecting apparatus includes a light source A2, an illumination optical system A1 that makes the light emitted from the light source A2 into parallel light and directs the parallel light to a test specimen A4, an observation optical system A5 for forming an image of the test specimen A4, an ocular lens A1 for magnifying the image of the test specimen A4 to be visually observed, and a CCD camera A8 having an imaging device A7 for imaging the image of the test specimen A4. A computer A16 that also serves as a television monitor is connected to the CCD camera A8 via a signal cable A100.

The illumination optical system A1 includes, in this order from the light source A2, a collector lens A10, a deflection mirror A12 for deflecting an optical axis A11 of the illumination light, and a condenser lens A14. The light source A2 uses an incoherent light source that emits light having a wavelength of visible light region, such as a halogen lamp, LED light source, tungsten lamp, mercury lamp, etc. Alternatively, light such as laser from a coherent light source that is changed into incoherent light with the use of a diffusion plate may be used as the light source. The wavelength of the light source generally employs visible light, but infrared ray may be used.

The observation optical system A5 includes, in this order from the side of the test specimen A4, an objective lens A15 for forming an image of the test specimen A4, a first relay lens A16, a deflection mirror A17 for deflecting the light from the objective lens A15, and a second relay lens A18 that images the image (image of the test specimen A4) of the objective lens A15 onto an imaging surface A19 with the first relay lens A16. A switching mirror A20 is arranged between the second relay lens A18 and the imaging surface A19 so as to optionally change the visual observation of the image of the test specimen A4 by the ocular lens A6 and the observation by the CCD camera A8. The switching mirror A20 may perform mechanical switching operation, and in addition to this type, an optical path may be separated by using a half mirror.

Figure 39:
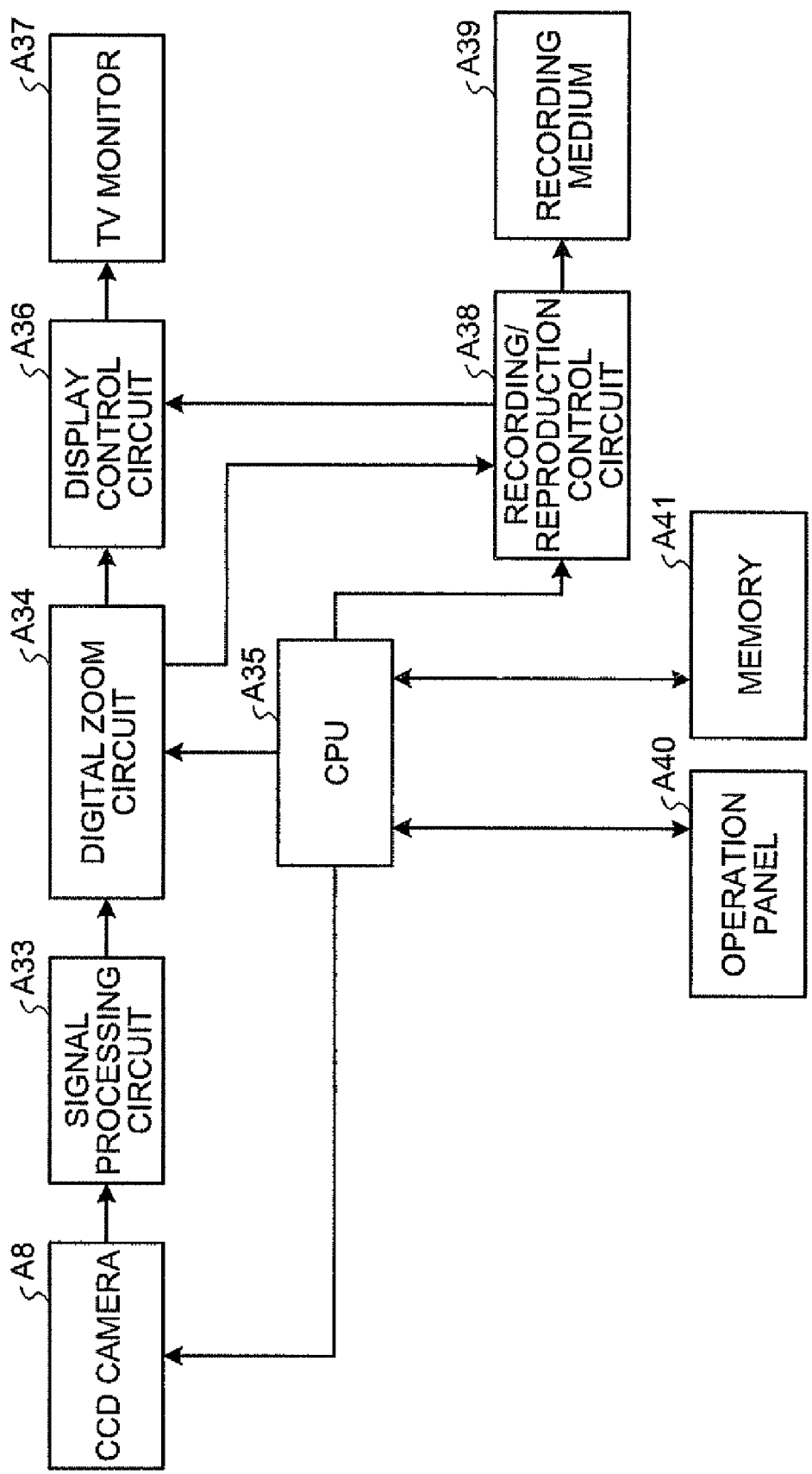
FIG. 39 is a block diagram showing the structure of the digital zooming involved with the first embodiment of the present invention.

Next, the structure of the feeble light detecting apparatus according to the present invention will be explained with reference to FIG. 37. The test specimen is put into a specimen container A21 such as a petri dish with culture solution. A water tank 22 is arranged around the specimen container A21, and pure water is supplied in the water tank A22 through a nozzle A23. The pure water is put into the water tank A22 in order to keep the humidity in the specimen container. A $CO_2$ gas is fed to the upper surface of the water tank A22 through a gas feed tube A24. The $CO_2$ gas is fed from a gas cylinder A25 arranged at the outside of the main body of the measurement apparatus. Refer to FIG. 39. The gas cylinder is filled with gaseous mixture having 5% of $CO_2$ and 95% of $O_2$. The $CO_2$ gas is fed from the gas cylinder A25 into a covered closed container A30, in which the specimen container A21 is put, through the gas feed tube A24 in a flow rate of 50 mL/min. The entire body of the specimen container is set onto a heat plate A27. The heat plate A27 can perform the setting of the environment temperature at 0.5° C. intervals thanks to the control of a temperature controller (not shown). The bottom surface of the specimen container A21 is made of a material same as a cover glass for a microscope, and has a thickness of 0.17 mm, whereby an ordinary objective lens can be used for the specimen container A21. The bottom surface of the specimen container A21 is optically transparent. A slide glass, microplate, or the like can be used as the specimen container A21 instead of the petri dish.

A specimen container cover A26 is arranged on the upper surface of the specimen container A21 so as to enclose the upper front surface of the specimen container A21. The specimen container cover A26 is made of an optically transparent synthetic resin such as an acrylic resin for preventing foreign matters such as dusts from entering the test specimen A4 in the specimen container A21. Further, the specimen container cover A26 is for preventing the test specimen A4 in the specimen container A21 from being evaporated. The specimen container A21 including the water tank 22 is housed in a covered closed container A30. The covered closed container A30 is made of an optically transparent synthetic resin such as an acrylic resin, and a cover A31 is mounted to the upper surface thereof with a hinge A32. The cover A31 is manually openable and closable with the hinge A32.

Two stepping motors (not shown) are mounted at the specimen stage A3 so as to direct in the different directions at an angle of 90°. Each of the stepping motors is connected to a specimen stage controller. The specimen stage controller is connected to the computer A16, whereby the specimen stage controller drives two stepping motors based on the instruction from the computer A16 so as to move the specimen stage A3 in the X-direction and Y-direction. The objective lens A15 is arranged below the specimen stage A3 so as to be inverted, and an objective lens heater A28 is arranged around the objective lens A15 so as to come into contact therewith. The objective lens heater A28 is connected to a temperature controller, which performs a temperature control at 0.5° C. intervals so as to make the objective lens keep the fixed temperature from the outside. An objective lens Z-axis driving mechanism A9 is mounted around the objective lens heater for automatically driving the objective lens A15 along the Z axis (in the direction of the optical axis). The objective lens Z-axis driving mechanism A9 moves the objective lens vertically by a rack-and-pinion mechanism (not shown). A turning operation of a knob of the rack-and-pinion mechanism is performed by a stepping motor (not shown) controlled by a computer. The objective lens Z-axis driving mechanism A9 may be operated not only by the rack-and-pinion mechanism but also by a friction roller.

A CCD (Charge Coupled Device) camera is used as a light-receiving device. The structure of the light-receiving device will be explained with reference to FIG. 36. The pixel number of an imaging device A7 on the light-receiving surface of the CCD camera A8 is 1,360×1,024. Since the light emitted from the test specimen is feeble, the CCD camera A8 as highly sensitive as possible is used as the light-receiving device. In order to prevent a dark current generated from the CCD camera A8, a cooling device A29 composed of a Peltier device is arranged at the bottom part of the CCD camera A8. The cooling device A29 cools the temperature of the CCD camera A8 to about 0° C. and keeps this temperature. An infrared ray cut filter A13 is arranged above the light-receiving surface of the CCD camera A8 for shielding infrared ray that is a background light. A TV monitor is connected to the CCD camera through a signal cable A100, so that an image of the specimen is described on the TV monitor. A three-plate color camera may be used as the CCD camera in order to image a color bright-field image.

The optical detector is not limited to the CCD camera. For example, a CMOS (Complementary Metal Oxide Semiconductor) image sensor or SIT (Silicon Intensified Target) camera may be used.

When a luminescent phenomenon due to bioluminescent protein is measured, the intensity of the luminescence is extremely feeble at the time of setting the specimen, so that the luminescence cannot be detected by the light-receiving device as an optical signal. Therefore, the internal structure of the cell cannot generally be observed. Specifically, the objective lens cannot be focused on a cell, which is a subject to be observed, in the specimen, while confirming the cell, like an ordinary observation with the use of a microscope. In view of this, in order to observe a bright field image, light from the light source such as a halogen lamp is irradiated to the test specimen through the illumination optical system to obtain the bright field image of the test specimen by the microscope, whereby the focal position of the objective lens is determined based on the bright field image. Specifically, in the observation of the bright field image, the substantial center between two positions of the objective lens on the optical axis where an image having a high contrast is obtained is defined as the focal position of the objective lens. Thus, when the intensity of the luminescence from the bioluminescent protein increases, a clear luminescent image focused on the CCD camera can be obtained. The focal position determining method of the objective lens has already been explained in detail in the previous embodiment.

Next, the operation of the optical system according to the first embodiment will be explained with reference to FIG. 36. The light from the light source A2 is made into parallel light by the collector lens A10, and projected onto the pupil position of the condenser lens A14. The image of the light source A2 illuminates the test specimen A4 by the condenser lens A14 as Koehler illumination. The light illuminating the test specimen A4 transmits the test specimen A4 to be incident on the objective lens A15. Then, the measurement light incident on the objective lens A15 forms an image of the test specimen A4 by the objective lens A51 the first relay lens A16 and the second relay lens A18 on the imaging surface A19. Here, the objective lens at ×20 is used.

The image of the test specimen A4 formed on the imaging surface A19 is incident on the ocular lens A6 as unchanged, and further imaged on the imaging device A7 of the CCD camera A8 by the switching mirror A20. The infrared ray cut filter A13 is arranged in front of the light-receiving surface of the CCD camera A8 for shielding infrared ray that is a background light. It is needless to say that the specimen stage A3 may be moved along the optical axis, without being limited to moving the objective lens.

Next, a digital zoom function will be explained with reference to a block diagram in FIG. 39. The image of the test specimen is input into the imaging unit A7 of the CCD camera A8, and converted into an analog electrical signal, i.e., an image signal. The converted image signal is input to a signal processing circuit A33 where image processing such as an amplifying process, filtering process, outline emphasizing process is performed. Then, the resultant signal is directed to a digital zoom circuit A34. The image signal is subject to A/D conversion by the digital zoom circuit A34 to generate a digital image signal, and a digital zoom processing is executed to the digital image signal according to a digital zoom control signal given from a CPU (Central Processing Unit) A35. The digital image signal subject to the processing is input to the TV monitor A37 through a display control circuit A36, whereby a magnified image of the test specimen is displayed on the screen of the TV monitor A37.

On the other hand, the digital image signal output from the digital zoom circuit is also input to the recording/reproduction control circuit A38. The recording/reproduction control circuit A38 records the input digital image signal on a detachable recording medium A39 inserted into a memory slot (not shown) based on the recording control signal given from the CPU A35. A memory card is used as the recording medium. The recording/reproduction control circuit A38 reads the digital image signal recorded on the recording medium A39 in response to the reproduction control signal given from the CPU A35. The read digital image signal is input to the TV monitor A37 through the display control circuit A36, whereby the image of the test object is displayed onto a screen of the TV monitor A37. The image may be recorded not only on the memory card but also on a recording medium such as a hard disk, magnetic disk, optomagnetic disk, or the like.

Figure 40:
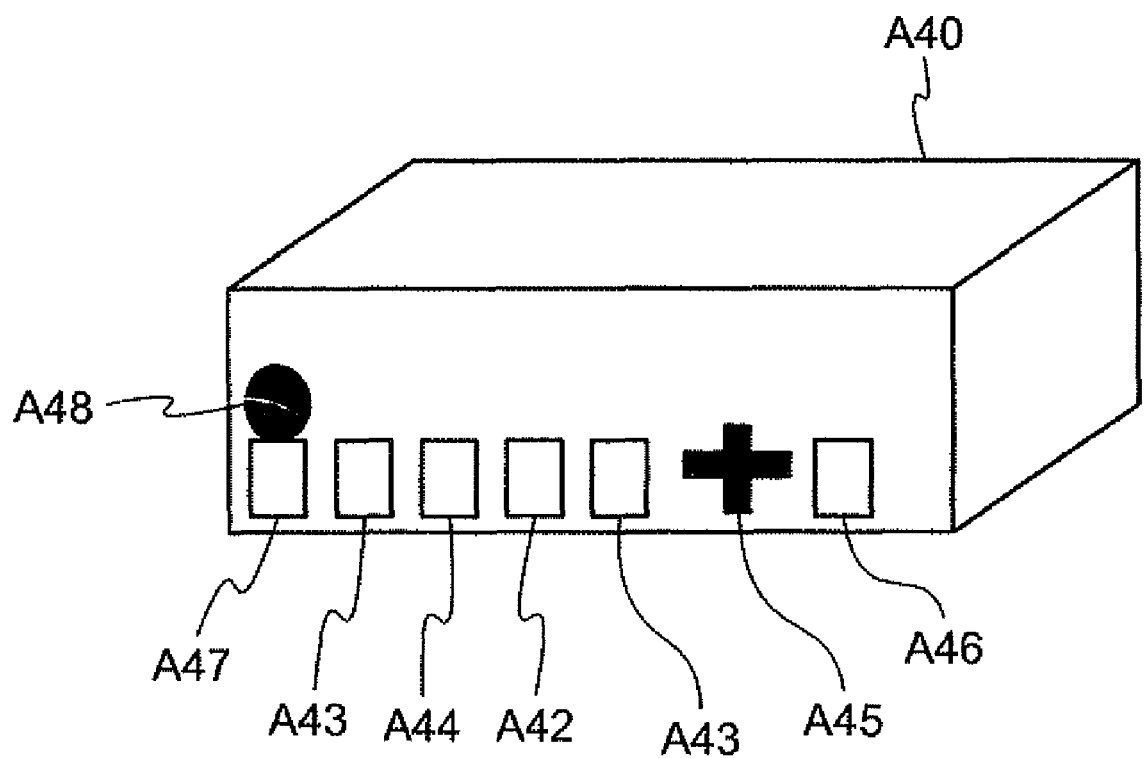
FIG. 40 is a view showing a structure of an operation panel of the digital zooming involved with the first embodiment of the present invention.

An operation panel A40 shown in FIG. 40 is connected to the CPU A35. A power supply switch A46 is provided to the operation panel A40 so as to turn on or off the power supply of the operation panel A40. The digital zoom control signal is supplied to the digital zoom circuit A34 through the CPU A35 from the instruction of the operation panel A40. In this case, the digital zoom control signal transmitted from the CPU A35 is a rectangular continuous pulse signal. A video recording button A42 and a reproduction button A43 are also provided to the operation panel A40. When the video recording button A42 is turned ON, the CPU A35 is in a video recording mode for generating a video recording control signal and supplying the same to the recording/reproduction control circuit A38. On the other hand, when the reproduction button A43 is turned ON, the CPU A35 is in a reproduction mode for generating the aforesaid reproduction control signal and supplying the same to the recording/reproduction control circuit A38. The control program for controlling the operation of the CPU A35 is stored in a memory A41.

By the depressing operation of these buttons, an operation substrate outputs an instruction signal corresponding to each button to the CPU A35 so as to adjust a zoom central position, zoom magnification, etc. In FIG. 40, a shutter button A48, zoom magnification button A43, zoom reduction button A44, and crosshair cursor button A45 are illustrated as examples, and other operation members are not shown.

As understood from the above explanation, the feeble light measuring apparatus according to the first embodiment has a digital zoom function in which a zoom magnification is adjustable by the digital process to the acquired image signal. The zoom magnification M by the digital zoom function is ×4.0 at a maximum. The digital zoom circuit A34 is controlled in accordance with the above-mentioned digital zoom control signal, whereby the zoom magnification M is changeable within the range of M=1.00~4.00. A known technique is used for the digital zoom circuit A34 performing the digital zoom function, so that the explanation thereof is omitted here.

The digital signal processing unit performs a digital process such as a gamma correction, as needed, to the image data input from an analog signal processing unit (A/D converter), and further, is used as image taking means for taking in the image data in a digital zoom area from the image data (image data in all pixel areas of the CPU) taken by the CCD based on the control signal from the CPU A35. Specifically, the control signal for controlling the zoom magnification and zoom central position is input from the CPU A35 to the signal processing unit, whereby the image data with the zoom magnification with the zoom central position defined as a center is segmented to form an image of one screen, and this image can be taken as the image in the digital zoom area.

In particular, in the digital signal processing unit, the taken image in the digital zoom area is output to a display memory to be capable of being displayed onto the TV monitor A37 in order to visually show the zoom central position and the zoom magnification to an operator. Thus, the user can know the zoom central position, and further, can move the zoom central position by depressing the crosshair cursor button A45, whereby the user can designate the zoom central position at a desired position. The digital zoom area is changed by depressing the zoom magnification button A43 and the zoom reduction button A44, whereby the desired zoom magnification can be designated.

The memory card A39 records and stores the image data. As shown in FIG. 40, when a mode switch A47 is in an imaging mode and an instruction for recording an image is given by depressing the shutter button A48, the CPU A35 outputs a control signal to the digital signal processing unit, so that the image data of one frame is read from the CCD, the digital signal processing is performed to the image data at the digital signal processing unit, and then, this image data is written in the memory A41. The image data written in the memory A41 is compressed by a compression circuit to be recorded and stored in the memory card A39 by the recording/reproduction control circuit A38.

The method of zooming of the displayed image is not limited to a digital zooming. An optical zooming may be performed. The optical zooming is performed by a zoom lens. As is conventionally performed, the optical zooming is executed in such a manner that a focal distance between the CCD camera and the second relay lens is moved along the optical axis by a motor driving caused by a stepping motor. The zooming lens is composed of a three-variable lens group, a correction lens group for compensating aberration, and a focus lens for adjusting a focus. The focal distance of the lens can manually or automatically be changed in ten steps. The zoom lens is driven by an operation of a zoom motor attached around the zoom lens. An ultrasonic motor or the like is used as the zoom motor for moving the lens along the optical axis based on the control signal transmitted from the CPU A35.

Second Embodiment

Simultaneous Measurement of Fluorescence and Bioluminescence

Figure 41:
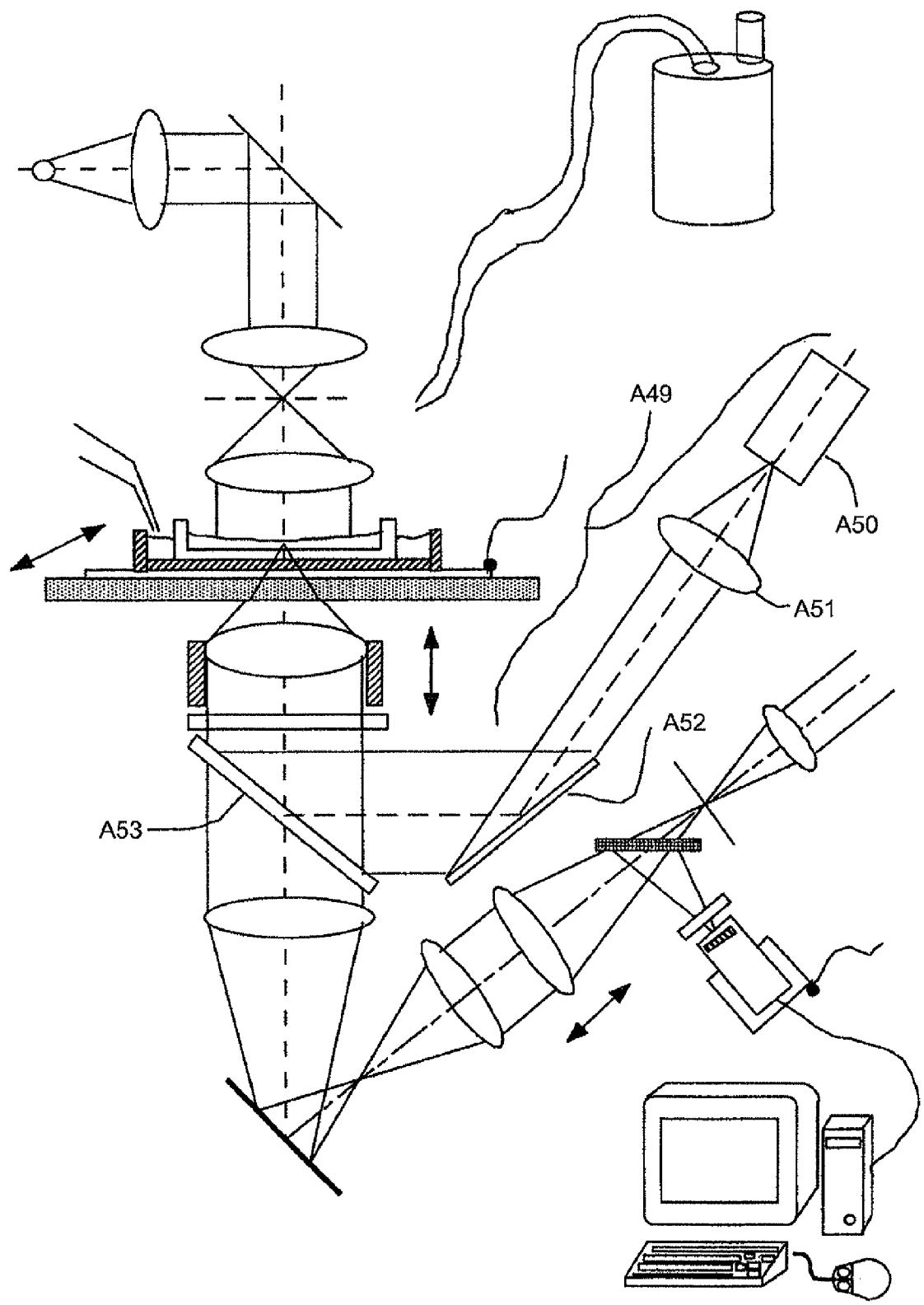
FIG. 41 is a view showing a structure of the optical system involved with the second embodiment of the present invention.

An optical system of a feeble light detecting apparatus that can simultaneously execute digital zooming and optical zooming and simultaneously measure fluorescence and bioluminescence is schematically shown in FIG. 41. The structure and the operation of the optical system are basically the same as those explained in the first embodiment in FIG. 36 except that an exciting optical system A49 is added. The optical system basically has a structure with an inverted optical microscope as a base. It includes an illumination light source, specimen stage, objective lens, and computer. The optical system is composed of an illumination optical system A1 for guiding light to the test object A4 in the specimen container A21 such as the petri dish, and an observation optical system A5 for guiding the feeble light emitted from the test object A4 to the CCD camera A8.

The exciting optical system A49 includes an exciting light source A50, collimator lens A51, deflection mirror A52 and a switch-type dichroic mirror A53. A gas laser in a visible region such as argon laser, helium-neon laser, etc. is used for the exciting light source. The switch type dichroic mirror A53 has a spectral characteristic of reflecting light having an oscillation wavelength of the exciting light source and transmitting the spectrum of the fluorescent signal and the luminescent signal.

The exciting light source A50 is provided at the outside of the main body. The exciting light source A50 is argon laser having a wavelength of 488 nm and output of 10 mW. The laser beam is converted into a circular parallel flux having a beam width by the collimator lens, reflected by the deflection mirror A52, and incident on the switch-type dichroic mirror A53 arranged at the observation optical system A5. The laser beam incident on the observation optical system A5 is reflected by the switch-type dichroic mirror A53 to be incident on the objective lens A28 from below, and then, converged to the test specimen A4 in the specimen container A21 to irradiate the same. The switch-type dichroic mirror A53 is housed in a holder (not shown) so as to be replaceable according to the oscillation wavelength of the excited laser beam. If it is unnecessary to change the wavelength of the exciting light source A50, the switch-type dichroic mirror A53 may not be used, but an ordinary dichroic mirror may be fixed to be arranged in the observation optical system A5.

In order to obtain an image of a cell, an objective lens having the NA (numerical aperture) of about 0.9 is used (in the air). An objective lens having the NA of not less than 1.0 is used to a test specimen immersed into liquid. The fluorescent signal or luminescent signal transmitted from the test specimen A4 passes through the observation optical system A5 in the main body of the apparatus through the objective lens A15 to reach the switch-type dichroic mirror A53. Then, the signal passes through the switch-type dichroic mirror A53, passes through the first relay lens A16 and the second relay lens A18, is reflected on the switching mirror A20, and imaged on the light-receiving surface of the imaging unit A7 in the CCD camera A8.

The fluorescent signal or luminescent signal transmitted from the test specimen reaches the ocular lens AG after imaging on the imaging surface A19, when the switching mirror A20 is removed from the optical path/whereby an operator can directly observe the image.

The optical signal from the CCD camera A8 is transmitted to the computer A16 arranged at the outside of the feeble light detecting apparatus, wherein the computer A16 describes and analyzes the luminescent image, measures the intensity of the luminescence over time, and analyzes the signal. The result of the analysis is displayed onto a monitor screen of the computer A16. Specifically, the computer A16 not only describes the image of the specimen, but also analyzes the change over time of the intensity of the luminescence.

Rohdamine Green (RhG) is used as a fluorescent pigment. Instead of Rhodamine Green (RhG), usable fluorescent materials include TMR (Tetramethylrhodamine), 5-Tamra (5-carboxytetramethylrhodamine), etc. In this case, in order to excite the fluorescent material TMR, argon laser having a wavelength of 514.5 nm is used as the excited laser light source, while He.Ne laser having a wavelength of 543.5 nm is used as the excited laser light source in order to excite a fluorescent material 5-Tamra. In addition, FITC (Fluorescein-I-sothiocyanate), TOTO 1, Acridine-Orange, Texas-Red, etc. are used as the fluorescent pigment.

Figure 42:
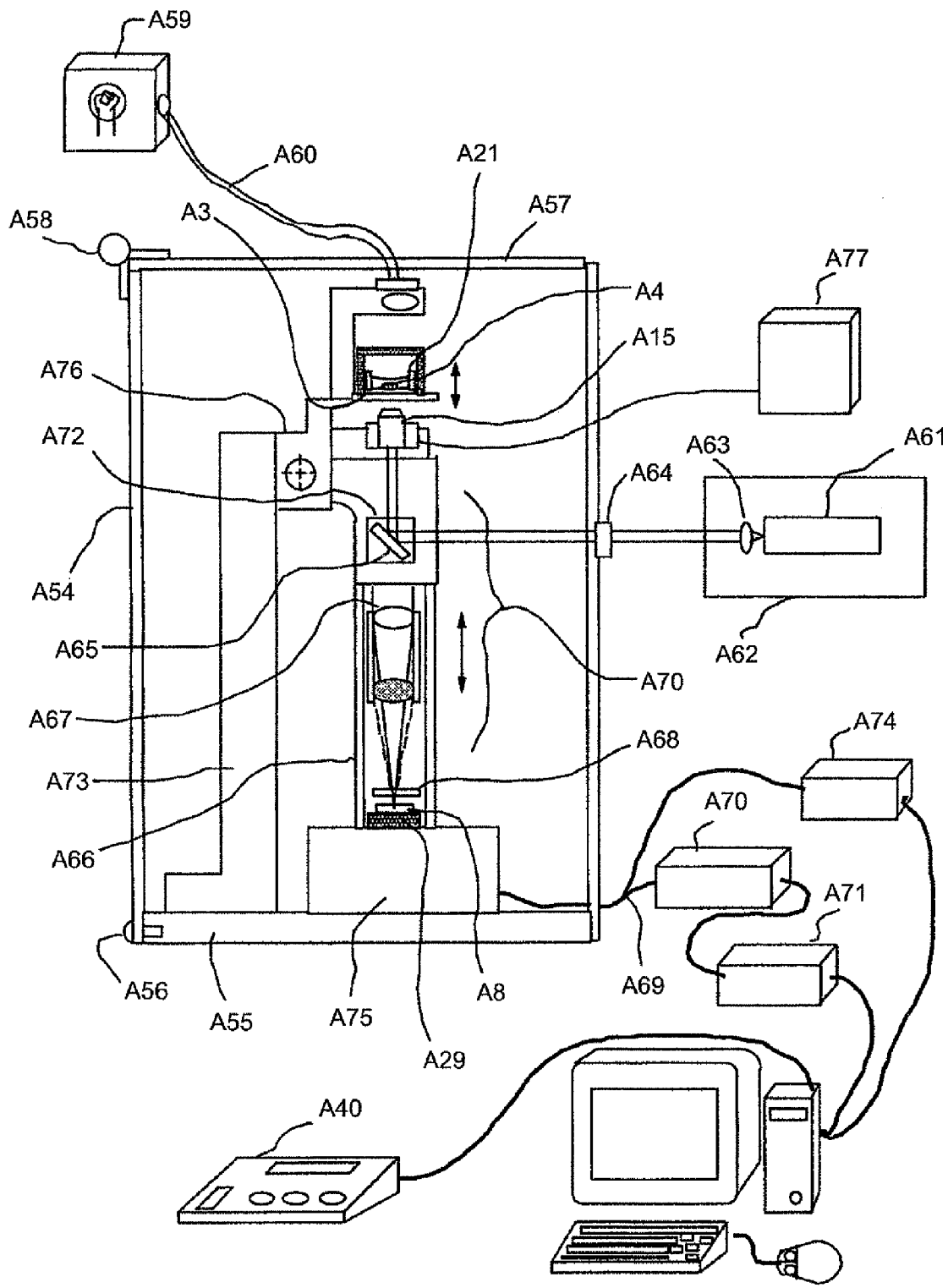
FIG. 42 is a view showing a configuration of an apparatus according to a modification of the second embodiment of the present invention.

FIG. 42 shows an embodiment of a feeble light detecting apparatus that can simultaneously execute a digital zooming and optical zooming, and simultaneously measure fluorescence and bioluminescence. The main body of the measurement apparatus is housed in a light-shielding box A54 obtained by painting a surface of a metal plate, such as aluminum, with black and assembling the resultant in a box shape. The main body of the measurement apparatus is fixed to a bottom plate A55 by a fixing member A56. The light-shielding box A54 has a light-shielding cover A57 separately mounted on the upper surface thereof. One end of the light-shielding cover A57 is coupled to the light-shielding box A54 with a hinge A58 in such a manner that the light-shielding cover A57 can manually or automatically be opened or closed in a sector manner.

An incoherent light source such as a halogen lamp or metal halide lamp is used as the illumination light source. The illumination light source is arranged in a light source box A59. Illumination light is directed from the upper surface of the specimen container A21 on the specimen stage A3 from the light source box A59 through an illumination optical fiber A60 so as to illuminate the entire test specimen A4. The observation optical system receives a signal light converged by the objective lens A15 and emitted from the test specimen A4 by the CCD camera A8 via the lens A67 without using the deflection mirror used in the first embodiment.

The laser light source A61 is fixed in the exciting light source box A62 at the outside of the main body of the feeble light measuring apparatus. The laser beam emitted from the laser light source A61 is made into a parallel flux whose beam width is enlarged by the collimator lens A63 that is mounted and fixed in the exciting light source box A62, and introduced in the main body of the apparatus through a circular laser inlet port A64 formed at the light-shielding box A54. Argon laser having a wavelength of 488 nm and output of 10 mW is used as the laser light source A61. The laser beam incident on the main body of the feeble light measuring apparatus through the laser inlet port A64 reaches the switch-type dichroic mirror A65, is reflected by the dichroic mirror A65 to be incident on the objective lens A15 from below, and is converged onto the test specimen A4 for irradiating the same. The switch-type dichroic mirror A65 has an optical characteristic of including a wavelength region of the exciting light source, reflecting light having a wavelength region shorter than this wavelength region, and transmitting light having a wavelength region longer than the wavelength region of the exciting light source. The switch-type dichroic mirror A65 is housed in a holder A72 in a lens barrel A70. The switch-type dichroic mirror A65 mounted in the holder A72 is arranged so as to be replaceable according to the oscillation wavelength of the excited laser beam.

The lens barrel A70 is divided into a lens barrel upper part A78 and a lens barrel lower part A66. The lens barrel upper part A78 and the lens barrel lower part A66 are coupled to each other. The lens barrel upper part A78 is held at a column A73 through a lens barrel Z-axis driving mechanism A76. The lens barrel upper part A78 can vertically move along the optical axis by the driving operation of the lens barrel Z-axis driving mechanism A76. The lens barrel Z-axis driving mechanism A76 can vertically move the lens barrel upper part A78 along the optical axis by a rack-and-pinion mechanism.

A lens A67 is arranged in the lens barrel lower part A66 mounted to the main body of the feeble light measuring apparatus, and the CCD camera A8 is mounted in such a manner that the substantial center of the light-receiving surface is matched to the focal position on the Z axis. The lens A67 is a zoom lens. Since the operation of the zoom lens has already been described in the first embodiment, the explanation thereof is omitted. Since the light emitted from the specimen is feeble, a CCD camera as highly sensitive as possible is used as the CCD camera A8. The pixel number of the CCD camera A8 is 1,360×1,024. In order to prevent a dark current generated from the CCD camera A8, the cooling device A29 composed of a Peltier element is arranged at the bottom part of the CCD camera A8. The cooling device A29 cools the temperature of the CCD camera A8 to about 0° C. and keeps this temperature. An infrared ray cut filter A68 is arranged above the light-receiving surface of the CCD camera A8 for shielding infrared ray that is a background light. When the infrared ray is taken as a signal light, the infrared ray cut filter A68 is removed from the lens barrel lower part A66 before the measurement. A focus detector, a position detector, and a computer A16 are connected to the output unit of the CCD camera A8 via a signal cable A69, and the image of the specimen is described on a TV monitor A72 attached to the computer A16. A three-plate color camera may be used as the CCD camera in order to image a color bright-field image. The main body rack can make the Lens barrel A70 slidably move vertically so as to perform positioning.

The specimen container A21 is fixed by a locking pin (not shown) on the XY specimen stage A3. The XY specimen stage can freely move on the XY plane along the XY plane by the rack-and-pinion mechanism. The objective lens A15 is arranged below the specimen container A21. The objective lens A15 is attached to the objective lens Z-axis driving mechanism A9 so as to be movable along the optical axis (Z axis). The objective lens Z-axis driving mechanism A9 is connected to the focus detector A70, which is mounted at the outside of the feeble light detecting apparatus by a lead wire 69, and further connected to the position detector A71 from the focus detector A70, whereby the output signal from the position detector A71 is output to the TV monitor A72 attached to the computer A16. On the other hand, the lead wire A69 is branched, wherein the output signal of the CCD camera A8 is guided to a signal processing unit A74, while the output signal from the signal processing unit A74 is connected to the computer A16.

The fluorescent signal or luminescent signal emitted from a cell transmits the objective lens A15 and the switch-type dichroic mirror A65, passes through the lens A67 mounted to the lens barrel lower part A66, and is converged onto the light-receiving surface of the CCD camera A8.

The main body of the feeble light measuring apparatus is fixed onto a base rack A75. The base rack A75 is mounted to the column A73, whereby the base rack A75 is vertically movable. The lens barrel lower part A66 is fixed to the base rack A75 by a fixing member (not shown). The column A73 and the base rack A75 are fixed on a bottom plate A55.

Next, the operation will be explained. The signal of the illumination image of the test specimen, obtained from the CCD camera A8 by the illumination light source, is directed to the signal processing unit A74, where an output intensity signal from each pixel is statistically processed to obtain an optical signal intensity distribution. The objective lens Z-axis driving mechanism A9 is operated so as to move the objective lens A15 along the optical axis by an appropriate amount in interlocking with the objective lens Z-axis driving mechanism A9. The objective lens Z-axis driving mechanism A9 is connected to an objective lens driving device A77 via a signal cable, whereby the objective lens Z-axis driving mechanism A9 is operated based on the instruction from the objective lens driving device A77 so as to automatically move the objective lens A15 vertically.

The optical output signal from the CCD camera A8 is analyzed at the signal processing unit A74 for every moving step of the objective lens A15 so as to detect the position of the objective lens A15 on the optical axis where an image having a high contrast is obtained. Vertically two positions of the objective lens A15 on the optical axis where images having a high contrast are obtained are found, and the substantial central position between the vertically two positions is defined as the luminescent position of the test specimen A4 as a result of the calculation at the signal processing unit A74. Then, the objective lens Z-axis driving mechanism A9 is operated to move the objective lens A15 to this position. Thus, the focal position of the objective lens A15 is determined. Therefore, the objective lens A15 is fixed on this position, and the fluorescent signal and luminescent signal transmitted from the test specimen A4 are received by the CCD camera A8. The focal position determining method of the objective lens has already been described in detail in the previous embodiment.

The objective lens A15 is replaceably attached to the objective lens Z-axis driving mechanism A9. When the magnification of the objective lens A15 is increased to image the test specimen A4, the obtained image is darkened. The test specimen A4 such as a cell moves in a culture solution. When this is observed with an objective lens having a high magnification, a field of view becomes narrow, and according to the situation, the test specimen A4 might move out of the field of view. Therefore, the test specimen A4 is firstly observed with the objective lens having a low magnification at ×10 or ×20. The desired position of the test specimen A4 is confirmed, and then, the desired position is designated and the image of the specimen is zoomed up with the use of a mouse or keyboard. Alternatively, a threshold is determined to binalize the light intensity of the luminescent portion and other portion in the luminescent image for obtaining the luminescent area, and this area may be zoomed up.

The signal processing unit A74 may be omitted, and the computer A16 may serve as the signal processing unit A74.

The objective lens Z-axis driving mechanism A9 is connected to the focus detector A70 mounted at the outside of the feeble light detecting apparatus through the lead wire A69, and is connected to the position detector A71 from the focus detector A70, whereby the output signal from the position detector A71 is output to the TV monitor.

Measuring Procedure

1) The measuring procedure for performing either one of a digital zoom or optical zoom will be described below.

Figure 38:
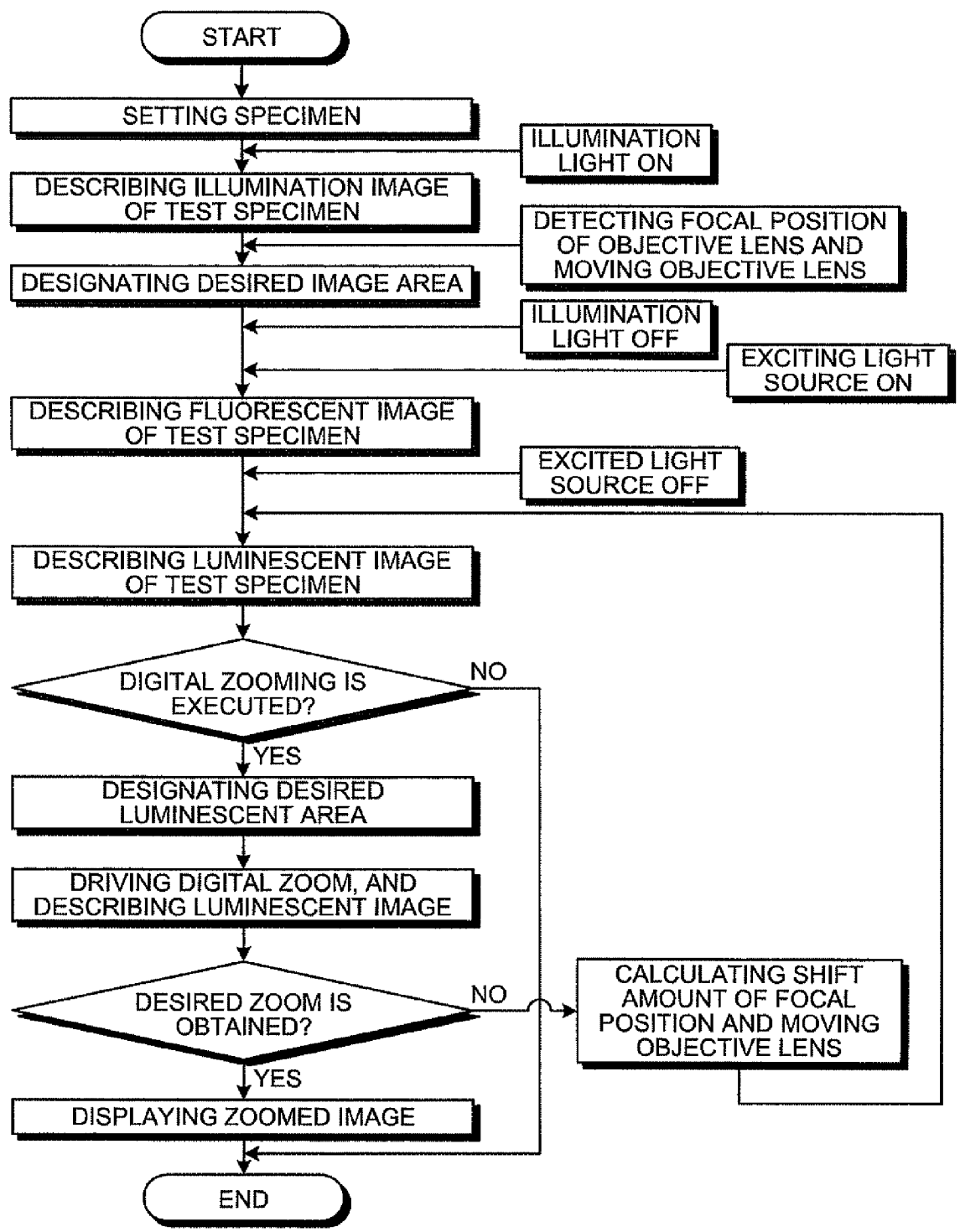
FIG. 38 is a flowchart showing an operation of a digital zooming involved with the first embodiment of the present invention.

FIG. 38 is a flowchart for performing the digital zoom.

1. A test specimen (cell) is immersed into a petri dish (specimen container) containing culture solution.

2. Illumination from the light source is started.

3. The power supply of the light-receiving device is turned on to describe an image of the test specimen (cell). The focal position of the test specimen is determined by the focal position determining method and apparatus, and then, the objective lens is moved to the focal position.

4. A desired area is designated in the obtained image.

5. The illumination from the light source is ended.

6. The exciting light source is turned on.

7. The fluorescent image of the test specimen (cell) is described.

8. The power supply of the exciting light source is turned off.

9. The luminescent image of the test specimen (cell) is described.

10. When the digital zooming is performed, a desired luminescent area is designated.

11. The digital zoom is started.

12. When a desired zoomed image is obtained by performing the digital zooming, the focal position determining operation of the objective lens is executed to move the objective lens to the focal position of the test specimen. Thereafter, the image is displayed on the TV monitor or input to a memory card. When a desired zoomed image cannot be obtained by performing the digital zooming, the luminescent area is again designated. Alternatively, the shift amount of the focal position is calculated from the digital image analysis, and the objective lens is moved to the corrected position according to the shift amount. Then, the procedure returns to 9.

13. End.

When the overlapping of the fluorescent image is unnecessary, the fluorescent material labeled at the desired region in the cell by the exciting light source is not excited. In the case of only the luminescent image, the focal position of the objective lens is detected, and the objective lens is moved to the focal position so as to perform the digital zooming, optical zooming, or both of the digital zooming and optical zooming in the same manner. The focal position of the test specimen may be determined after the desired area is designated in the obtained image, i.e., after 4., with the focal position determining method and apparatus. As needed, the focal position determining operation of the objective lens may be performed once at either 3. or at 12.

2) The measurement procedure for simultaneously performing the digital zooming and the optical zooming will be described below.

Figure 43:
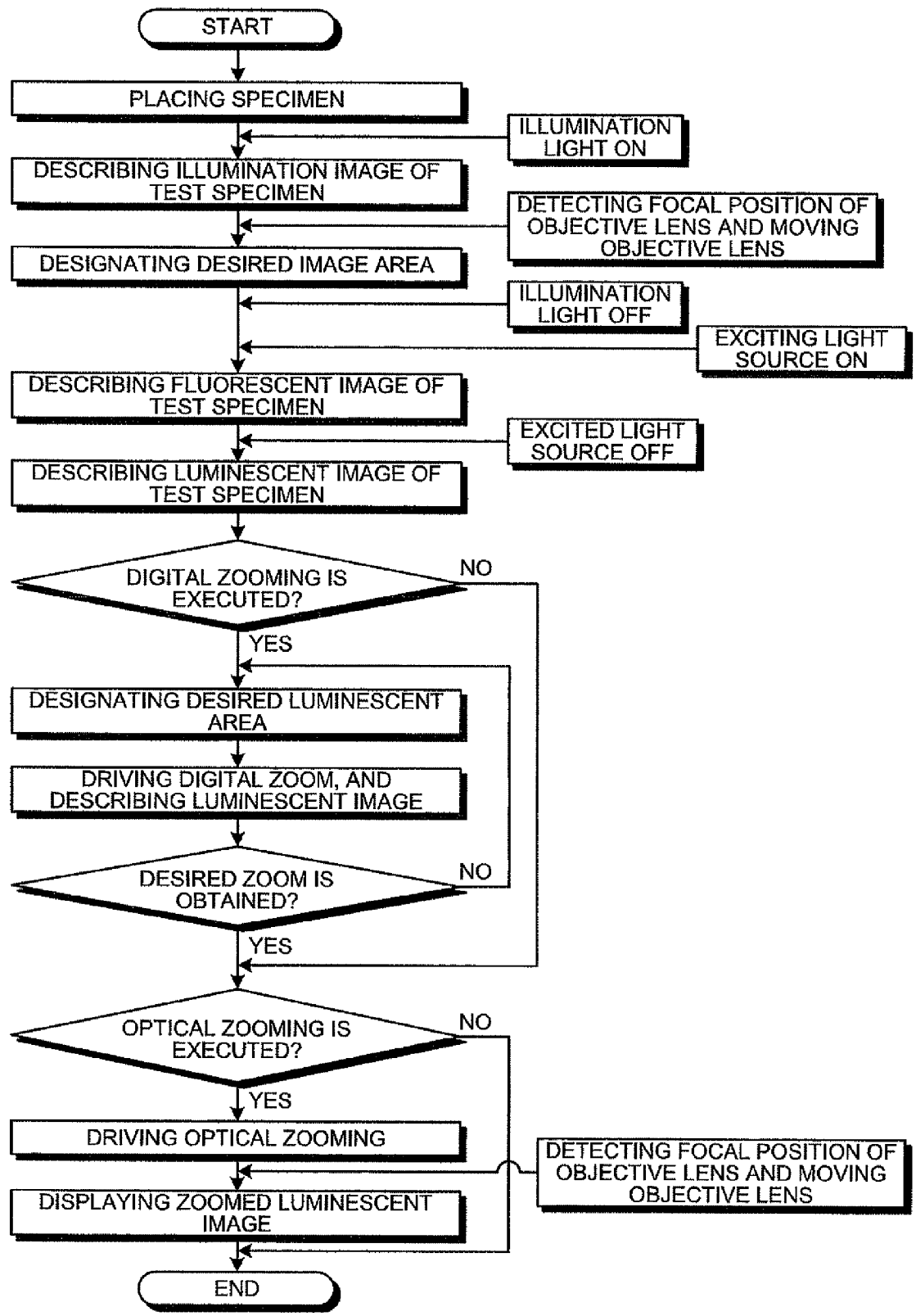
FIG. 43 is a flowchart showing a zooming operation involved with the second embodiment of the present invention.

FIG. 43 is the flowchart.

1. A test specimen (cell) is immersed into a petri dish (specimen container) containing culture solution.
2. Illumination from the light source is started.
3. The power supply of the light-receiving device is turned on to describe an image of the test specimen (cell). The focal position of the test specimen is determined by the focal position determining method and apparatus, and then, the objective lens is moved to the focal position.
4. A desired area is designated in the obtained image.
5. The illumination from the light source is ended.
6. The exciting light source is turned on.
7. The fluorescent image of the test specimen (cell) is described.
8. The power supply of the exciting light source is turned off.
9. The luminescent image of the test specimen (cell) is described.
10. A desired luminescent area is designated.
11. The aforesaid steps 10. to 12. in the aforesaid measurement procedure 1) are performed when the digital zooming is carried out. In this measurement procedure 2), the shift amount is not calculated, and when an operator determines that the desired image cannot be obtained by the image provided by the digital zooming, the optical zooming operation (the movement of the zoom lens A67 in FIG. 42) is performed to describe (display) the luminescent image.
12. The optical zooming is operated. The focal position determining operation of the objective lens is executed to move the objective lens to the focal position of the test specimen.
13. End. The focal position of the test specimen may be determined after the desired area is designated in the obtained image, i.e., after 4., with the focal position determining method and apparatus. As needed, the focal position determining operation of the objective lens may be performed once at either 3. or at 12.

When the overlapping of the fluorescent image is unnecessary, the fluorescent material labeled at the desired region in the cell by the exciting light source is not excited. In the case of only the luminescent image, the focal position of the objective lens is detected, and the objective lens is moved to the focal position so as to perform the digital zooming, optical zooming, or both of the digital zooming and optical zooming in the same manner. After executing the digital zooming and the optical zooming, a clearer image can be obtained in the desired region in the specimen by further performing the focal position determining operation of the objective lens.

The present invention has been explained with the embodiments. The present invention includes all inventions derived from the aforesaid explanation, and further includes the equivalent thereof. Moreover, the present invention is not limited to the above-mentioned embodiments. Various modifications are possible, and the present invention includes designed products, manufactured products and methods thereof. In the second embodiment, the luminescent amount with the digital zoom image is measured, and further, the observation image by an optical zoom image can be obtained. When the digital image and the optical image are both employed, a clear luminescent image with high magnification can be described, while measuring the continuous luminescent amount with a lapse of time.

Different from fluorescence, a luminescent image that is extremely feeble such as bioluminescence requires long image forming time in which the accumulation time for exposing a luminescent signal, which is required for the image formation, for a predetermined time is long such as 10 to 60 minutes, depending upon the type of the test specimen. When the magnification is increased only for performing the optical zooming, an exposure time longer than that in the case of the low magnification is required. Accordingly, when a feeble luminescent image is to be obtained by the optical zooming, the exposure time double that in the case of low magnification or longer is required in the case of high magnification, so that it takes much time for only forming an image. On the other hand, when an image is taken with a lapse of time, it is necessary to obtain a feeble light image magnified in a time as short as possible, since the image cannot be taken in an exposure time longer than the imaging interval. It is preferable that the digital zooming is executed as the number of the test specimen to be imaged is increased.

Different from the optical zooming, a magnified image can quickly be obtained from the digital zoom image only by digitally magnifying the image that has already been acquired. Therefore, a desired region can be designated at any time during the monitoring of the images one by one with low magnification, and its magnified image can be displayed together with the image before the magnification.

Example

In the present example, the objective lens was focused on plural HeLa cells in which plasmid vector was transduced, the HeLa cell, which was the subject, was selected from the plural HeLa cells, and the luminescent amount and ATP amount from mitochondria in the selected HeLa cell were measured over time, by using the focal position determining apparatus 1 according to the second embodiment. The experiment in the present example was performed according to the (step 1) to (step 7) described below.

(Step 1) A fusion gene in which fluorescent protein (GFP), mitochondria localization signal, and luciferase were combined was prepared.

(Step 2) A plasmid vector having the fusion gene therein was transduced to a HeLa cell.

Figure 23:
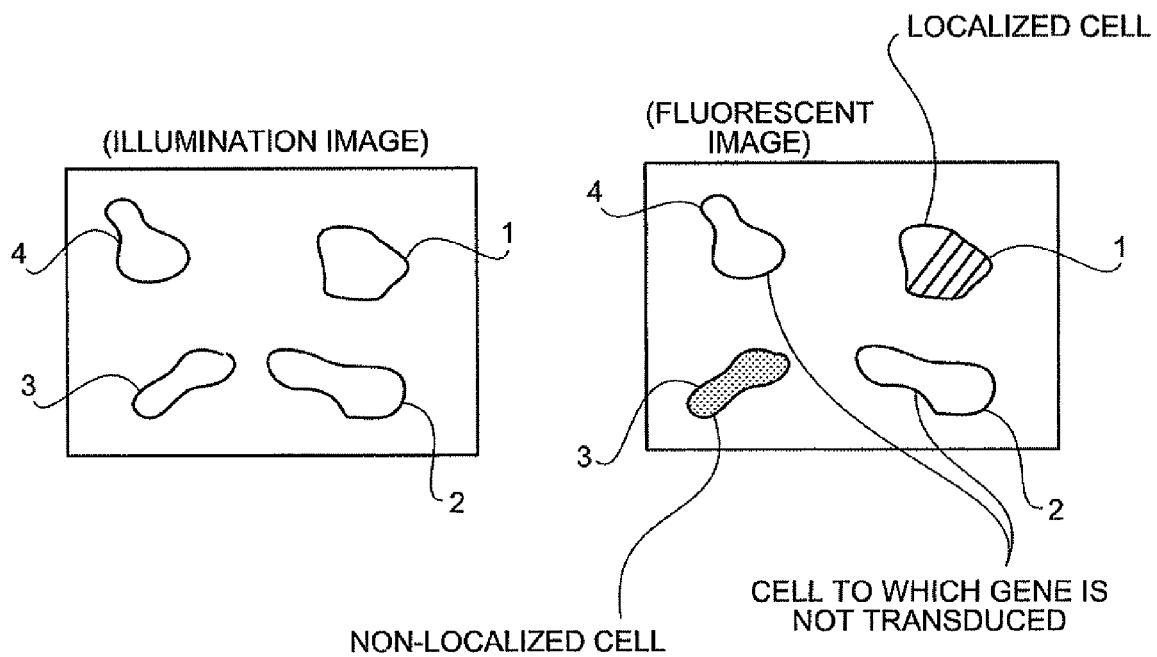
FIG. 23 is a view showing an illumination image and a fluorescent image of a HeLa cell transduced with plasmid vector.

(Step 3) With the use of the focal position determining apparatus 1, the focal position of the objective lens was adjusted to the mitochondria in the HeLa cell, and the HeLa cell was imaged by the CCD camera with the illumination and without the illumination. Then, it was determined whether SFP was localized in mitochondria or not based on the imaged images (fluorescent image) so as to confirm whether luciferase was localized or not in mitochondria (see FIG. 23). FIG. 23 is a view showing the illumination image and fluorescent image of the HeLa cell having plasmid vector transduced thereto.

(Step 4) Histamine was administered to the HeLa cell to cause the variation in the ATP amount in mitochondria via $Ca^{2+}$.

Figure 24:
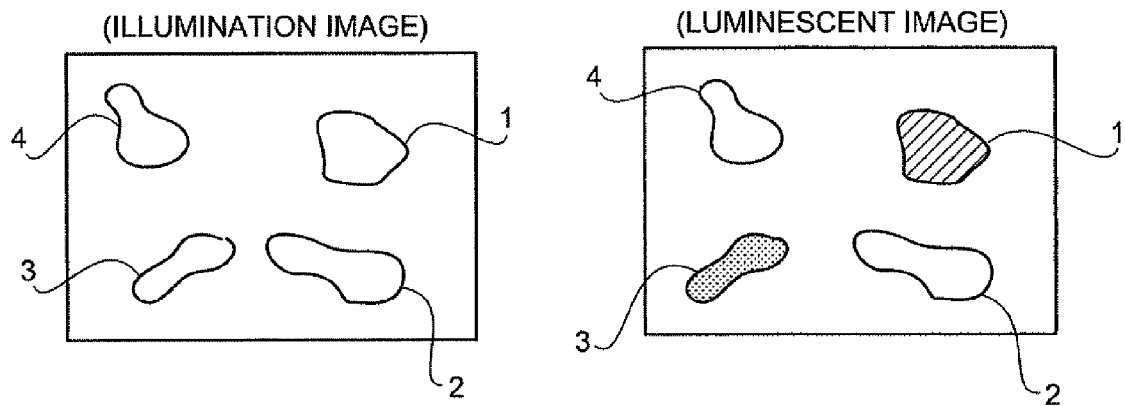
FIG. 24 is a view showing an illumination image and a luminescent image of a HeLa cell transduced with plasmid vector.

(Step 5) The HeLa cell was imaged with the illumination and without the illumination by the CCD camera, so that luminescent images in which luminescence from mitochondria in the HeLa cell was caught were obtained over time (see FIG. 24). FIG. 24 is a view showing the illumination image and luminescent image of the HeLa cell having plasmid vector transduced thereto.

(Step 6) The imaged illumination image, fluorescent image, and the luminescent image were overlapped with one another so as to select the subject HeLa cell.

(Step 7) The variation over time in the intensity of the luminescence from mitochondria in the selected HeLa cell was measured, and further, the variation over time in the ATP amount was monitored.

Figure 25:
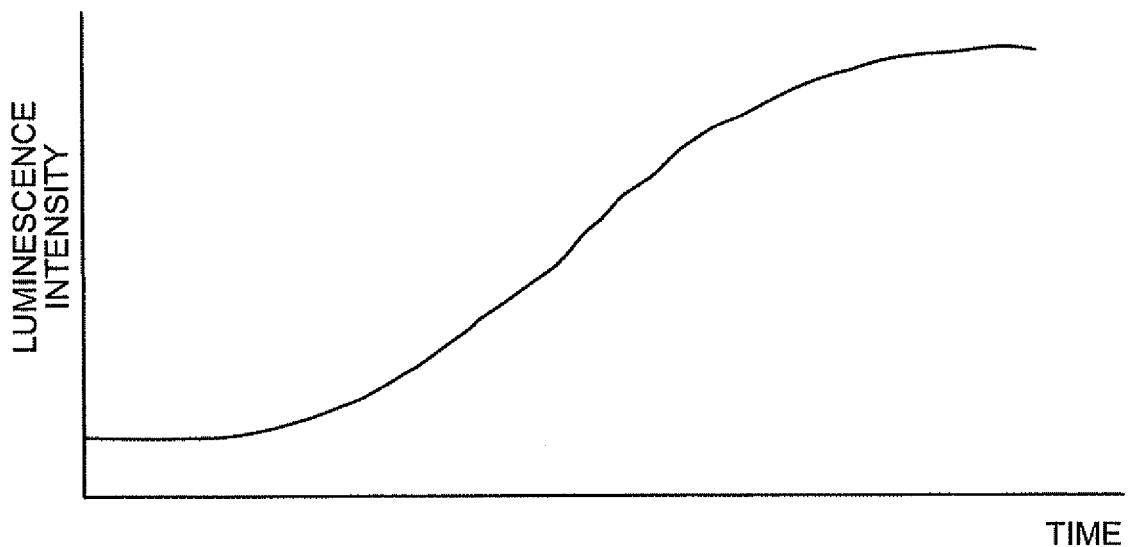
FIG. 25 is a graph showing a change, over time, of a luminescent intensity from the selected HeLa cell of No. 1.

The result of the experiment will be next explained. As shown in FIG. 23, it was confirmed that in the HeLa cell of No. 1, the fusion gene was transduced by plasmid vector and luciferase was localized in mitochondria. It was confirmed that, in the HeLa cell of No. 2 and the HeLa cell of No. 4, the fusion gene was not transduced by plasmid vector. Further, it was confirmed that, in the HeLa cell of No. 3, the fusion gene was transduced by plasmid vector, but luciferase was not localized in mitochondria. Specifically, the HeLa cell that was confirmed to have the fusion gene transduced by plasmid vector and have luciferase localized in mitochondria was only the HeLa cell of No. 1. Therefore, the HeLa cell of No. 1 was selected as the subject HeLa cell. As shown in FIG. 24, it was confirmed that the intensity of the luminescence from the HeLa cell of No. 3 was the greatest, the intensity of the luminescence from the HeLa cell of No. 1 was the second greatest, and the intensity of the luminescence from the HeLa cell of No. 2 and the HeLa cell of No. 4 were almost equal to each other. As shown in FIG. 25, the variation over time in the intensity of the luminescence from mitochondria in the HeLa cell of No. 1 could be monitored. FIG. 25 is a view showing a variation over time of the intensity of the luminescence from the selected HeLa cell of No. 1.

(I) The focal position determining method according to the present invention measures any one of the focal position of the objective lens at the near point and the focal position of the objective lens at the far point or both, and determines the focal position of the objective lens focused on the observed target region based on the measured focal position. When the specific region in the specimen is defined as the observed target region, and the luminescence of the observed target region is observed, the focal position of the objective lens focused on the observed target region can be determined at the time of setting the specimen, and therefore, the focal position of the objective lens can be focused on the observed target region. Further, the present invention provides an effect that, when the luminescent region in the specimen is observed, the objective lens can be focused on the luminescent region in the specimen without confirming the luminescence from the luminescent region.

The focal position determining method and focal position determining apparatus according to the present invention (1) irradiate light to the specimen, (2) change the focal position of the objective lens, (3) measure the changed focal position, (4) image the specimen to which the light is irradiated, at the changed focal position, (5) calculate feature data characterizing the imaged image based on the imaged image, (6) repeat the processes at (2) to (5), (7) select at least one focal position from the plural focal positions accumulated by the execution based on the plural feature data accumulated by the execution, (8) determine the focal position of the objective lens focused on the observed target region in the specimen based on the selected focal position. When the specific region in the specimen is defined as the observed target region, and the luminescence of the observed target region is observed, the focal position of the objective lens focused on the observed target region can be determined at the time of setting the specimen, and therefore, the focal position of the objective lens can be focused on the observed target region. Further, the present invention provides an effect that, when the luminescent region in the specimen is observed, the objective lens can be focused on the luminescent region in the specimen without confirming the luminescence from the luminescent region.

The focal position determining method and focal position determining apparatus according to the present invention select, in the above-described (7), two focal positions from the plural focal positions accumulated by the execution based on the plural feature data accumulated by the execution, and determine, in the above-described (8), the central position (substantial central position) between the two focal positions as the focal position focused on the observed target region based on the selected two focal positions. The present invention provides an effect that the focal position of the objective lens focused on the observed target region in the specimen can easily be determined.

In the focal position determining method and focal position determining apparatus according to the present invention, the two focal positions are the focal position (substantial focal position) of the objective lens at the near point and the focal position (substantial focal position) of the objective lens at the far point. The present invention provides an effect that the focal position of the objective lens focused on the observed target region in the specimen can easily and simply be determined.

The focal position determining method and focal position determining apparatus according to the present invention select, in the above-described (7), one focal position from the plural focal positions accumulated by the execution based on the plural feature data accumulated by the execution, and determine, in the above-described (8), the position apart from the focal position by the predetermined distance as the focal position focused on the observed target region based on the selected the one focal position and the predetermined distance. The present invention provides an effect that the focal position of the objective lens focused on the observed target region in the specimen can more easily be determined.

In the focal position determining method and focal position determining apparatus according to the present invention, the one focal position is the focal position (substantial focal position) of the objective lens at the near point or the focal position (substantial focal position) of the objective lens at the far point. The present invention provides an effect that the focal position of the objective lens focused on the observed target region in the specimen can more easily and simply be determined.

The focal position determining method and focal position determining apparatus according to the present invention (9) image the specimen at the focal position determined at the above-described (8), (10) calculate the feature data based on the imaged image, (11) change the focal position determined at the above-described (8), (12) image the specimen at the changed focal position, (13) calculate the feature data based on the imaged image, (14) compare the feature data calculated at (10) and the feature data calculated at (13), (15) re-determine the focal position changed at (11) as the focal position of the objective lens focused on the observed target region when the feature data calculated at (13) is greater as the result of the comparison. The present invention provides an effect that the focal position of the objective lens focused on the observed target region in the specimen can be continuously determined not only at the time of setting the specimen but also from the start of the observation of the luminescence of the specimen, with the result that the objective lens can always be focused on the observed target region.

In the focal position determining method and focal position determining apparatus according to the present invention, the specimen is a living cell or tissue. The present invention provides an effect that a material emitting feeble light can be used as a specimen.

In the focal position determining apparatus according to the present invention, an aperture is formed at the pupil position of an illumination optical system including the light irradiator (light source). The present invention provides an effect that a phase difference between transmitted light and diffraction light can be increased, with the result that the contrast of the imaged image can be increased.

In the focal position determining apparatus according to the present invention, the aperture is decentered relative to the optical axis. The present invention provides an effect that a phase difference between transmitted light and diffraction light can be more increased, with the result that the contrast of the imaged image can be more increased.

In the focal position determining apparatus according to the present invention, a narrow-band-pass filter is arranged to the illumination optical system including the light irradiator (light source). The present invention provides an effect that light emitted from a light source can be made to be monochromatic light whose wavelength band width is extremely narrow, with the result that the contrast of the imaged image can be increased.

In the focal position determining apparatus according to the present invention, the light irradiator (light source) emits monochromatic visible light. The present invention provides an effect that, when light emitted from the light source is irradiated to the specimen, the wavelength dispersion hardly appears, so that a sharp diffraction light can be obtained, with the result that the contrast of the imaged image can be increased.

The focal position determining apparatus according to the present invention further includes an exciting light irradiator (exciting light source) that irradiates exciting light to the specimen. The present invention provides an effect that fluorescence and luminescence of the specimen can simultaneously be observed.

In the focal position determining method according to the present invention, the specimen (specifically, a biological specimen containing a luminescent material, etc.) is imaged while moving the objective lens, as well as the focal position of the objective lens is measured, the contrast that is the difference between the maximum value and the minimum value of the pixel value of each pixel composing the image is calculated based on the imaged image, and the focal position of the objective lens focused on the observed target region is determined based on the calculated contrast and the measured focal position of the objective lens. When the specific region in the specimen is defined as the observed target region, and the luminescence of the observed target region is observed, the focal position of the objective lens focused on the observed target region can be determined at the time of setting the specimen, and therefore, the focal position of the objective lens can be focused on the observed target region. Further, the present invention provides an effect that, when the luminescent region in the specimen is observed, the objective lens can be focused on the luminescent region in the specimen without confirming the luminescence from the luminescent region.

In the focal position determining method according to the present invention, the contrast is the difference between the average value of plural high-order pixel values, including the maximum value, of the pixel values of each pixel composing the image and the average value of plural low-order pixel values, including the minimum value, of the pixel values of each pixel composing the image. The present invention provides an effect that, even if a false signal (e.g., a signal caused by noise light such as reflection light or scattering light) is included in the imaged image, the contrast having high reliability can be calculated from the image.

In the focal position determining method according to the present invention, the calculated contrast is compared to the others so as to search one minimum value, and the focal position of the objective lens when the image that is the original of the searched minimum value is imaged is determined as the focal position of the objective lens focused on the observed target region. The present invention provides an effect that the focal position of the objective lens focused on the observed target region in the specimen can easily be determined.

In the focal position determining method according to the present invention, the calculated contrast is compared to the others so as to search two maximum values, and the center between the focal positions of the objective lens when images that are the originals of the searched maximum values are imaged is determined as the focal position of the objective lens focused on the observed target region. The present invention provides an effect that the focal position of the objective lens focused on the observed target region in the specimen can easily be determined.

In the focal position determining method according to the present invention, the objective lens is moved with its moving amount reduced stepwisely. The present invention provides an effect that the focal position of the objective lens focused on the observed target region in the specimen can be immediately determined.

In the focal position determining method according to the present invention, the objective lens is moved with its moving amount reduced to the half the previous moving amount. The present invention provides an effect that the focal position of the objective lens focused on the observed target region in the specimen can be immediately determined.

(II) The present inventor has been developing and examining various imaging techniques from the above-mentioned standpoint. According to this examination, it has been proved that an image can be formed only by luminescence emitted from a single cell by imaging the cell with an optical system in which a square of (NA÷β), which is represented by a numerical aperture (NA) and a projection magnification (β) of an objective lens, is not less than 0.01. To one's surprise, this imaging condition may be applicable to any specimens of a biological origin, which is difficult to be imaged, and according to this imaging condition, a cell image with a feeble luminous component, which cannot directly be observed with naked eyes (and under a microscope) such as bioluminescence can be imaged in a short period (e.g., within 20 minutes). Further, according to the optical condition pursued by the inventor, a cell image that can be formed within a short period such as within 1 to 5 minutes, and that can be analyzed can be provided, when the optical condition represented by a square of a numerical aperture (NA)/projection magnification (β) of an objective lens in an imaging apparatus is not less than 0.071.

Firstly, the inventor has acquired an overall image of a test specimen with an objective lens having a low magnification so as to confirm a desired luminescent region in a field of view. In this case, it has been found that the desired luminescent region is mostly a area in the observation field of view and remains in a microregion, so that it is difficult to analyze or confirm its function. In view of this, the inventor intends to magnify the desired resin in the observation field of view for observation. However, the present inventor has found a technical problem that when a feeble luminescent image of a bioluminescent protein, for example, is desired to be acquired, merely increasing the magnification of the objective lens darkens the field of view and hence the luminescent image might not easily be recognized.

The present invention provides a method and an apparatus that specify an image of a desired luminescent region, and magnify and display this region. The important constituent of the present invention is that, when a test specimen emitting feeble light is observed by magnification imaging optical unit including a lens (or when a test specimen is observed and acquired as an image), the image of the desired region including the luminescent region is magnified and displayed based on the described image (or the image element in the desired region in the described image is designated, the designated image element is magnified with an optional magnification rate to be displayed).

On the other hand, it has been found that a fusion gene obtained by fusing a fluorescent-related gene that expresses a fluorescent protein in addition to a transfer base sequence and a luminescence-related gene is transduced into a cell, a fluorescent image of the cell is acquired, and it is determined whether a bioluminescent protein is located or not at the predetermined region in the cell based on the obtained fluorescent image. It is an effective method in which the luminescent position by a luminescent protein in the cell is marked by utilizing luminescence by the fluorescent material as described above. However, even if the luminescent position in the cell is specified by utilizing the fluorescence by the fluorescent material, this region is generally a microportion in the cell and only a region in the observation field of view. Therefore, some imaging devices of a CCD camera, which images this region, are only related to the reception of light, resulting in that the resolution of the obtained image might be insufficient. Specifically, only a blurred image is obtained.

In view of this, even in a case in which fluorescence by a fluorescent material is utilized, a luminescent position by a luminescent protein in a cell is recognized, then, marking is performed at this position so as to define this position as a luminescent position in the cell by the luminescent protein, and thereafter, a digital zooming or optical zooming is performed to this region to obtain a magnified image of the desired region (alternatively, in a feeble light measuring apparatus that observes feeble luminescence by a luminescence-related gene transduced into a cell, a luminescent region in a cell containing a bioluminescent protein that emits feeble light is identified by fluorescence emitted from a fluorescent material labeled in the vicinity thereof, and the image of the identified luminescent region is magnified to be produced as a magnification image).

According to the present invention, an overall image of a test specimen is obtained with an objective lens having a low magnification, a desired luminescent region in the field of view is confirmed, and only this part is zoomed up, whereby a magnified observation image in which the desired luminescent region is specified can be obtained. The focal position of the objective lens is determined by using the focal position determining method or the focal position determining apparatus of the objective lens so as to digitally or optically zoom up the image of the test specimen, whereby the determination of the focal position and the description and magnification of the image can continuously be performed.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A focal position determining method for determining a focal position of an objective lens focused on an observed target region in a specimen, the method comprising:
    irradiating a living specimen with a visible light, the living specimen being imaged while moving the objective lens;
    measuring a focal position of the objective lens;
    calculating an irradiance contrast from a difference between a maximum value and a minimum value of pixel values of each pixel composing an irradiance image based on the imaged irradiated living specimen;
    determining a second focal position of the objective lens focused on an observed target region based on the calculated irradiance contrast and the measured focal position of the objective lens;
    stopping the light irradiance of the living specimen after determining the second focal position of the objective lens;
    imaging the living specimen with the objective lens at the determined second focal position, the living specimen being imaged using luminescence from the living specimen while not irradiating the living specimen;
    moving the objective lens and measuring a luminescence focal position of the objective lens;
    calculating a luminescence contrast based on the luminescent image; and
    re-determining the second focal position of the objective lens based on the calculated luminescence contrast and the measured luminescence focal position.

2. The focal position determining method according to claim 1, wherein the irradiance contrast is a difference between an average value of plural high-order pixel values, including the maximum value of the pixel values of each pixel composing the irradiance image and an average value of plural low-order pixel values, including the minimum value of the pixel values of each pixel composing the irradiance image.

3. The focal position determining method according to claim 1, wherein the calculated irradiance contrast is compared to other irradiance contrast values so as to identify one minimum value, and the focal position of the objective lens used when capturing the irradiance image corresponding to the identified minimum value is determined as the second focal position.

4. The focal position determining method according to claim 1, wherein the calculated irradiance contrast is compared to other irradiance contrast values so as to identify two maximum values, and a center between focal positions of the objective lens used when capturing irradiance images that correspond to the identified maximum values is determined as the second focal position.

5. The focal position determining method according to claim 1, wherein the objective lens is moved with its moving amount reduced stepwisely.

6. The focal position determining method according to claim 5, wherein the objective lens is moved with its moving amount reduced to half of a previous moving amount.

7. A feeble light detecting apparatus that describes an image of a living specimen of a biological origin by using an optical imager, comprising:
    a light irradiating unit that irradiates the living specimen with a visible light;
    a specimen imaging unit that images the living specimen;
    an objective lens that is disposed between the living specimen and the specimen imaging unit;
    an objective lens moving unit that moves the objective lens along an optical axis;

an objective lens position measuring unit that measures a position of the objective lens on the optical axis; and a control unit controlling the light irradiating unit to irradiate the living specimen with the visible light and then causes the specimen imaging unit to image the living specimen while moving the objective lens causing the objective lens position measuring unit to measure a focal position of the objective lens, the control unit calculating, based on an image of the irradiated living specimen, an irradiance contrast from a difference between a maximum value and a minimum value of pixel values of each pixel composing an irradiance image of the living specimen, determining, based on the calculated irradiance contrast and the measured focal position of the objective lens, a second focal position of the objective lens, causing the light irradiating unit to stop the light irradiation after determining the second focal position of the objective lens, causing the specimen imaging unit to image the living specimen with the objective lens at the determined second focal position, the specimen imaging unit imaging the living specimen using luminescence from the living specimen while not irradiating the living specimen, and while moving the objective lens, causing the objective lens position measuring unit to measure a luminescence focal position of the objective lens, calculating a luminescence contrast, based on the luminescent image, and re-determining the second focal position of the objective lens based on the calculated luminescence contrast and the measured luminescence focal position, wherein the control unit causes the specimen imaging unit to perform an image forming step of describing the luminescent image of the living specimen with the use of the optical imager; an image extracting step of extracting a desired area from the luminescent image obtained at the image forming step; and an image magnifying step of magnifying the desired area obtained at the image extracting step.

8. The feeble light detecting apparatus according to claim 7, further comprising at least one of an image unit that displays the magnified luminescent image of the desired area that is a part of the living specimen as overlapped with a bright field image or a dark field image of the living specimen; or an image recording unit that records the luminescent image.

9. A feeble light detecting method in which an image of a test specimen of a biological origin is described, the method comprising:
irradiating a living specimen with a visible light, the living specimen specimen being imaged while moving the objective lens;
measuring a focal position of the objective lens;
calculating an irradiance contrast from a difference between a maximum value and a minimum value of pixel values of each pixel composing an irradiance image based on the imaged irradiated living specimen;
determining a second focal position of the objective lens focused on an observed target region based on the calculated irradiance contrast and the measured focal position of the objective lens;
stopping the light irradiance of the living specimen after determining the second focal position of the objective lens;
imaging the living specimen with the objective lens at the determined second focal position, the living specimen being imaged using luminescence from the living specimen while not irradiating the living specimen;
moving the objective lens and measuring a luminescence focal position of the objective lens;
calculating a luminescence contrast based on the luminescent image;
re-determining the second focal position of the objective lens based on the calculated luminescence contrast and the measured luminescence focal position;
extracting a desired area from the luminescent image; and
displaying or recording the desired area as magnified.

10. The feeble light detecting method according to claim 9, wherein the magnified image of the desired area that is a part of the living specimen is displayed or recorded as overlapped with a bright field image or a dark field image of the living specimen.

11. The feeble light detecting method according to claim 9, wherein the image magnifying step is an optical image magnifying step or an image magnifying step by an electrical processing.

* * * * *